(12) United States Patent
Peterson

(10) Patent No.: US 8,198,230 B2
(45) Date of Patent: *Jun. 12, 2012

(54) SYNTHETIC MIMICS OF MAMMALIAN CELL SURFACE RECEPTORS: METHOD AND COMPOSITIONS

(75) Inventor: Blake R. Peterson, University Park, PA (US)

(73) Assignee: The Penn State Research Foundation, University Park, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/930,494

(22) Filed: Jan. 7, 2011

(65) Prior Publication Data

US 2011/0236344 A1 Sep. 29, 2011

Related U.S. Application Data

(60) Division of application No. 12/317,473, filed on Dec. 22, 2008, now Pat. No. 7,947,647, which is a division of application No. 11/368,661, filed on Mar. 6, 2006, now Pat. No. 7,514,400, which is a continuation-in-part of application No. 11/242,388, filed on Oct. 3, 2005, now abandoned.

(60) Provisional application No. 60/616,391, filed on Oct. 6, 2004.

(51) Int. Cl.
*C07K 14/00* (2006.01)
(52) U.S. Cl. .......................................... 514/1; 530/350
(58) Field of Classification Search ....... 514/1; 530/350
See application file for complete search history.

(56) References Cited

OTHER PUBLICATIONS

Boonyarattanakalin et al., "Snythetic Mimics of Small Mammalian Cell Receptors", Dec. 22, 2004, J. American Chemical Society 126(50): 16379-16386.
Caron et al., "Endosome Disruption enhances the Functional Nuclear Delivery of Tat-fusion Proteins", Jun. 18, 2004, Biochem. Biophys. Res. Commun. 319(1):12-20.
Hussey, Stephen L., et al., "A Synthetic Membrane-Anchored Antigen Efficiently Promotes Uptake of Antifluorescein Antibodies and Associated Protein A by Mammalian Cells", J. Am. Chem. Soc., 2001, vol. 123, pp. 12712-12713.
Hussey et al., Synthesis of chimeric 7a-substituted estradiol derivatives linked to cholesterol and cholesterylamine. 2002. Organic Letters. 4(3): 415-418.
Hussey, Stephen L., et al., "Efficient Delivery of Streptavidin to Mammalian Cells: Clathrin-Mediated Endocytosis Regulated by a Synthetic Ligand", J. Am. Chem. Soc., 2002, vol. 124, pp. 6265-6273.
Kakudo, Tomoyuki et al., "Transferrin-Modified Liposomes Equipped with a pH-Sensitive Fusogenic Peptide: An Artificial Viral-like Delivery System", Biochemistry, 2004, vol. 43, pp. 5618-5628.
Martin, Scott E., et al., "Non-Natural Cell Surface Receptors: Synthetic Peptides Capped with N-Cholesterylglycine Efficiently Deliver Proteins into Mammalian Cells", Bioconjugate Chem., 2003, vol. 14, pp. 67-74.
Sanyal et al., "A transforming growth factor-a-Pseudomonas exotoxin hybrid protein undergoes pH-dependent conformational changes conducive to membrane interaction." 1993. Biochemistry. 32: 3488-3497.
Summerton, James E., "Endo-Porter: A Novel Reagent for Safe, Effective Delivery of Substances into Cells", Ann. N.Y. Acad. Sci., 2005, vol. 1058, pp. 62-75.
Zeng, Weiguang, et al., "Highly Immunogenic and Totally Synthetic Lipopeptides as Self-Adjuvanting Immunocontraceptive Vaccines", The J. of Immunology, 2002, vol. 169, pp. 4905-4912.
Christian Plank, Wolfgang Zauner, and Ernst Wagner, "Application of membrane-active peptides for drug and gene delivery across cellular membranes", Advanced Drug Delivery Reviews 34 (1998), 1998 Elsevier Science B.V., pp. 21-35, Vienna, Austria.
Alicia E. Smith and Ari Helenius, "How Viruses Enter Animal Cells", Science, vol. 304, Apr. 9, 2004, pp. 237-242.
Michael Forgac, "Vacuolar ATPases: rotary proton pumps in physiology and pathophysiology", Nature Reviews—Molecular Cell Biology, Nature Publishing Group, vol. 8, Nov. 2007, pp. 917-929.

*Primary Examiner* — Karen Carlson
(74) *Attorney, Agent, or Firm* — McKee, Voorhees & Sease, P.L.C.

(57) ABSTRACT

The present invention relates to new synthetic receptors. More particularly, the present invention relates to the use of the synthetic receptors for delivering a protein, peptide, drug, prodrug, lipid, nucleic acid, carbohydrate or small molecule into a target cell via receptor-mediated endocytosis. According to the invention, novel synthetic mimics of cell surface receptors have been designed and methods for use of the same are disclosed.

8 Claims, 26 Drawing Sheets
(12 of 26 Drawing Sheet(s) Filed in Color)

(A) Subcellular localization of receptors 6-9

(B) Percentage of receptors on the cell surface (C) Cellular stability of receptor 2

(A) Cells treated with 2 and 3.

(B) Cells treated with *L. monocytogenes*, 2, and 3.

DIC  Fluorescence  DIC + Fluorescence

Florescent synthetic receptor

SYNTHETIC MIMICS OF MAMMALIAN CELL SURFACE RECEPTORS: METHOD AND COMPOSITIONS

CROSS-REFERENCE TO RELATED APPLICATIONS

This application is a Divisional of U.S. application Ser. No. 12/317,473 filed Dec. 22, 2008, which is a Divisional of U.S. application Ser. No. 11/368,661 filed Mar. 6, 2006, which is a Continuation-in-part Application of U.S. application Ser. No. 11/242,388 filed Oct. 3, 2005, which is incorporated herein by reference in their entirety, which claims benefit of U.S. Provisional Application 60/616,391, filed Oct. 6, 2004, the contents of which are incorporated into this application by reference in their entirety.

GRANT REFERENCE

This invention was made with government support under Grant No. RO1-CA83831, awarded by the National Institutes of Health. The Government has certain rights in the invention.

FIELD OF THE INVENTION

The present invention relates to new synthetic receptors. More particularly, the present invention relates to the use of the synthetic receptors for delivering a protein, peptide, drug, prodrug, or a small molecule into a target cell via receptor-mediated endocytosis. According to the invention, novel synthetic mimics of cell surface receptors have been designed and methods for use of the same are disclosed.

BACKGROUND OF THE INVENTION

It is often difficult to deliver compounds, such as proteins, peptides, and other drugs and diagnostic compounds intracellularly because cell membranes often resist the passage of these compounds. Various methods have been developed to administer agents intracellularly.

One method for transmembrane delivery of exogenous molecules having a wide applicability is based on the mechanism of receptor-mediated endocytotic activity. Unlike many other methods, receptor-mediated endocytotic activity can be used successfully both in vivo and in vitro. Receptor-mediated endocytosis involves the movement of ligands bound to membrane receptors into the interior of an area bounded by the membrane through invagination of the membrane. The process is initiated or activated by the binding of a receptor-specific ligand to the receptor. Many receptor-mediated endocytotic systems have been characterized, including those recognizing galactose, mannose, mannose 6-phosphate, transferrin, asialoglycoprotein, transcobalamin (Vitamin $B_{12}$), alpha-2-macroglobulins, insulin, and other peptide growth factors such as epidermal growth factor (EGF).

Investigators in the field agree that the assimilation of physiologically significant molecules such as nutrients, hormones, enzymes, virions, toxins, and various types of proteins begins with the initial binding of the macromolecule or ligand to specific receptors which are mobile and randomly distributed on the cell membrane surface. These ligand-receptor complexes rapidly accumulate in specialized regions of the membrane termed coated pits. From this stage, the receptor-mediated endocytosis (RME) proceeds to the formation of smooth-walled vesicles which allow entry of the concentrated ligand-receptor complexes into the cell. These vesicles, often referred to as "endosomes" or "receptosomes," may fuse together or combine with larger vesicles. Subsequently, the internal pH of these endosomes decrease by the action of proton pumps, changing the conformation of the receptor and/or ligand. The result is the release of the ligand and the formation of separate receptor-containing vesicles and ligand-containing ones. In some cases, the receptor-bearing vesicles are delivered to the cell membrane where they are released and "recycled" for additional use. In others, the resulting vesicles, along with the internalized ligand, are delivered to and fused with lysosomes where the eventual breakdown likely takes place. Another destination of some ligands internalized by RME including certain drugs, viral proteins, and protein toxins is escape from endosomes and entry into the cellular cytoplasm or nucleus.

Receptor-mediated endocytotic activity has been utilized for delivering exogenous molecules such as proteins and nucleic acids to cells. Generally, a specified ligand is chemically conjugated by covalent, ionic or hydrogen bonding to an exogenous molecule of interest (i.e. the exogenous compound), where the modified ligand is still able to bind to its cognate receptor. Disadvantageously, this method limits delivery of the exogenous molecule to cells that display a particular receptor.

Thus, there exists a need for a delivery system which can be utilized for the delivery of agents, including pharmaceuticals, small molecules, peptides and oligonucleotides, to any cell or tissue.

BRIEF SUMMARY OF THE INVENTION

We describe various synthetic receptors and their uses. In one aspect of the present invention, synthetic receptors are provided in which the receptor includes the following regions: at least one binding, chelating, or mimicking motif linked to a membrane-binding element that anchors the receptor to a plasma membrane of a cell. In another embodiment, the binding, chelating, or mimicking motif and membrane-binding element are linked to the other via a linker region. In one aspect, the membrane-binding element includes at least of one the following: cholesterol, dihydrocholesterol, ergosterol, brassicasterol, derivatives of cholesterol, dihydrocholesterol, ergosterol, brassicasterol, and related compounds thereof. In a preferred embodiment, the membrane-binding element includes at least one of the following: cholesterylamine, dihydrocholesterylamine, ergosterylamine, brassicasterylamine, derivatives of cholesterylamine, dihydrocholesterylamine, ergosterylamine, brassicasterylamine, and related compounds thereof.

Additional embodiments of the synthetic receptors include synthetic protein-binding receptors, synthetic metal-chelating receptors, synthetic immunoglobulin Fc-binding receptors, synthetic cytokine or growth factor-binding receptors, synthetic drug-binding receptors, synthetic lipid mimicking receptors, and synthetic transmembrane receptors.

Another embodiment includes the loading of low-density lipoprotein (LDL) with synthetic receptors for the delivery of proteins, carbohydrates, nucleic acids, lipids, or drugs, to cells, tissues, or tumors.

Provided herein are methods for delivering a protein into a cell that includes contacting the cell with a synthetic cell receptor so that the synthetic receptor inserts into the cell plasma membrane on the cell's surface. The synthetic receptor has a protein-binding motif and a membrane-binding element that anchors the synthetic receptor into the cell plasma membrane. The inserted synthetic receptor binds a protein via its protein-binding motif, thereby triggering receptor-mediated endocytosis of the protein-bound synthetic receptor and delivery of the protein into the cell.

In another embodiment, the present invention provides pharmaceutical compositions comprising a synthetic receptor and a pharmaceutically acceptable carrier. The present invention further includes methods of using the synthetic receptors for various applications. In one embodiment, the synthetic receptors may be used as cellular probes.

In another embodiment, the present invention provides a method of treating a disease, disorder, or condition comprising delivering a therapeutically effective amount of a protein, peptide, drug, prodrug, or small molecule into a target cell using a synthetic cell receptor. In one aspect, the synthetic receptors may be used in enzyme replacement therapy or to treat viral, yeast, or bacterial infections, cancer, inflammation, or autoimmune diseases.

In addition, the invention includes methods of modulating the immune response of a subject by removing a protein of interest from circulation in a subject, in particular extra-cellular ligands. In another embodiment, a method for inducing apoptosis by contacting a synthetic lipid-mimicking receptor with a cell is provided. Also, provided herein are methods of using synthetic metal chelating receptors as a contrast agent in a patient in need of an MRI by delivering a synthetic metal chelating receptor into a cell population either in vivo, ex vivo or in vitro. Methods of this invention are useful for in vitro and in vivo applications.

BRIEF DESCRIPTION OF THE FIGURES

The patent or application file contains at least one drawing executed in color. Copies of this patent or patent application publication with color drawings will be provided by the Office upon request and payment of the necessary fee.

The numbered receptors in FIGS. 1-13, 14-19, and 20-25 correspond with receptors in examples 1-14, 15-21, and 22-24 respectively.

DETAILED DESCRIPTION OF THE PREFERRED EMBODIMENT

Figure 1:
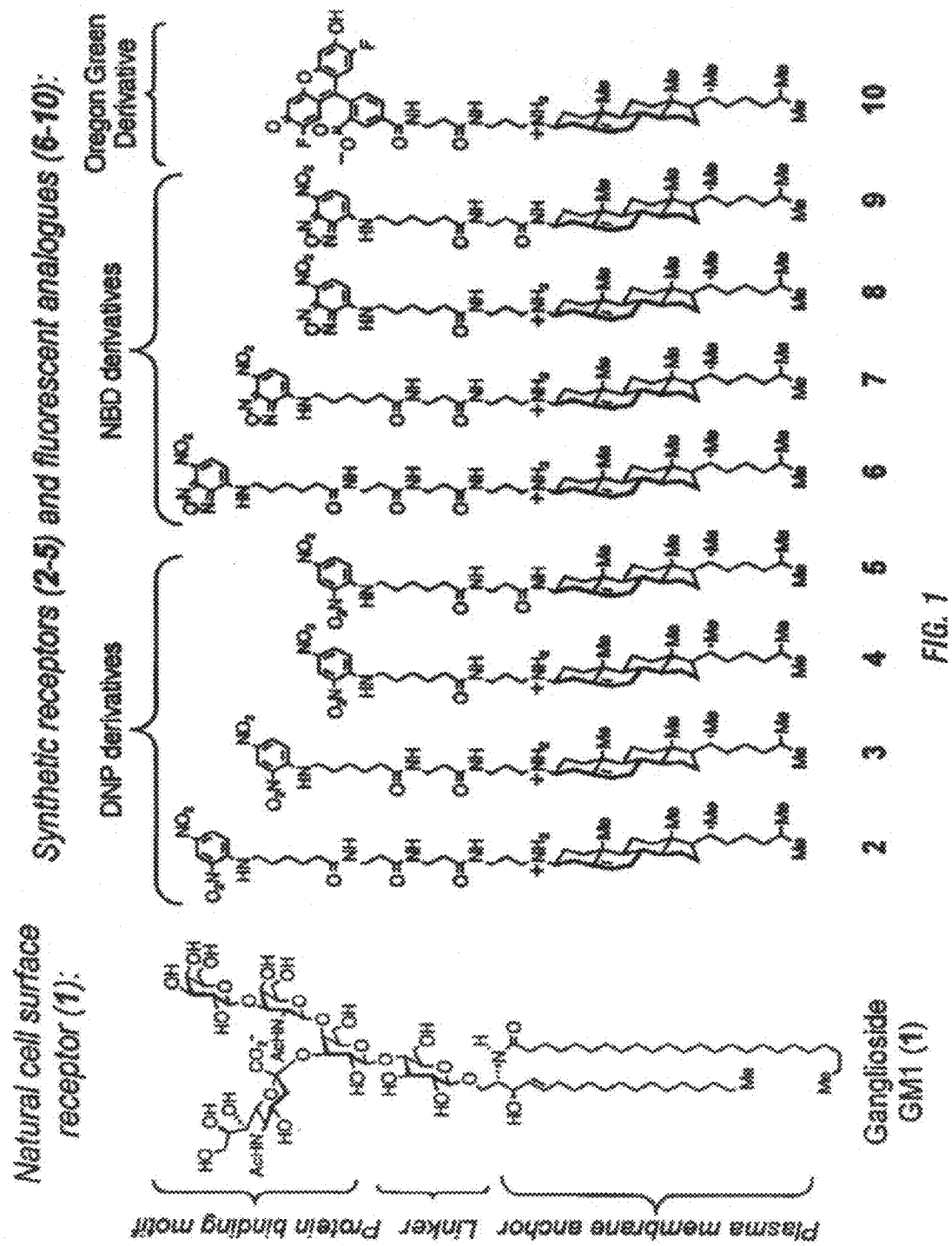
FIG. 1. Structures of the small natural receptor ganglioside GM1, novel synthetic receptors, and related control compounds.
Figure 2:
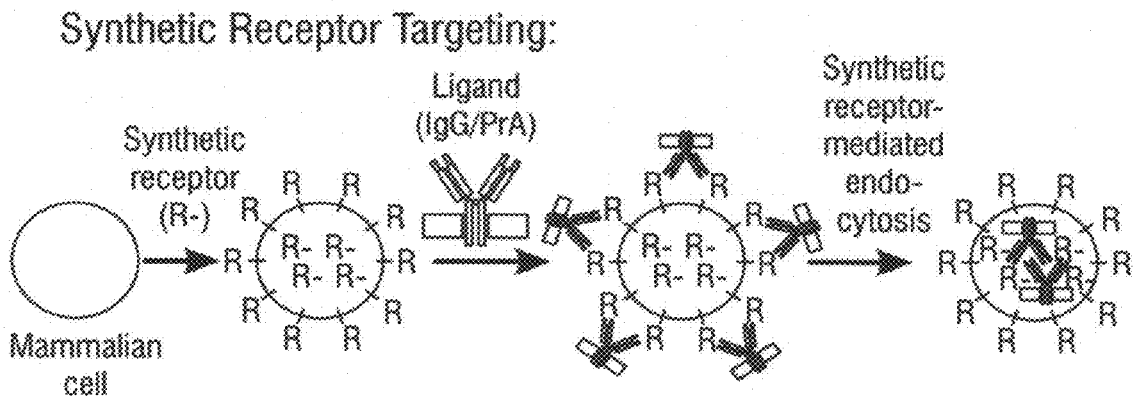
FIG. 2. The synthetic receptor targeting approach for enhancing cellular uptake of impermeable ligands. Synthetic mimics of cell surface receptors are added to living mammalian cells. These cells internalize cognate ligands such as macromolecular antibodies (IgG) bound to bacterial protein A (PrA) by synthetic receptor-mediated endocytosis.
Figure 3:
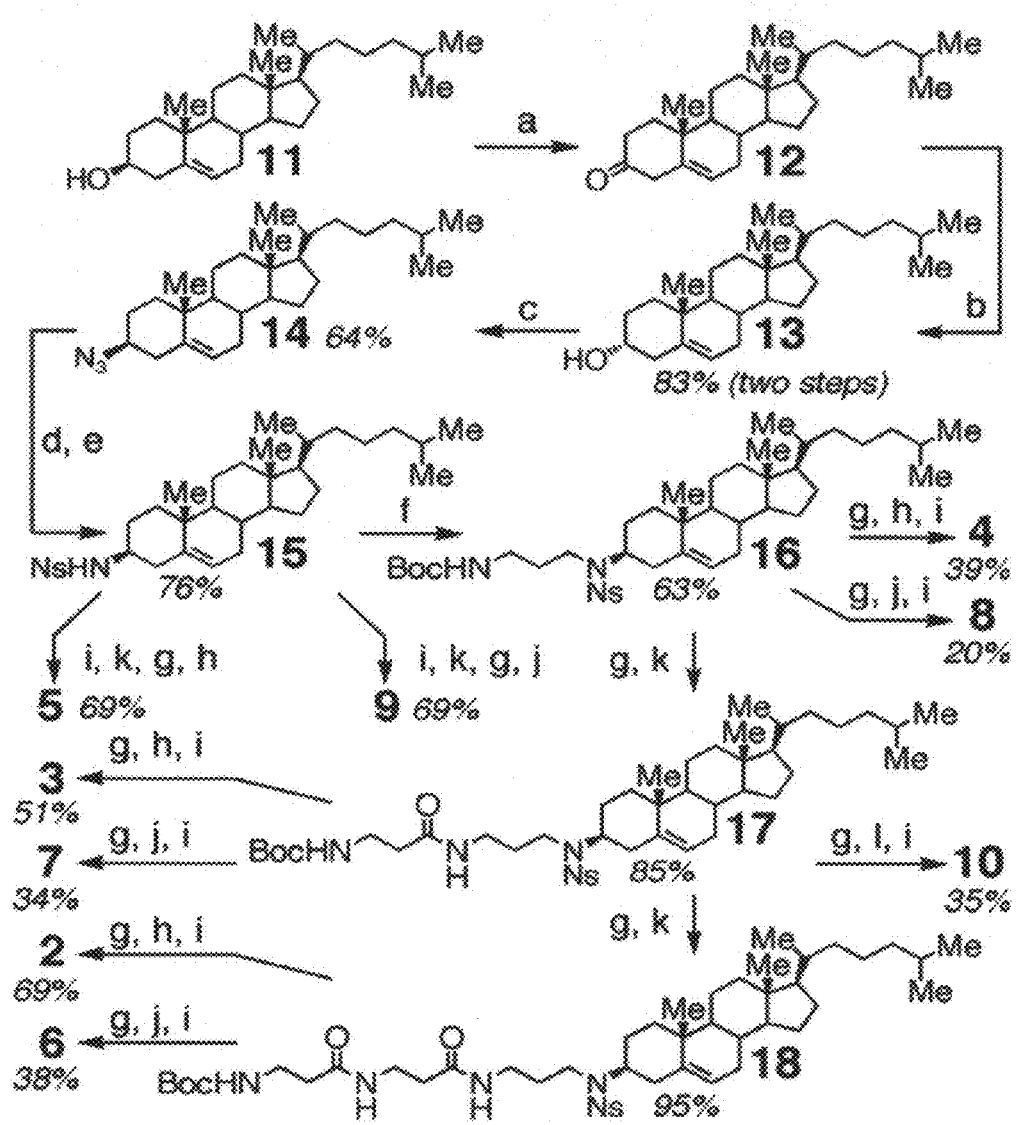
FIG. 3. The construction of synthetic receptors by modifying a previously reported synthesis of 3beta-cholesterylamine. The reagents and the conditions that correspond with the figure are as follows: (a) Oxalyl chloride, DMSO, $CH_2Cl_2$, TEA, $-78°$ C. (b) L-Selectride, THF, $-78°$ C. (c) $PPh_3$, $HN_3$, DEAD, benzene. (d) $LiAlH_4$, $Et_2O$, $0°$ C. (e) 2-Nitrobenzensulfonyl chloride, DIEA, THF. (f) Boc-3-chloropropylamine, $K_2CO_3$, DMA, $120°$ C. (g) TFA, $CH_2Cl_2$ (2:25), (h) 2,4-Dinitrophenylaminocaproate NHS ester, DIEA, $CH_2Cl_2$. (i) PhSH, $K_2CO_3$, THF/DMF (1:4). (j) 6-(N-(7-nitrobenz-2-oxa-1,3-diazol-4-yl)amino)hexanoic acid succinimidyl ester, DIEA, $CH_2Cl_2$. (k) Boc-β-alanine NHS ester, DIEA, $CH_2Cl_2$, (l) 5-carboxyoregongreen NHS ester, DIEA, DMF.
Figure 4:
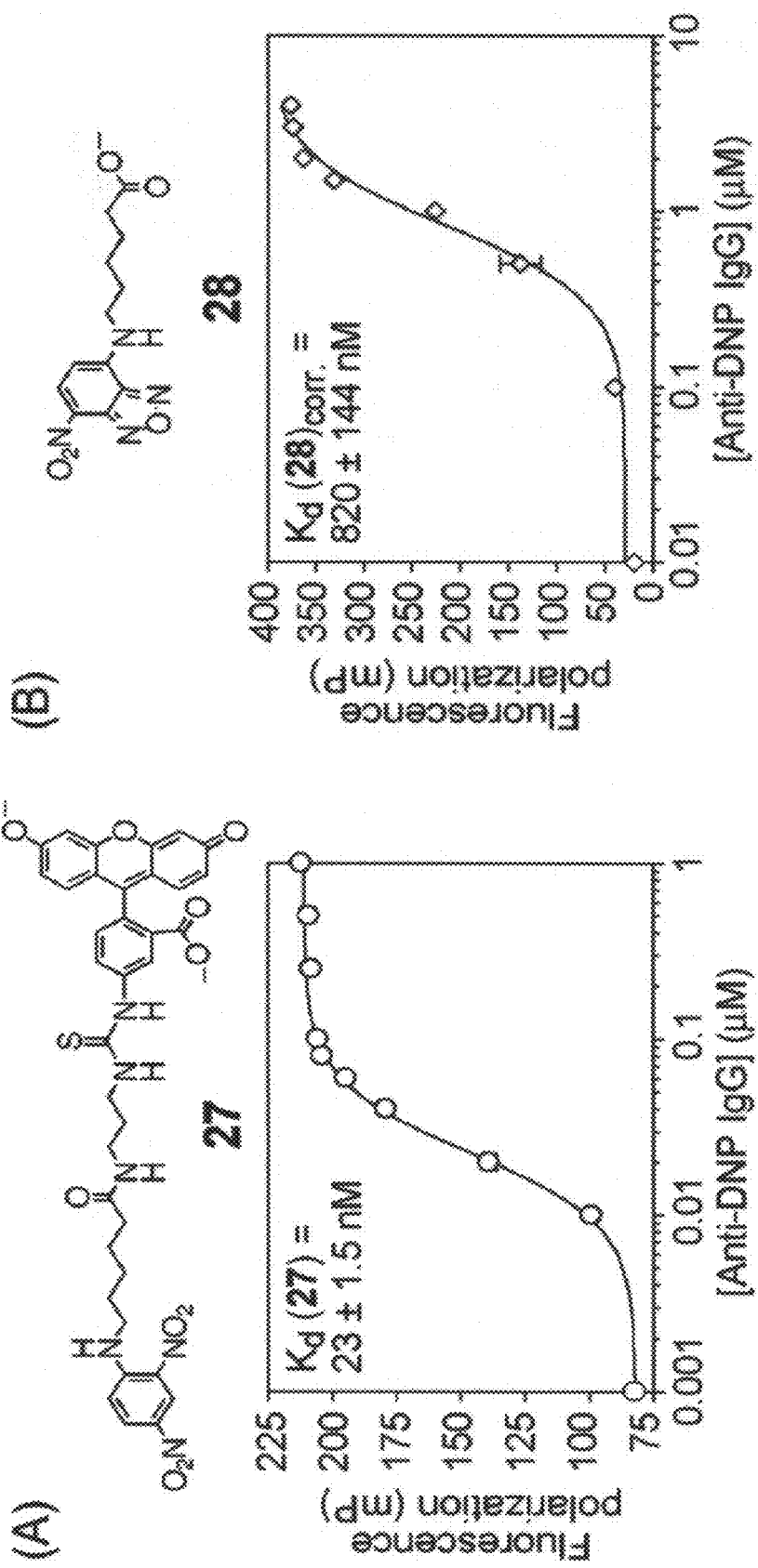
FIG. 4. Determination of the apparent affinities of DNP (27, Panel A) and NBD (28, Panel B) derivatives for rabbit polyclonal anti-DNP IgG (Sigma) by fluorescence polarization. The fluorescein moiety of 27 is shown in the dianionic form that predominates at pH 7.4.[1] Fixed concentrations of 27 (20 nM) and 28 (100 nM) in PBS (pH 7.4, 100 μL) were employed. The data shown in Panel B was corrected to compensate for partial binding-induced quenching of the NBD fluorophore.[2,3] These experiments were run in triplicate, and errors reflect 95% confidence intervals.
Figure 5:
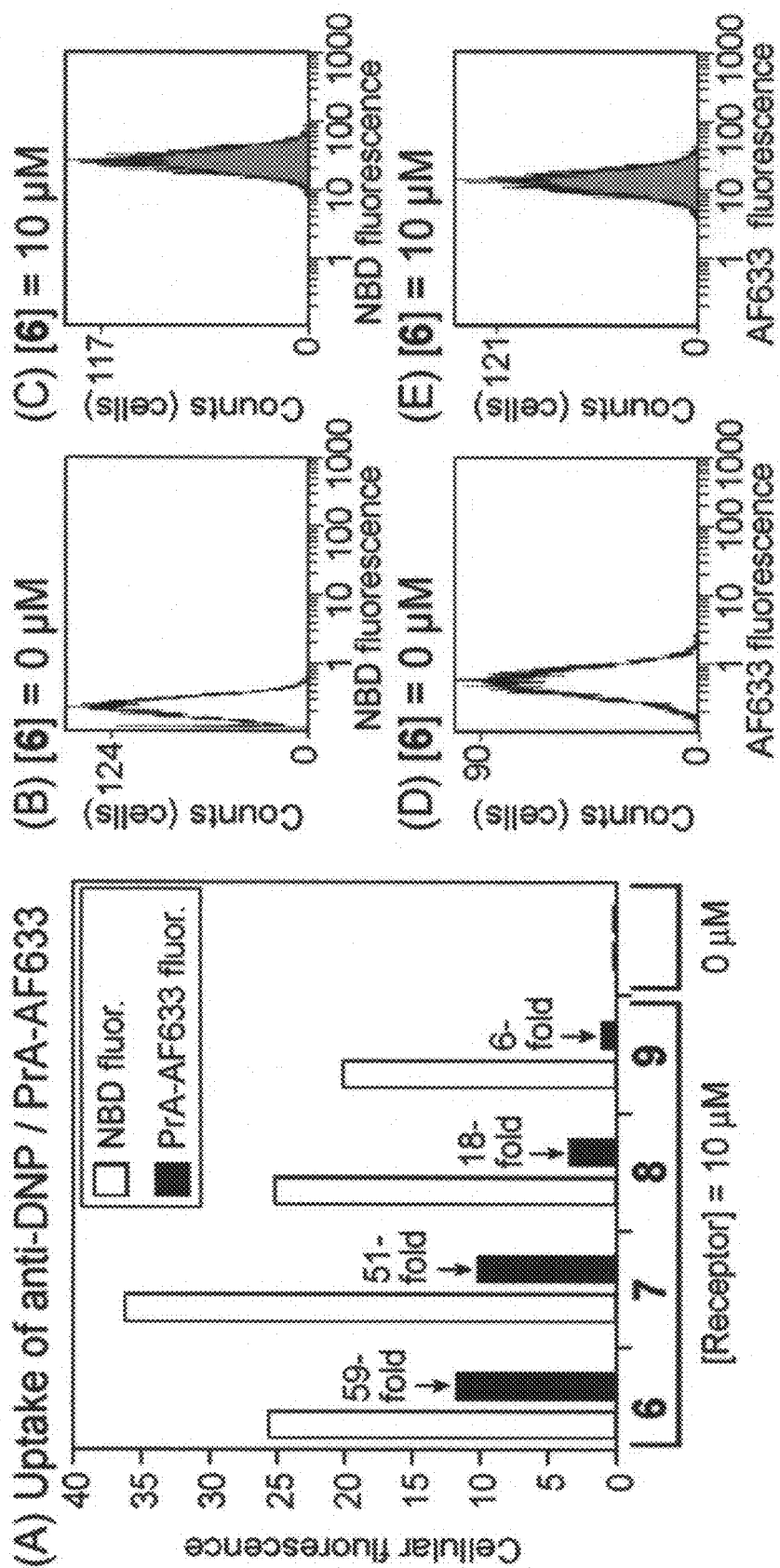
FIG. 5. Analysis of uptake of red fluorescent anti-DNP/PrA-AF633 by cells treated with the green fluorescent receptors 6-9. Jurkat lymphocytes were treated with receptors 6-9 (10 μM) for 1 h followed by addition of anti-DNP/PrA-AF633 for 4 h. Cells were washed with media containing 6-(2,4-dinitrophenyl)aminohexanoic acid (100 μM) to remove any non-internalized protein prior to analysis by flow cytometry. Panel A: Median green (NBD) and red (AF633) cellular fluorescence resulting from treatment with 6-9 and anti-DNP/PrA-AF633. Panels B-E: the distribution of green and red cellular fluorescence after treatment with anti-DNP/PrA-AF633 alone or receptor 6 (10 μM) and anti-DNP/PrA-AF633. UV absorbance measurements were employed to equalize receptor concentrations prior to addition to cells. Total cellular fluorescence from the NBD groups of receptors 6-9 was within two-fold.
Figure 6:
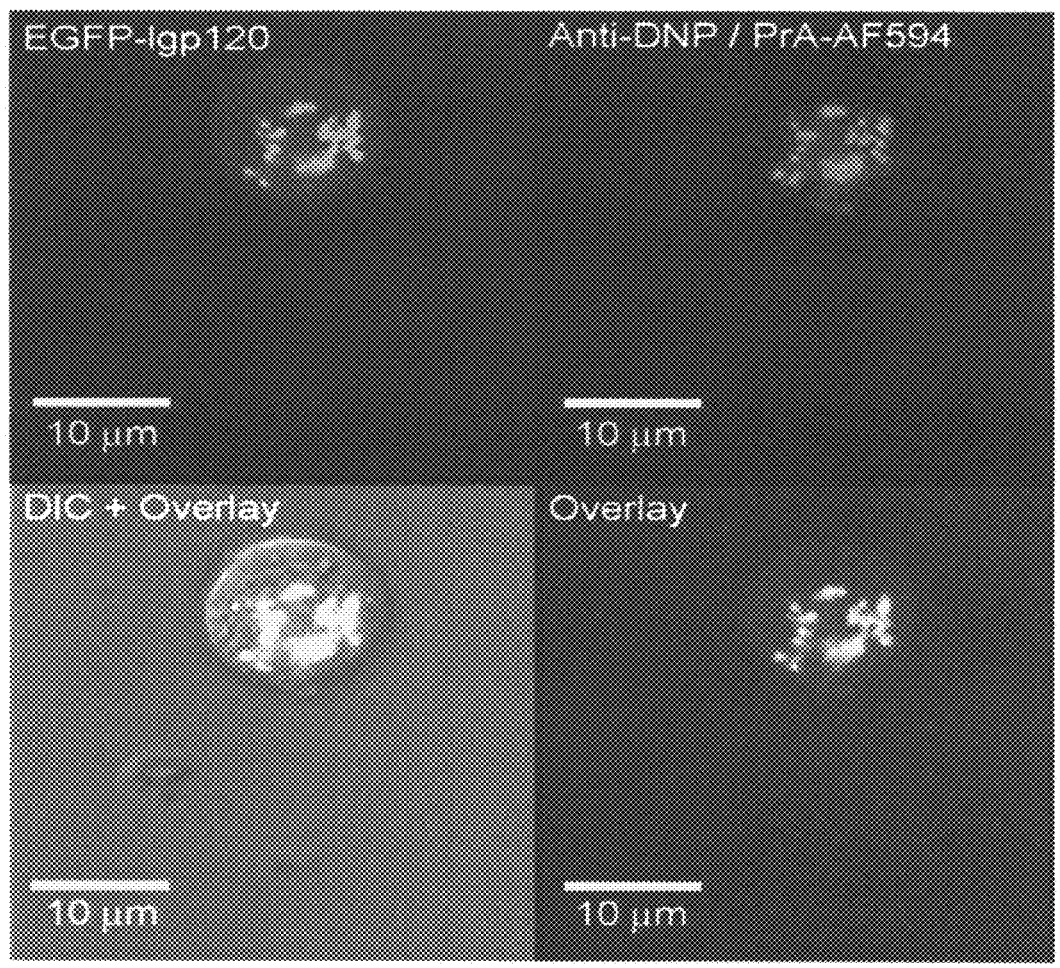
FIG. 6. Confocal laser scanning and DIC microscopy of living Jurkat lymphocytes treated with green fluorescent receptor 9 (10 μM) and red fluorescent BODIPY TR ceramide (5 μM) as a probe of the golgi apparatus and nuclear membrane. Yellow pixels indicate colocalization of green and red fluorophores. These experiments revealed that the ineffective receptor 9 (the N-acyl analogue) exhibits a unique intracellular localization compared with receptors 6-8.
Figure 7:
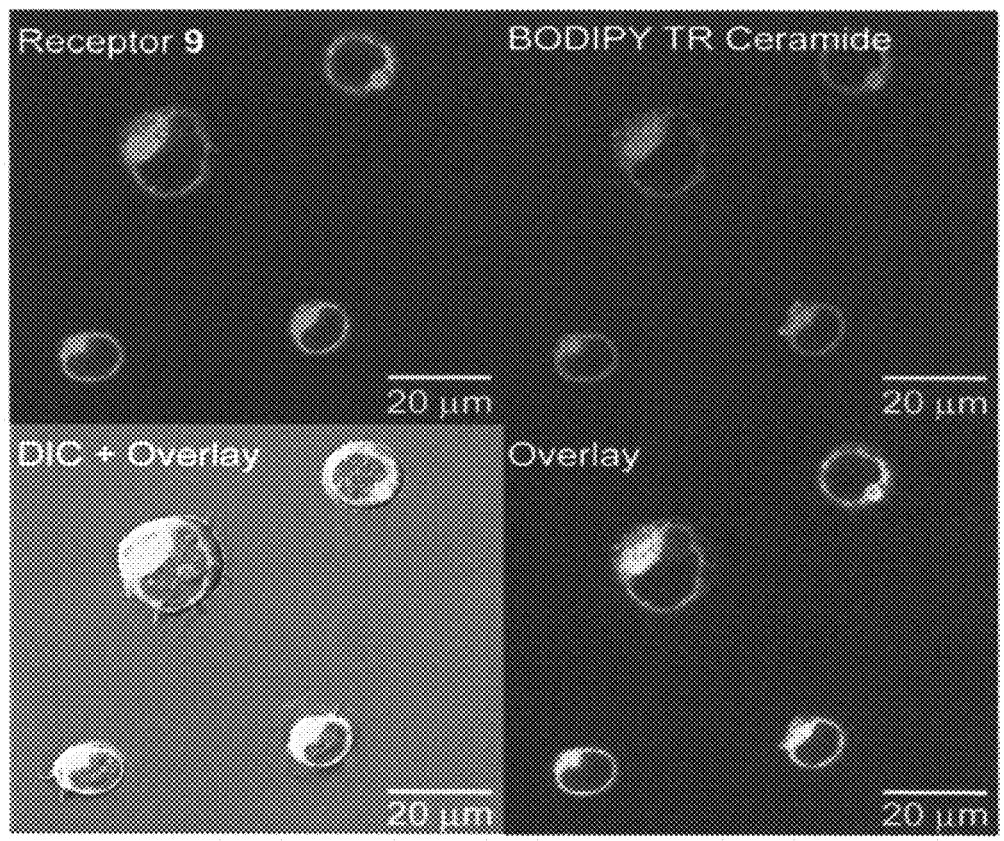
FIG. 7. Confocal laser scanning and DIC microscopy of living Jurkat lymphocytes transfected with the green fluorescent late endosome/lysosome marker EGFP-lgp120[4] and subjected to ligand uptake mediated by receptor 2. Transfected cells were treated with receptor 2 (10 μM) for 1 h followed by addition of red fluorescent anti-DNP/PrA-AF594 for 4 h. Yellow pixels indicate colocalization of green and red fluorophores.

The present invention relates to new synthetic receptors. More particularly, the present invention relates to the use of the synthetic receptors for delivering a polymer, protein, peptide, drug, prodrug, or small molecule into a target cell via receptor-mediated endocytosis. Thus, one aspect of the present invention is to deliver a desired protein, peptide, prodrug, or small molecule from the outside of a cell to the inside of a cell. The present inventors contemplate the use of synthetic receptors to treat a variety of diseases, conditions, and disorders, including those for which the conventional therapeutic alternatives are not very effective or are non-existent.

The present inventors are the first to recognize that synthetic receptors comprising membrane-binding elements of cholesterol, dihydrocholesterol, ergosterol, brassicasterol, derivatives of cholesterol, dihydrocholesterol, ergosterol, brassicasterol, and related compounds thereof linked to a protein binding group provide a novel mechanism for receptor mediated endocytosis of the synthetic receptor bound to at least one specific protein and delivery of the protein to the endosome/lysosome. Briefly, when the synthetic receptors are added to living cells, the synthetic receptors' membrane-binding elements insert into the cell's plasma membranes, project a protein-binding motif from the cell surface so that the protein-binding motif binds a cognate protein. The synthetic receptor undergoes receptor-mediated endocytosis allowing the cell to internalize the conjugate of protein bound to the synthetic receptor. In addition, the synthetic receptors allow for cycling between plasma membranes and intracellular endosomes.

The synthetic receptor according to the invention may, in addition, be linked or conjugated to other molecules, including but not limited to for example, a labeling molecule which makes it possible, for example, to visualize the distribution or localization of the synthetic receptor after administration in vitro or in vivo. In another aspect of the invention, the protein that binds to the protein-binding motif may be labeled to visualize the distribution or localization of the protein-bound synthetic receptor after administration in vitro or in vivo.

One unique and novel aspect of the synthetic receptors described here is their ability to bind low-density lipoprotein (LDL) and/or other lipoproteins prior to their uptake by cells. Certain mammalian cells take up LDL loaded with synthetic receptors via natural LDL receptors expressed on the cell surface. This delivery mechanism enables targeting of these compounds to specific cells or tissues in vivo. Because tumors often overexpress natural LDL receptors, the synthetic receptors described here enable tumor or tissue targeting in vivo. Cell lines that lack LDL receptors or that possess other cholesterol uptake mechanisms can take up synthetic receptors through other mechanisms of action.

I. Synthetic Receptors

A. Synthetic Target-Binding Receptors

In one embodiment of the invention, a synthetic receptor comprises a membrane-binding element and a target-binding motif. In another embodiment, a synthetic receptor comprises a membrane-binding element, a linker region, and a target-binding motif. The above and other features and advantages of the present invention will become more apparent in the following description of the various embodiments in greater detail.

One embodiment of a synthetic receptor is shown below:

Another embodiment of a synthetic receptor is shown below:

Another embodiment of a synthetic receptor is shown below:

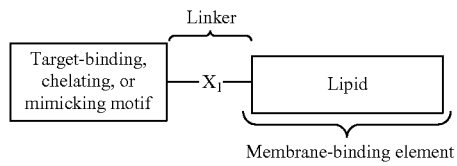

Another embodiment of a synthetic receptor is shown below:

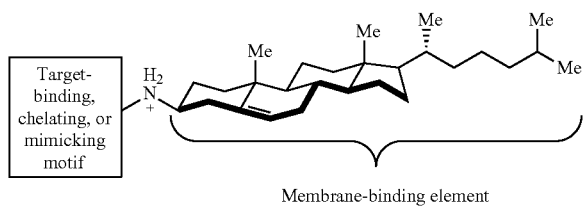

Another embodiment of a synthetic receptor is shown below:

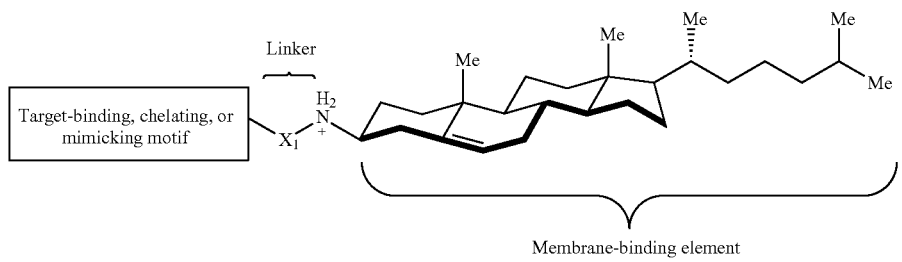

As used herein, the term "membrane-binding element" includes molecules that can be inserted into a lipid membrane through a hydrophobic anchor and allows the molecule to reside on the cell surface or reside on the cell surface and cycle between endosomes and cell surface. In one aspect of the invention, the membrane-binding element comprises proteins, peptides, peptidomimetics, phospholipids, sphingolipids, steroids, cholesterol, dihydrocholesterol, ergosterol, brassicasterol, derivatives of proteins, peptides, peptidomimetics, phospholipids, sphingolipids, steroids, cholesterol, dihydrocholesterol, ergosterol, brassicasterol, and related compounds thereof. In one aspect of the invention, the membrane-binding element comprises cholesterylamine, dihydrocholesterylamine, ergosterylamine, brassicasterylamine, derivatives of cholesterylamine, dihydrocholesterylamine, or ergosterylamine, brassicasterylamine, and related compounds thereof. In one aspect of the invention, the membrane-binding element comprises 3-cholesterylamine, 3-dihydrocholesterylamine, 3-ergosterylamine, derivatives of 3-cholesterylamine, 3-dihydrocholesterylamine, 3-ergosterylamine, or 3-brassicasterylamine, and related compounds thereof. As used herein, the term "derivative" refers to a chemical substance related structurally to another, i.e., an "original" substance, which can be referred to as a "parent" compound. The term "derivative" as used herein with reference to proteins, peptides, peptidomimetics, phospholipids, sphingolipids, steroids, cholesterol, dihydrocholesterol, ergosterol, brassicasterol, derivatives of cholesterol, dihydrocholesterol, ergosterol, brassicasterol, of the membrane-binding element of the present invention refers to a molecule that contains at least the portion of the proteins, peptides, peptidomimetics, phospholipids, sphingolipids, cholesterol, dihydrocholesterol, ergosterol, brassicasterol, derivatives of cholesterol, dihydrocholesterol, ergosterol, brassicasterol, and related compounds thereof that allows the molecule to insert into a cell plasma membrane. Examples of derivatives of cholesterol include cholesteryl esters and cholesteryl carbamates. The term "derivative" as used herein with reference to 3-cholesterylamine, 3-dihydrocholesterylamine, or 3-ergosterylamine of the membrane-binding element of the present invention refers to a molecule that contains at least the portion of the 3-cholesterylamine, 3-dihydrocholesterylamine, 3-ergosterylamine, or 3-brassicasterylamine, that allows the molecule to insert into a cell plasma membrane. The term "derivative" as used herein with reference to 3β-cholesterylamine, 3β-dihydrocholesterylamine, 3β-ergosterylamine, or 3β-brassicasterylamine of the membrane-binding element of the present invention refers to a molecule that contains at least the portion of the 3β-cholesterylamine, 3β-dihydrocholesterylamine, 3β-ergosterylamine or 3β-brassicasterylamine that allows the molecule to insert into a cell plasma membrane. Examples of derivatives of 3β-cholesterylamine include, without limitation, N-alkyl, N-aryl, and N-acyl 3β-cholesterylamines. As used herein, the term "related compound" refers to a chemical molecule that associates with the cellular plasma membrane, is hydrophobic and has a positive charge, for example, a positive charge from an amine group, or has a polar functional group that allows the molecule to reside on the cell surface and yet cycle between the endosome and cell surface without becoming trapped intracellularly. Examples include without limitation a protonated cholesterylamine or a cholesteryl ester, cholesteryl amide, cholesteryl ether, or cholesteryl carbamate linked to another polar or non-polar headgroup. The membrane-binding element as described above can be used with any of the synthetic receptors of the present invention regardless of the various binding, chelating or mimicking motifs and/or use of a linker region.

The present inventors also contemplate that a membrane-binding element with an affinity for membranes can be created by enhancing the hydrophobicity of the membrane-binding element domain (e.g., increasing the amount of hydrophobic residues or functional groups, replacing non-hydrophobic residues with hydrophobic residues, and swapping in a hydrophobic domain that consists of entirely hydrophobic residues).

In another aspect of the present invention, as shown above, the synthetic receptor comprises a linker region that links the target-binding motif of the synthetic receptor to the membrane-binding element of the synthetic receptor. The linker region is structurally variable and can have one or multiple functions depending on the intended use of the receptor. For example, the linker region (shown as position $X_1$ in the embodiments above) may include but is not limited to zero, one, or more atoms selected from the group of atoms, C, N, S, and O and/or other chain-extending atoms, zero, one, or more alkane, alkene, alkyne, aryl, ketone, amine, amide, ester, ether, urea, carbamate, heterocyclic, and related functional groups, either linear or cyclic, zero, one, or more alpha, beta, gamma, and delta amino acids as well as aminohexanoic acid and related structures. These amino acid subunits may also include side-chains such as those found in natural L- and nonnatural D-configuration alpha amino acids or other amino acids. The linker may serve as a spacing group between the membrane-binding element and the protein-binding motif so as to minimize the possibility that the membrane-binding element will interfere with the interaction or binding of the binding motif with the target molecule, e.g., a peptide, protein, carbohydrate small molecule, drug, prodrug or nucleic acid that is to be internalized. The target molecule may be noncovalently bound or covalently linked to the target-binding motif. The linker may also facilitate association with LDL, with the cell surface, and rapid cycling between the cell surface and endosomes, as demonstrated by the present inventors in Example 11 and as discussed below. In addition, the linker region may contribute to receptor localization and ligand uptake efficiency. See Examples 8 and 9. The linker as described above can be used with any of the synthetic receptors of the present invention regardless of the differing membrane-binding elements or the various target-binding, chelating or mimicking motifs.

One embodiment of a synthetic protein-binding receptor is shown below:

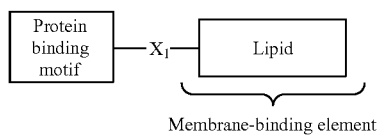

Another embodiment of a synthetic protein-binding receptor is shown below:

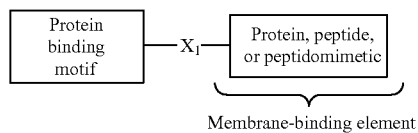

Another embodiment of a synthetic protein-binding receptor is shown below:

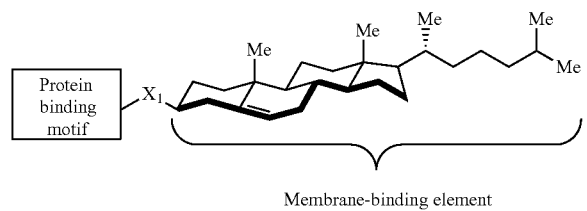

Another embodiment of a synthetic protein-binding receptor is shown below:

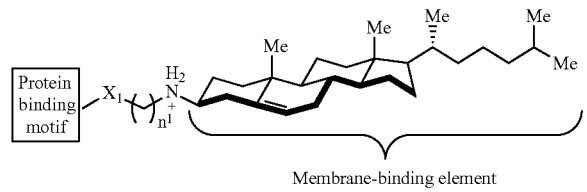

Referring to the embodiment shown above, the linker comprises zero, one or more atoms that may be selected from the group of atoms, C, N, S, and O and/or other chain-extending atoms repeated 0 to 100 or more times as indicated by the symbol $n_1$. The linker region comprises one or more groups selected from the following: alkane, alkene, alkyne, aryl, ketone, amine, amide, ester, ether, urea, carbamate, heterocyclic, and related functional groups in position $X_1$. These functional groups can be linear or cyclic. Furthermore, the linker may comprise 0 to 100 or more subunits such as alpha, beta, gamma, and delta amino acids as well as aminohexanoic acid and related structures with 0 to 100 or more atoms between the amine and carboxylic acid. These amino acid subunits may also include side-chains such as those found in natural L- and nonnatural D-configuration alpha amino acids or other amino acids.

In another aspect, the linker comprises one or more alpha amino acids, beta amino acids, gamma amino acids, delta amino acids, 6 aminohexanoic acid or related compounds to facilitate association with the cell surface and rapid cycling between the cell surface and endosomes. In another aspect, the linker region is located between the last amine of the cholesterylamine and the first amino acid of the protein-binding or other binding element. In another aspect, the linker region has at least three carbon atoms between the cholesterylamine and the first polar functional group (such as an amide).

Figure 10:
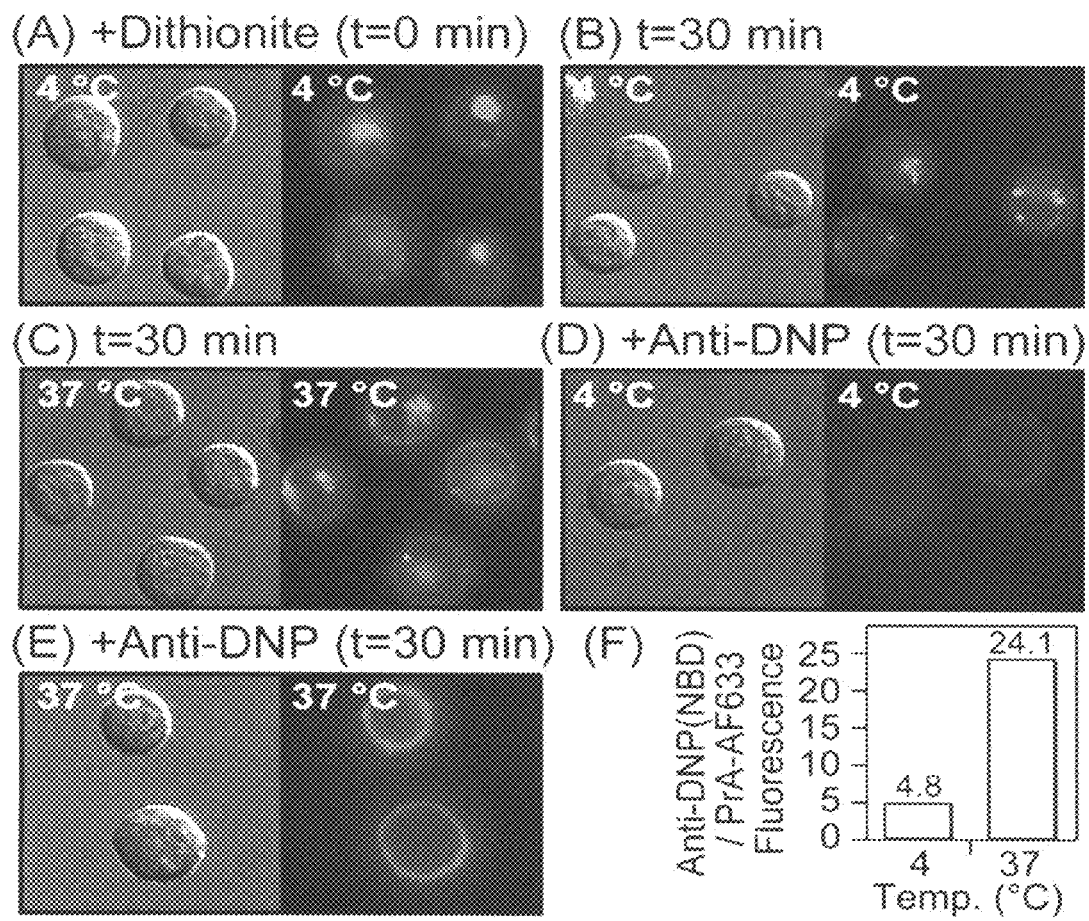
FIG. 10. Cycling of receptor 6 between cell surface and intracellular endosomes in Jurkat lymphocytes. Panels A-E: DIC (left) and epifluorescence (right) micrographs of cells captured after treatment with 6 (10 μM, 1 hour) followed by quenching of cell surface fluorophores at 4° C. with sodium dithionite (30 mM, 5 min). Cells were washed with ice-cold media (time=0 minutes, Panel A), split up into two portions, and return of green fluorescence to the cell surface was examined as a function of time and temperature (Panels A-C). Cells were again cooled to 4° C. prior to detection of NBD headgroups at the cell surface with red fluorescent anti-DNP/PrA-AF633 by epifluorescence microscopy (Panels D-E, time=30 minutes) and flow cytometry (Panel F, time=30 minutes). NBD fluorescence is shown in the panels A-C, PrA-AF633 florescence is shown in panels D-F.

Remarkably, the present inventors have found that modifying the linker region of the synthetic receptor effects the receptor localization and ligand uptake efficiency. The present inventors have found that insertion of amide derivatives of 3β-cholesterylamine in the linker region of the receptor elicits certain effects in trafficking and expression of the receptor on the cell surface. For example, the present inventors have found that N-acyl derivatives of 3β-cholesterylamine in the linker region results in decreased expression of the receptor on the cell surface, especially when compared with the N-alkyl receptors containing β-alanine subunits in the linker. FIG. 10, Example 9. Thus, the linker plays a role in maintaining or increasing a synthetic receptor population on the cell surface by keeping the synthetic receptors cycling from the cell surface to the endosome back to the cell surface. In one aspect of the present invention, the linker region of the synthetic receptor comprises β-alanine subunits. Moreover, results with human Jurkat cell line indicate that these synthetic receptors mimic natural cell surface receptors, as evidenced by its temporal stability on the cell surface and rapid cycling between the cell surface and endosomes.

Interestingly, some receptors containing amide derivatives of 3β-cholesterylamine (N-acyl derivatives) traffic extensively to the golgi apparatus and nuclear membranes of living cells. Depending on the headgroup linked to lipids such as 3β-cholesterylamine derivatives, other N-acyl derivatives are similar to N-alkyl derivatives in membrane localization and trafficking. In one aspect of the present invention, the linker comprises an N-acyl derivative of 3β-cholesterylamine. In another aspect of the present invention, the linker comprises an N-aryl derivative of 3β-cholesterylamine. In another aspect of the present invention, the linker comprises an N-alkyl derivative of 3β-cholesterylamine.

In one aspect of the present invention, the synthetic receptor comprises a target-binding motif. As used herein, "target-binding motif" refers to a region in the receptor that recognizes and binds non-covalently or is covalently linked to a protein, a polypeptide, a peptide, an antibody, an immunoglobulin, a ligand, a cytokine, a growth factor, a nucleic acid, a lipid, membrane, a carbohydrate, a drug, a prodrug, a small molecule or a fragment thereof.

In another aspect of the present invention, the synthetic receptor comprises a protein-binding motif. As used herein, "protein-binding motif" refers to a region in the receptor that recognizes and binds non-covalently or is covalently linked to specific amino acid residues in the context of variable surrounding peptide or protein sequences. Thus, the term protein includes polypeptides, peptides, antibodies, and other protein ligands, including, for example, cytokines, growth factors, immunoglobulins, cell surface receptors, antigens, or drugs or medicine, for example, peptide drugs, glycopeptide antibiotics such as vancomycin and teicoplanin.

In another aspect, the protein-binding motif comprises a protein, peptide or synthetic polymer that disrupts membranes of intracellular endosomes. In one embodiment, the protein includes but is not limited to a viral or bacterial fusogenic protein such as hemagglutinin or listeriolysin O or a fragment thereof. In another embodiment, the peptide includes but is not limited to the peptide termed GALA or endoporter.

See Summerton J E. Endo-porter: a novel reagent for safe, effective delivery of substances into cells. Ann N Y Acad Sci. (2005) 1058: 62-75; Kakudo T, Chaki S, Futaki S, Nakase I, Akaji K, Kawakami T, Maruyama K, Kamiya H, Harashima H, Transferrin-modified Liposomes Equipped with a pH-sensitive Fusogenic Peptide: an Artificial Viral-like Delivery System Biochemistry (2004) 43: 5618-5628.

In another embodiment, the synthetic polymer includes but is not limited to poly(alkylacrylic acids) such as poly(2-propylacrylic acid) and salts thereof.

In one embodiment, the present invention provides a synthetic receptor that is a synthetic immunoglobulin Fc receptor. In one aspect, the synthetic immunoglobulin Fc receptor has a Fc binding region and a membrane-binding element. In another aspect, the synthetic immunoglobulin Fc receptor has a Fc binding region, a linker region, and a membrane-binding element. The membrane-binding element's structure and function have been described above, and examples of the membrane-binding element include but are not limited to N-alkyl, N-aryl, or N-acyl derivatives of 3-cholesterylamine, 3-dihydrocholesterylamine, 3-ergosterylamine, 3-brassicasterylamine and related compounds.

The Fc binding region includes a protein including but not limited to the IgG-binding proteins: Protein A (from *S. aureus*), Protein G, Protein L, or Protein Z, a peptide, a cyclic peptide including but not limited to the minimized protein A variant termed Z34C, or a small molecule that binds the Fc fragment of immunoglobulins. One embodiment of the synthetic immunoglobulin Fc receptor is shown below:

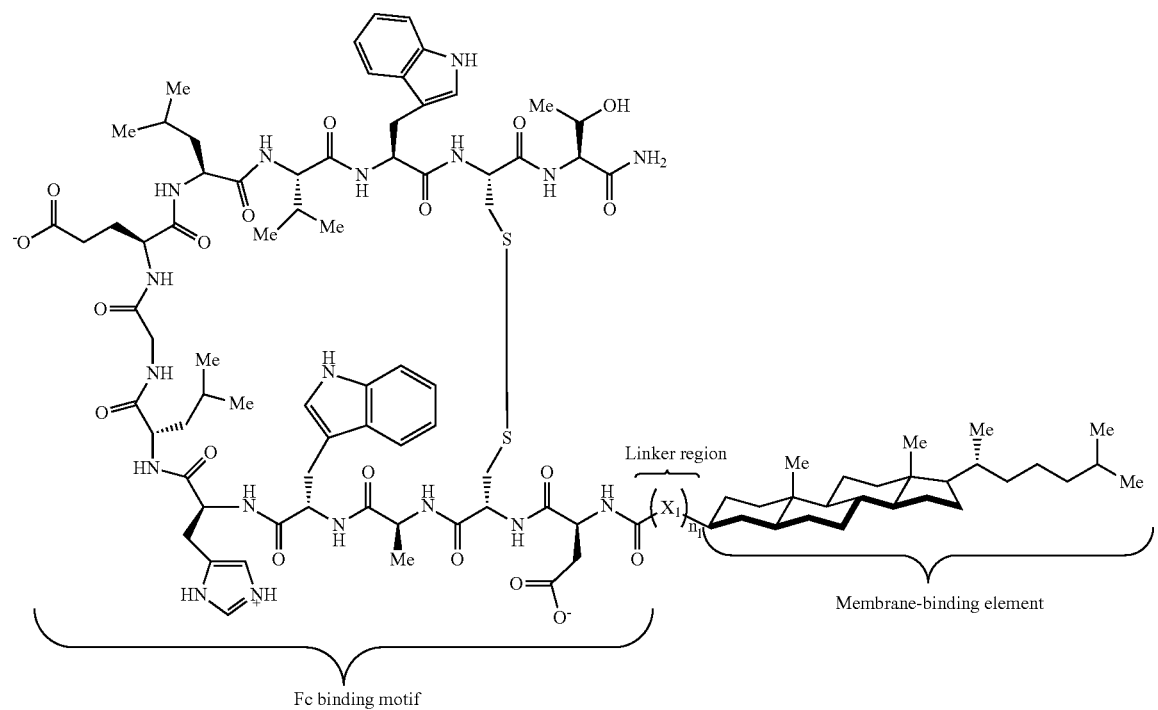

In the embodiment shown above, the linker comprises atoms that may be selected from the group of atoms, C, N, S, and O and/or other chain-extending atoms repeated 0 to 100 or more times as indicated by the symbol $n_1$. In another aspect, the linker region comprises one or more groups selected from the following: alkane, alkene, alkyne, aryl, ketone, amine, amide, ester, ether, urea, carbamate, heterocyclic, and related functional groups in position $X_1$. These functional groups can be linear or cyclic. Furthermore, the linker may comprise 0 to 100 or more subunits such as alpha, beta, gamma, and delta amino acids as well as aminohexanoic acid and related structures with 0 to 100 or more atoms between the amine and carboxylic acid. These amino acid subunits may also include side-chains such as those found in natural L- and nonnatural D-configuration alpha amino acids or other amino acids. These and related synthetic immunoglobulin Fc receptors promote the cellular endocytosis of immunoglobulins by recruiting these proteins to cell surfaces. The synthetic immunoglobulin Fc receptor may also be used to control natural receptors on cell surfaces by providing additional stabilization with the cell surface of antibodies that target natural cell surface receptors. The synthetic immunoglobulin Fc receptor may also be used to deliver therapeutic antibodies into cells. These antibodies include neutralizing antibodies against intracellular bacteria, viruses, and other pathogens. Other therapeutic antibodies that target antigens involved in cellular proliferation may be delivered to interfere with the proliferation of cancer cells. Synthetic immunoglobulin Fc receptors can also be used to deliver IgG into cells in combination with an endosome disruptive agent such as membrane fusogenic proteins, peptides, or synthetic polymers to enable live cell immunolabeling of antigens such as immunofluorescence experiments or to control intracellular processes by binding of targeted biomolecules. Other Fc-binding motifs such as substituted triazines (See: *J. Comb. Chem.* 2004, 6, 862-868) are known to those skilled in the art, and these and related Fc-binding compounds linked to membrane-binding elements are claimed in this application.

One embodiment of the synthetic immunoglobulin Fc receptor is shown below:

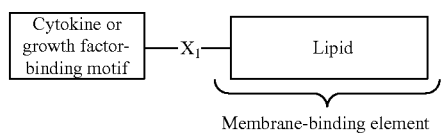

Another embodiment of a synthetic receptor for binding cytokines and growth factors is shown below:

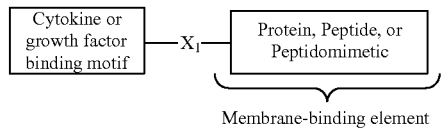

Another embodiment of a synthetic receptor for binding cytokines and growth factors is shown below:

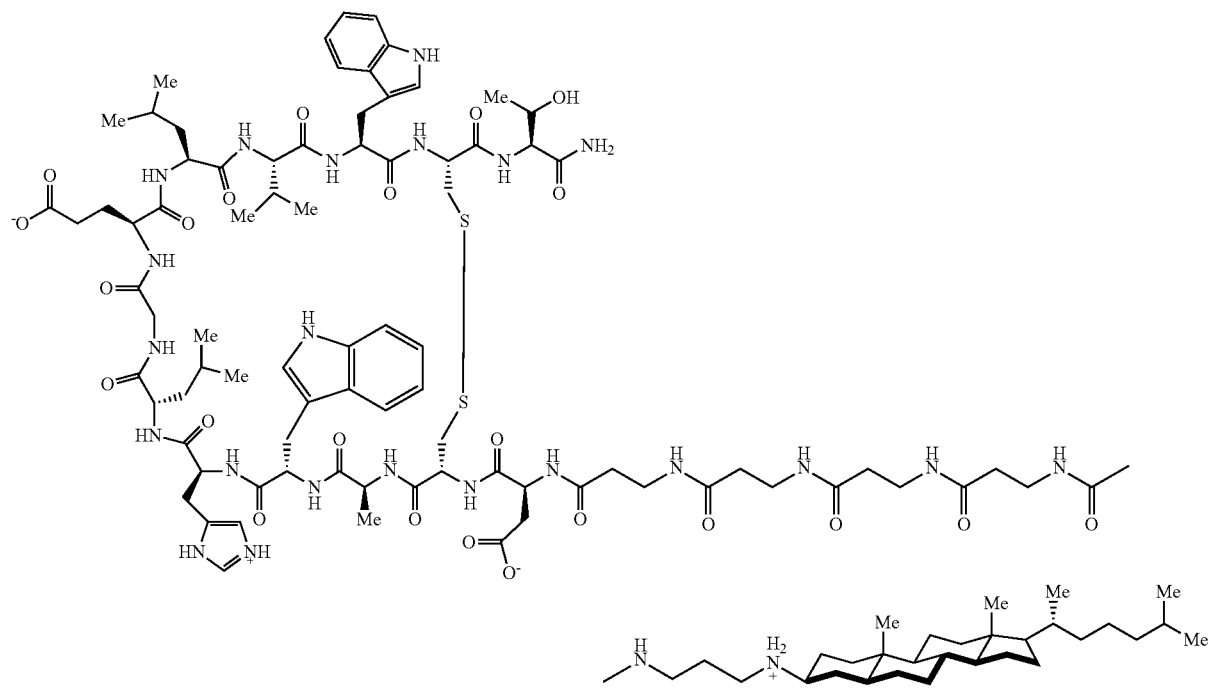

In one embodiment, the present invention provides a synthetic receptor that is a synthetic receptor for cytokines and growth factors. In one embodiment, a synthetic receptor for cytokines and growth factors comprises a cytokine or growth factor-binding motif and a membrane-binding element as described above. In another embodiment, a synthetic receptor for cytokines and growth factors comprises a cytokine or growth factor-binding motif, a linker region as described above, and a membrane-binding element as described above.

The cytokine or growth factor-binding motif may comprise a small molecule, an oligonucleotide, a carbohydrate, a peptide, or a protein-based binding motif that binds an extracellular cytokine or a growth factor. One embodiment of a synthetic receptor for binding cytokines and growth factors is shown below:

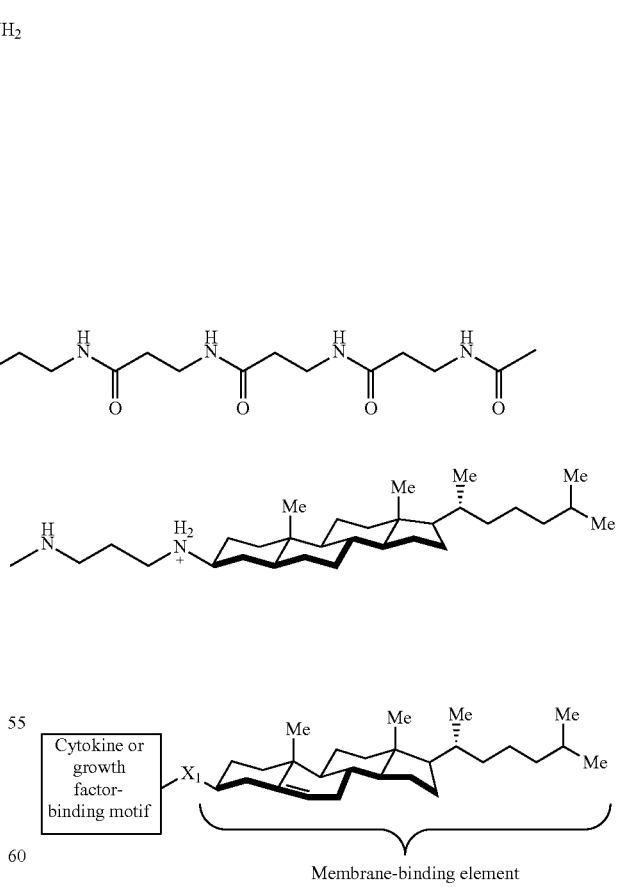

Another embodiment of a synthetic receptor for binding cytokines and growth factors is shown below:

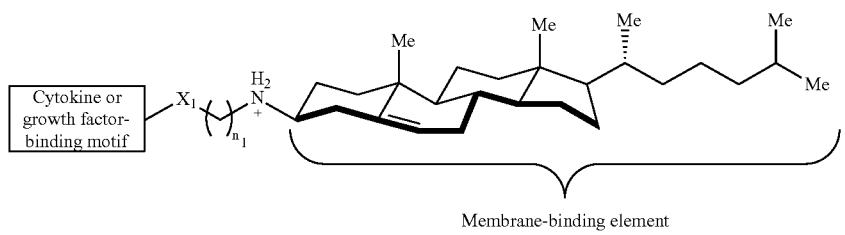

Membrane-binding element

In the embodiment shown above, $n_1$ comprises 0 to 100 or more atoms, $X_1$ comprises one or more linker atoms or functional groups such as amines, amides, carbamates, ureas, esters, or ethers. In another aspect, $X_1$ comprises 0 to 100 linker subunits such as alpha, beta, gamma, or delta amino acids as well as aminohexanoic acid and related structures with 0 to 100 or more atoms between the amine and the carboxylic acid.

In one embodiment, the present invention provides a synthetic receptor that is a synthetic drug delivery receptor. In one embodiment, the synthetic drug delivery receptor has a drug-binding motif and a membrane-binding element. In one embodiment, the synthetic drug delivery receptor has a drug-binding motif, a linker region, and a membrane-binding element. A membrane-binding element's structure and function has been described above. The drug-binding motif may bind non-covalently to drugs or prodrugs or be covalently linked to drugs or prodrugs.

In one aspect, the drug-binding motif comprises a protein, a linear or cyclic peptide, a small molecule, a carbohydrate or oligosaccharide, or a nucleic acid or oligonucleotide. In another aspect, the drug-binding motif is capable of binding non-covalently to or is covalently linked to a drug, a prodrug, a small molecule, a linear or cyclic peptide, a protein, a carbohydrate or oligosaccharide, or a nucleic acid such as a DNA or RNA oligonucleotide, plasmid DNA, siRNA, or ribozyme. Binding of nucleic acids by the synthetic receptor may allow delivery of linear or plasmid DNA into cells for transfection as used in gene therapy, diagnostic, or other applications. Binding of RNA may allow delivery of RNA into cells for antisense or siRNA gene silencing applications. The drug-binding motif can include DNA or RNA intercalators such as ethidium bromide and related compounds or major-groove or minor-groove binding agents that bind nucleic acids.

One embodiment of a synthetic drug delivery receptor is shown below:

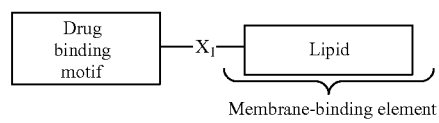

Membrane-binding element

Another embodiment of a synthetic drug delivery receptor is shown below:

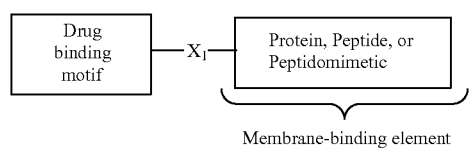

Membrane-binding element

Another embodiment of a synthetic drug delivery receptor is shown below:

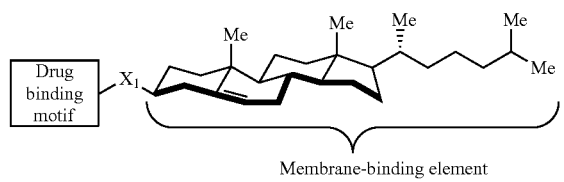

Membrane-binding element

Another embodiment of a synthetic drug delivery receptor is shown below:

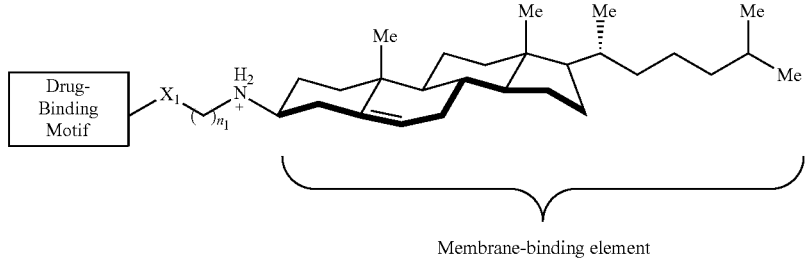

Membrane-binding element

In the embodiment shown above, $n_1$ comprises 0 to 100 or more atoms, $X_1$ comprises one or more linker atoms such as O, N, C, or S, or functional groups such as amines, amides, carbamates, ureas, esters, or ethers. In another aspect, $X_1$ comprises 0 to 100 linker subunits such as alpha, beta, gamma, or delta amino acids as well as aminohexanoic acid and related structures with 0 to 100 or more atoms between the amine and the carboxylic acid.

In another embodiment, a synthetic drug delivery receptor has one or more drug-binding motif linked to N-alkyl, N-aryl, or N-acyl derivatives of cholesterylamine, dihydrocholesterylamine or ergosterylamine. Synthetic drug delivery receptors having more than one drug-binding motif can bind multiple drugs or increase the affinity for a specific drug through multivalent interactions to enhance efficacy.

One embodiment of a synthetic receptor for intracellular delivery and tissue targeting of the antibiotic vancomycin is shown below:

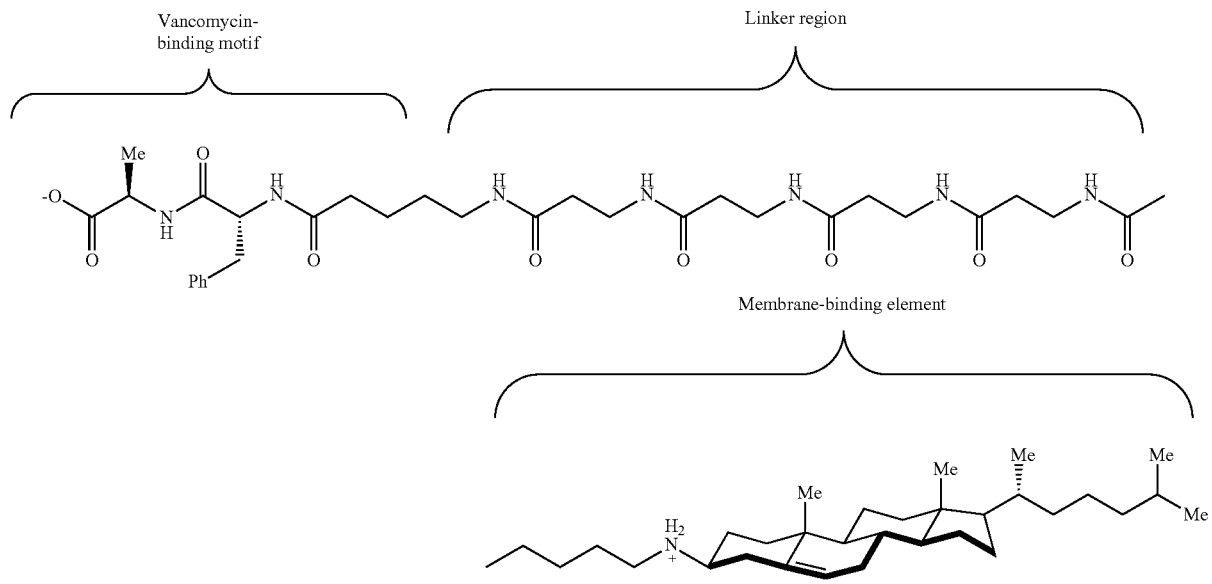

In the embodiment shown above, one aspect of the synthetic drug delivery receptor includes a vancomycin-binding motif as a drug-binding motif. In one aspect, the vancomycin-binding motif is ε-Ahx-D-Phe-D-Ala. In another aspect, the vancomycin-binding motif is D-Ala-D-Ala. In yet another aspect, the vancomycin-binding motif includes D-amino acids.

In another aspect of the present invention, the protein-binding motif of the receptor comprises 2,4-dinitrophenyl (DNP). In yet another embodiment, the protein-binding motif of the receptor comprises 7-nitrobenz-2-oxa-1,3-diazole (NBD) derivatives. Thus, the protein-binding motif of the synthetic receptor may selectively bind almost any desired protein or peptide.

The protein-binding embodiments of the invention include partial or complete amino acid sequences and functional equivalents to such molecules including, but not limited to, polypeptides having conservative and nonconservative amino acid substitutions, mutants and peptidomimetics that resemble these molecules. As used herein, the term "functional equivalents" refers to any modified version of a nucleotide or polypeptide which retains the basic function of its unmodified form. As an example, it is well-known that certain alterations in amino acid or nucleic acid sequences may not affect the polypeptide encoded by that molecule or the function of the polypeptide. It is also possible for deleted versions of a molecule to perform a particular function as well as the original molecule. Even where an alteration does affect whether and to what degree a particular function is performed, such altered molecules are included within the term "functional equivalent" provided that the function of the molecule is not so deleteriously affected as to render the molecule useless for its intended purpose. As used herein, the term "conserved amino acid substitutions" refers to the substitution of one amino acid for another at a given location in the peptide, where the substitution conserves the character of the amino acid residue. In making such changes, substitutions of like amino acid residues can be made on the basis of relative similarity of side-chain substituents, for example, their size, charge, hydrophobicity and hydrophilicity. The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, 1984, Proteins).

In one embodiment of the present invention, the protein-binding motif of the synthetic receptor may be modified to enhance its binding affinity for the cognate protein using standard molecular techniques. See Maniatis and Sambrook et al, In Molecular Cloning: A Laboratory Manual, Cold Spring Harbor, N.Y., 1989. Additionally, methods of preparing the protein-binding embodiments of the invention through chemical synthesis and recombinant techniques are disclosed.

In another aspect of the present invention, the synthetic receptors may be used to construct vaccines. Lipids are often linked to peptides or proteins to create vaccines (see J. Immunol. 2002, 169, 4905-4912). By linking the novel membrane anchors described in this invention to peptides, proteins, lipids, carbohydrates, or nucleic acids, new synthetic vaccines can be constructed. In a preferred embodiment, the novel membrane anchor comprises a derivative of cholesterol, dihydrocholesterol, cholesterylamine, or dihydrocholesterylamine.

B. Synthetic Metal Chelating Receptors In another embodiment, the synthetic receptor of the present invention comprises a synthetic metal chelating receptor. In one aspect, the synthetic metal chelating receptor comprises a metal-binding motif and a membrane-binding element as described above. In one aspect, the synthetic metal chelating receptor comprises a metal-binding motif, a linker region as described above, and a membrane-binding element as described above.

The metal binding motif includes metal chelating groups, for example, nitrilotriacetic acid (NTA), ethylenediaminetetraacetic acid (EDTA), 1,4,7,10-tetraazacyclododecane-1,4,7,10-tetraacetic acid (DOTA), 10-(2-hydroxypropyl)-1,4,7,10-tetraazacyclododecane-1,4,7-triacetic acid (HP-DO3A), and (carboxymethyl)imino]bis(ethyleneitrilo)tetra-acetic acid (DTPA) that bind metal including but not limited to gadolinium, aluminum, lead, titanium, vanadium, chromium, manganese, iron, cobalt, nickel, copper, zinc, yttrium, zirconium, niobium, molybdenum, technetium, ruthenium, rhodium, palladium, silver, cadmium, hafnium, tantalum, tungsten, rhenium, osmium, iridium, platinum, gold, mercury, rutherfordium, dubnium, beryllium, magnesium, calcium, strontium, barium, radium. One embodiment of a synthetic metal chelating receptor is shown below:

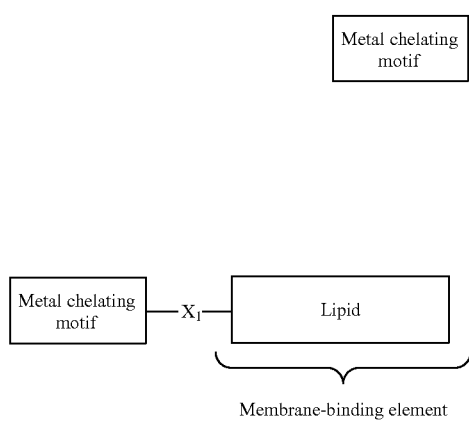

Another embodiment of a synthetic metal chelating receptor is shown below:

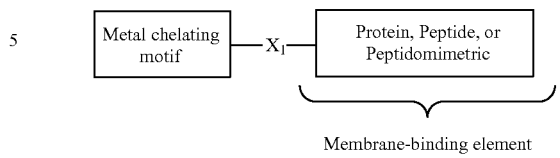

Another embodiment of a synthetic metal chelating receptor is shown below:

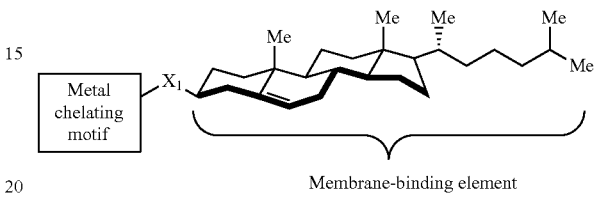

Another embodiment of a synthetic metal chelating receptor is shown below:

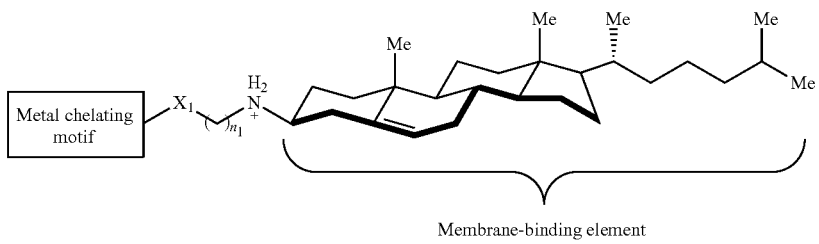

In the embodiment shown above, $n_1$ comprises 0 to 100 or more atoms, $X_1$ comprises one or more linker functional groups such as amines, amides, carbamates, ureas, esters, or ethers. In another aspect, $X_1$ comprises 0 to 100 linker subunits such as alpha, beta, gamma, or delta amino acids as well as aminohexanoic acid and related structures with 0 to 100 or more atoms between the amine and the carboxylic acid.

In the embodiment shown above, one aspect of the synthetic metal-chelating receptor includes a NTA-binding motif as a metal-chelating motif.

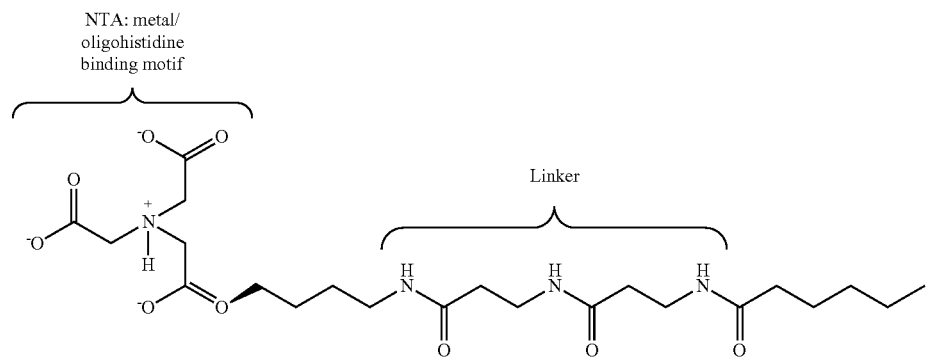

-continued

Membrane-binding element

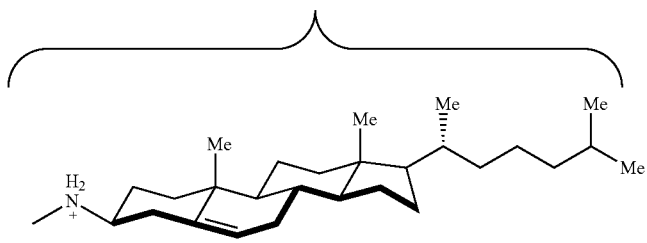

The present inventors contemplate that the synthetic metal chelating receptors may be useful for MRI and other imaging applications. In another aspect of the present invention, synthetic metal chelating receptors may be delivered into a cell population ex vivo/in vitro and injected into a patient or delivered to a cell population in vivo in a patient in need of an MRI. The cell population displaying the synthetic metal chelating receptors or the synthetic metal chelating receptors themselves may be administered a site of interest in the patient, for example, by injection. The synthetic metal chelating receptors may be bound to metal ions prior to administration to the patient or they may bind metal ions in the patient's blood stream or any combination thereof, thereby acting as a MRI contrast agent.

In one aspect, the synthetic metal chelating receptor can be used to reduce the level of iron or other metals in cells in need of such a reduction. In one aspect, the synthetic metal chelating receptor can be used to inhibit tumor cell growth. It is contemplated that the synthetic metal chelating receptor can be used in the treatment and prevention of the following medical conditions including, but are not limited to, cancer, inflammatory and infectious conditions, vasoreactive and vasoocclusive conditions, coronary and peripheral athlerosclerosis, parasitic diseases, neurologic and neuromuscular conditions, and viral conditions including AIDS. Additional medical conditions further include vasospasm, Parkinson's disease, Alzeihmer's disease, malaria, tuberculosis, arthritis, allergic and asthmatic conditions, hepatitis, coronary and peripheral vascular ischemia-reperfusion injury of blood vessels.

C. Synthetic Lipid-Mimicking Receptors

In another embodiment, the synthetic receptor of the present invention comprises synthetic a lipid-mimicking receptor. In one aspect, the synthetic lipid-mimicking receptor comprises a lipid-mimicking motif and a membrane-binding element as described previously. In one aspect, the synthetic lipid-mimicking receptor comprises a lipid-mimicking motif, a linker region as described previously, and a membrane-binding element as described previously.

C-reactive protein (CRP) is a protein that circulates in the human bloodstream and is a non-specific but sensitive marker of the acute inflammatory response. CRP binds to lipids on the surface of dead or dying cells. Normally lipids are packed very tightly on the surface of a cell so that CRP does not have access to bind these extracellular surface lipids. But in dead and dying cells, phosphatidylcholine lipids protrude allowing the CRP to bind to the cell, triggering an immune response. CRP can bind to complement factor C1q and factor H and activate the classic pathway of complement activation. In addition, CRP plays a part in the innate immunity (opsonization) and in the removal of membrane and nuclear material from necrotic cells.

The present inventors have found that when a synthetic lipid-mimicking receptor comprising phosphatidylcholine linked to a membrane-binding element is contacted with cells, the CRP recognizes the cells as dead or dying cells, binds the lipid-mimicking receptor, triggering an immune response, thereby promoting apoptosis of the cell.

The lipid-mimicking motif includes lipids that are found on dead and/or dying cells. For example, the lipid-mimicking motif includes without limitation phosphatidylcholine, phosphatidylserine, and phosphatidylethanolamine or components thereof such as the headgroups phosphocholine, phosphoserine, and phosphoethanolamine. One embodiment of a synthetic lipid-mimicking receptor of the present invention is shown below:

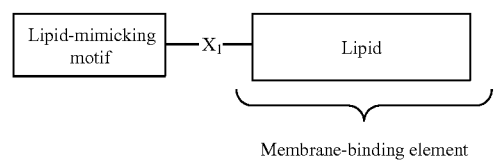

Another embodiment of a synthetic lipid-mimicking receptor of the present invention is shown below:

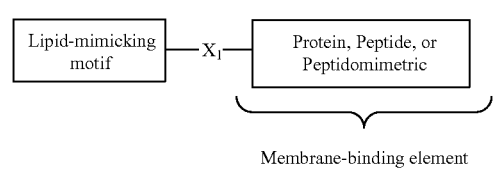

Another embodiment of a synthetic lipid-mimicking receptor of the present invention is shown below:

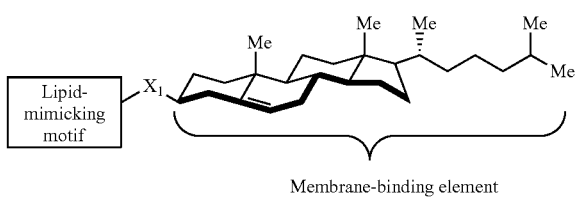

Another embodiment of a synthetic lipid-mimicking receptor of the present invention is shown below:

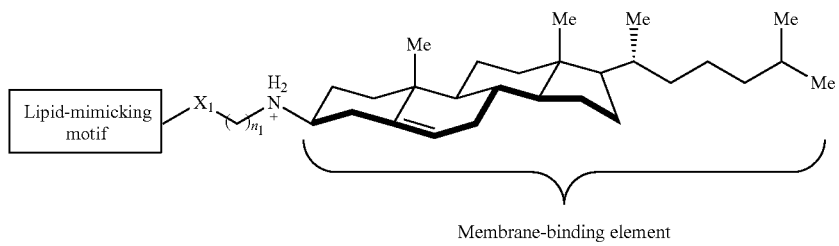

In the embodiment shown above, $n_1$ comprises 0 to 100 or more atoms, $X_1$ comprises one or more linker atoms or functional groups such as amines, amides, carbamates, ureas, esters, or ethers. In another aspect, $X_1$ comprises 0 to 100 linker subunits such as alpha, beta, gamma, or delta amino acids as well as aminohexanoic acid and related structures with 0 to 100 or more atoms between the amine and the carboxylic acid.

One embodiment of a synthetic lipid-mimicking receptor that mimics phosphatidylcholine exposed on the surface of dead or dying cells is shown below:

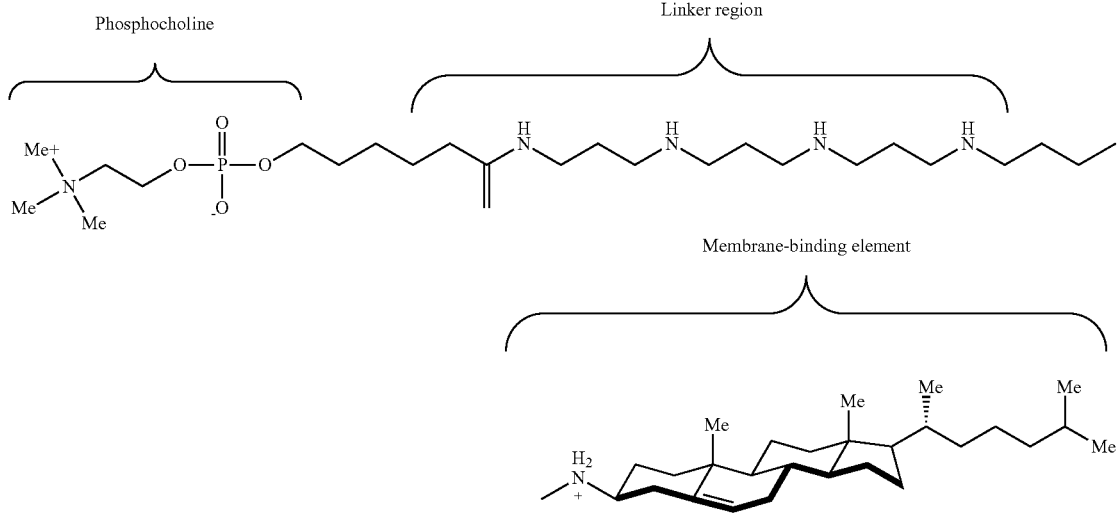

In one aspect, the synthetic lipid-mimicking receptor can be used to induce apoptosis. By mimicking phosphatidylcholine exposed on the surface of dead and dying cells, the synthetic lipid-mimicking receptor that mimics phosphatidylcholine shown above inserted into a cell membrane binds C-reactive protein to induce cellular apoptosis. In one embodiment, the present invention provides a method for stimulating an immune response against cells. As used herein, "stimulating an immune response" means increasing the amount of a component of the immune system or the activity by which a component of the immune system is characterized, increasing the amount of a receptor present on the surface of an immune cell, or increasing the number of immune cells present in the mammal.

In one embodiment, the present invention provides a method for inducing apoptosis by contacting the synthetic lipid-mimicking receptor with a cell. In one aspect, the cell is a tumor cell. By way of example, the following standard techniques can be used to measure the induction of apoptosis caused in a target cell after it is contacted with a synthetic lipid-mimicking receptor of the present invention. For example, apoptosis can be examined or measured in a variety of ways including the detection of morphological indicia of apoptosis (e.g., membrane blebbing, chromatin condensation and fragmentation, and formation of apoptotic bodies), TUNEL (Terminal end-labeling of broken DNA fragments with labeled nucleotides) staining, measuring of DNA laddering, measuring known caspase substrate degradation (e.g., PARP; Taylor et al., J. Neurochem. 68:1598-605, 1997) and counting dying cells, which have become susceptible to dye uptake. Many companies (e.g., Trevigen, Gaithersburg Md., and R&D Systems, Minneapolis Minn.) also supply commercially available kits useful for the measurement of apoptosis by various methods.

The method of contacting the cell with a synthetic lipid-mimicking receptor, the amount of the synthetic lipid-mimicking receptor administered, the appropriate incubation time with the synthetic lipid-mimicking receptor are well known to those of ordinary skill in the art. In addition, known inhibitors of apoptotic pathways, for instance caspase inhibitors, can be used to compare the effectiveness of synthetic lipid-mimicking receptors of this invention. Appropriate inhibitors include viral caspase inhibitors like crmA and baculovirus p35, and peptide-type caspase inhibitors including zVAD-fmk, YVAD- and DEVD-type inhibitors. See Rubin, British Med. Bulle., 53:617-631, 1997.

In another aspect of the present invention, related synthetic receptors incorporating phosphoserine and phosphoethanolamine derivatives can be transported to the inner leaflet of cellular plasma membranes (or displayed on the cell surface, depending on the receptor structure) and by projecting target-binding, chelating, or mimicking groups into the extracellular environment or cellular cytoplasm can be useful for controlling cellular signal transduction, cellular proliferation, and other biological processes.

D. Synthetic Transmembrane Receptors

In another embodiment, the synthetic receptors of the present invention comprise a synthetic transmembrane receptor. In one aspect, the synthetic transmembrane receptor comprises at least two binding motifs and at least two membrane-binding elements. In one embodiment, the synthetic transmembrane receptor comprises a binding motif linked to a first linker region that is in turn linked to a first membrane-binding element. The first membrane-binding element is linked to a second linker region linked to a second membrane-binding element which is linked to a third linker region. The third linker region is linked to a second binding motif.

In one aspect of the invention, the binding motif comprises a small molecule, an oligonucleotide, a carbohydrate, a peptide, or a protein capable of binding noncovalently or covalently linked to a biomolecule, including a small molecule, an oligonucleotide, a carbohydrate, a peptide, a protein, or a drug. In another aspect, the binding motif includes but is not limited to a protein-binding motif, a drug-binding motif, a lipid-binding motif, or a metal-binding motif as described above. Suitable linker regions and membrane-binding elements for use with the synthetic receptors and synthetic transmembrane receptors of the present invention have been described above in detail.

One embodiment of a synthetic transmembrane receptor of the present invention is shown below:

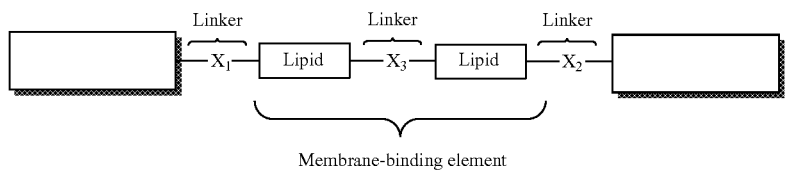

Another embodiment of a synthetic transmembrane receptor of the present invention is shown below:

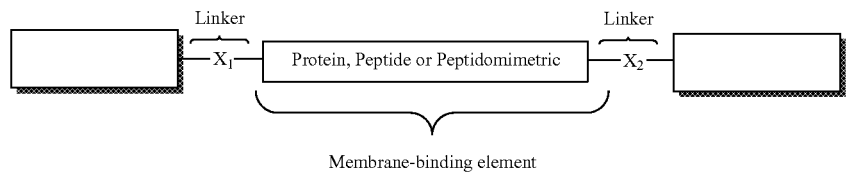

Another embodiment of a synthetic transmembrane receptor of the present invention is shown below:

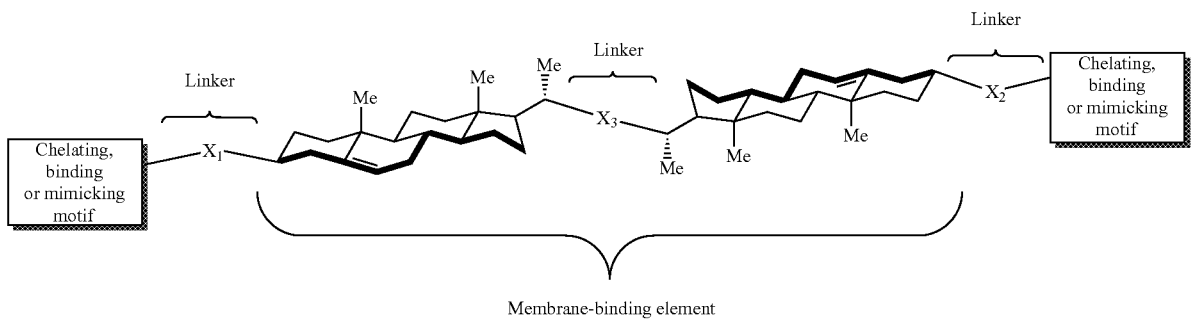

Another embodiment of a synthetic transmembrane receptor of the present invention is shown below:

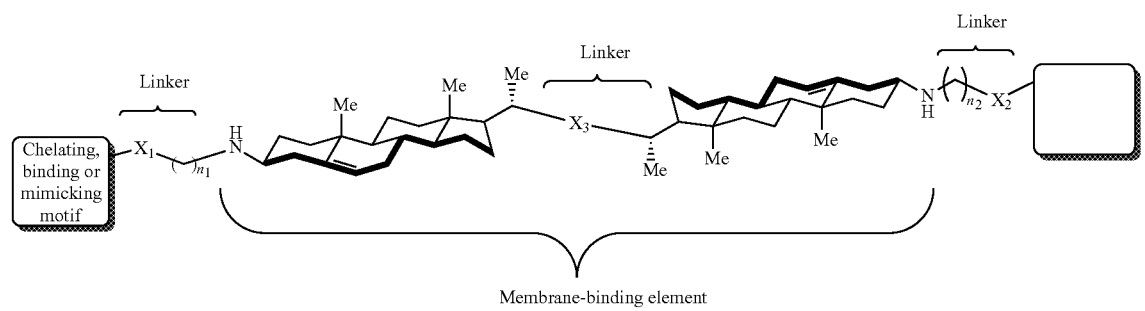

In the embodiments shown above, $n_1$ and $n_2$ comprise 0 to 100 or more atoms, the Linker comprises zero, one, or more linker functional groups such as amines, amides, carbamates, ureas, esters, or ethers. These functional groups can be linear or cyclic. In another aspect, the Lipid region is a natural or nonnatural phospholipid, sphingolipid, or sterol or derivative thereof. In another aspect, $X_1$, $X_2$, or $X_3$ Linker regions comprise 0 to 100 linker subunits such as natural or nonnatural alpha, beta, gamma, or delta amino acids as well as aminohexanoic acid and related structures with 0 to 100 or more atoms between the amine and the carboxylic acid. In another aspect, $X_1$, $X_2$, or $X_3$ Linker regions may comprise a fully saturated alkane of zero to 100 carbon atoms or an alkane of zero to 100 carbon atoms that includes one or more alkene or alkyne functional groups. In another aspect, the linker regions comprise zero, one or more groups selected from the following: alkane, alkene, alkyne, aryl, ketone, amine, amide, ester, ether, urea, carbamate, heterocyclic, and related functional groups in positions $X_1$, $X_2$, or $X_3$. Furthermore, $X_1$, $X_2$, or $X_3$ linker regions may comprise 0 to 100 or more subunits such as alpha, beta, gamma, and delta amino acids as well as aminohexanoic acid and related structures with 0 to 100 or more atoms between the amine and carboxylic acid. These amino acid subunits may also include side-chains such as those found in natural L- and nonnatural D-configuration alpha amino acids or other amino acids.

In one aspect of the synthetic transmembrane receptor, at least one binding motif is located intracellularly. The intracellular binding motif may bind or mimic proteins or or other biomolecules or bind or associate with cytoplasmic domains of other proteins, lipids, carbohydrates, or receptors known to activate various messenger systems. In another aspect of the synthetic transmembrane receptor, at least one binding motif is located extracellularly. The extracellular binding motif as described previously may bind noncovalently or be covalently linked to proteins, drugs, prodrugs, carbohydrates, nucleic acids, lipids or other biomolecules, including those associated with ligand binding and/or signal transduction. The synthetic transmembrane receptor may be part of a protein which is monomeric, homodimeric, heterodimeric, or associated with a larger number of proteins in a non-covalent or disulfide-bonded complex.

These and related synthetic transmembrane receptor span cellular plasma membranes and can bind both extracellular and intracellular biomolecules. The receptors of the present invention can be useful for modifying or mediating cellular signal transduction, proliferation, apoptosis, endocytosis, cellular transfection, and drug delivery. For example, cytotoxic CD8+ T cells (CTLs) which have synthetic transmembrane receptors inserted to their cell membrane where the synthetic transmembrane receptors contain an extracellular binding domain which recognizes specific antigens can be used to augment proliferation and/or killing of infected cells in a variety of viral, and parasitic diseases, where the infected cells express the antigens from the pathogen.

One embodiment of a synthetic transmembrane receptor that binds extracellular antifluorescein antibodies and intracellular streptavidin protein is shown below:

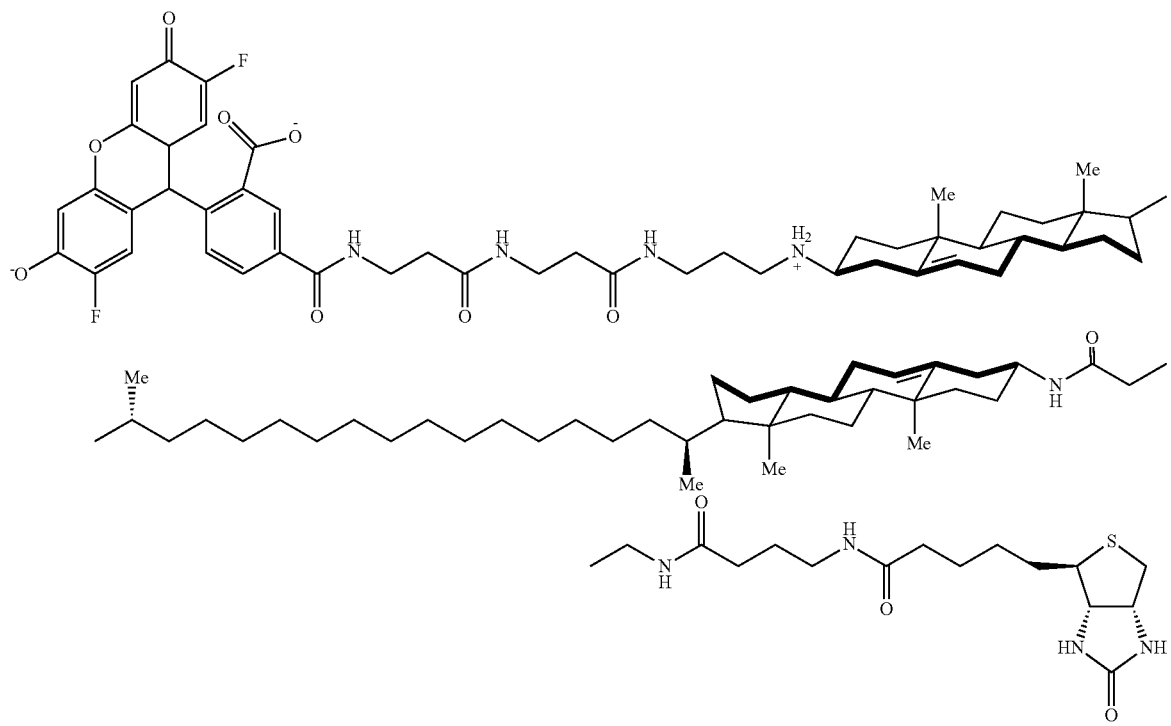

According to the present invention, an unlimited number of differing synthetic receptors can be generated. One skilled in the art would be familiar with standard methods of making a synthetic receptor. For example, the membrane-binding element may be prepared by chemical synthesis. (See E. J. Corey. THE LOGIC OF CHEMICAL SYNTHESIS, Wiley-Interscience, New Ed edition (1995) and K. C. Nicolaou. CLASSICS IN TOTAL SYNTHESIS, Wiley-VCH (1996)) See also Examples section.

The linker region may be prepared using standard techniques known to those skilled in the art or purchased from commercially available sources. See, for example, Thermo Electron Corporation, world wide web at thermo.com. A wide variety of linkers are known in the art for linking two molecules together, particularly, for linking a moiety such as cholesterylamine or its derivative to a peptide, all of which are included within the scope of the present invention. For example, a cholesterylamine membrane-binding element may be synthesized as described above and then a linker added as an intact unit using standard techniques, for example, amide bond formation reactions or the linker may be sequentially added to the membrane-binding element using standard chemical synthesis methods, for example, using protecting groups such as trifluoroacetyl or Fmoc or Boc, and selective deprotection of a protecting group to couple the linker to the membrane-binding element.

Examples of classes of linkers that may be used include but are not limited to amino acids, such as those described in Boonyarattanakalin, S.; Martin, S. E.; Dykstra, S. A.; Peterson, B. R. J. Am. Chem. Soc. 2004, 126, 16379-16386. The determination of an appropriate linker that allows for cycling between the cell surface and the endosomes can be determined using the assays detailed in the present disclosure. In addition, the linkers may influence receptor localization and ligand uptake efficiency which may be determined by performing standard assays including but not limited to fluorescence based assays, microscopy, flow cytometry to measure the amount of the synthetic receptor on the cell surface using an antibody directed against the protein-binding motif or an antibody directed against a protein bound by the synthetic receptor as described in Examples 6 and 22.

The protein-binding domain may be prepared using standard techniques. Appropriate molecular biological techniques may be found in Maniatis and Sambrook et al, In Molecular Cloning: A Laboratory Manual, Cold Spring Harbor, N.Y., 1989. The protein binding domain can be prepared by chemical synthesis methods (such as solid phase peptide synthesis) using techniques known in the art such as those set forth by Merrifield et al., J. Am. Chem. Soc. 85:2149 (1964), Houghten et al., Proc. Natl. Acad. Sci. USA, 82:51:32 (1985), Stewart and Young (Solid phase peptide synthesis, Pierce Chem Co., Rockford, Ill. (1984), and Creighton, 1983, Proteins: Structures and Molecular Principles, W. H. Freeman & Co., N.Y. herein incorporated by reference.

The protein-binding motif can be coupled to the linker using standard techniques, including, for example, standard techniques such as amide bond formation reactions or the linker may be sequentially added to the membrane-binding element using standard chemical synthesis methods, for example, using protecting groups such as trifluoroacetyl or Fmoc or Boc, and selective deprotection of a protecting group, followed by addition of a coupling reagent, to couple the linker to the membrane-binding element.

The present inventors contemplate that the protein-binding motif can bind known binding proteins, such as vancomycin, or used to identify new binding proteins or partners not yet identified. To determine whether a protein binds the protein binding motif of the synthetic receptor, the synthetic receptor is allowed to contact the cell surface of a cell and fluorescence based assays or functional assays are used to detect proteins that bind to the protein-binding motif of the synthetic receptor inserted into the cell's membrane. See Examples 6 and 22. Protein-protein interactions between a protein and the protein binding motif of the synthetic receptor can be determined using two-hybrid systems (Field & Song, Nature 340:245-246 (1989); Chien et al., Proc. Natl. Acad. Sci. USA 88:9578-9582 (1991); and Young K H, Biol. Reprod. 58:302-311 (1998), GST/HIS pull down assays, mutant operators (Granger et al., WO 98/01879) and the like (See also Mathis G., Clin. Chem. 41:139-147 (1995); Lam K. S. Anticancer Drug Res., 12:145-167 (1997); and Phizicky et al., Microbiol. Rev. 59:94-123 (1995).

Several embodiments of the invention have biotechnological, diagnostic, and therapeutic use. When the receptors of the present invention are contacted with living mammalian cells, these receptors insert in the cellular plasma membrane, project the protein-binding motifs from the cell surface, bind the proteins and internalize them through endocytosis. As used herein, the various forms of the term "contact", "contacting", "contacted", etc. (i.e., contacting a synthetic receptor with a cell) is intended to include incubating the synthetic receptor and the cell together in vitro (e.g., adding the synthetic receptor to cells in culture) and administering the agent to a subject such that the synthetic receptor and cells of the subject are contacted in vivo. Any suitable method of contacting the synthetic receptor with cells may be used.

The present invention also provides a method for delivering a protein, peptide, small molecule into a cell. As used herein, the term "delivering" refers includes but is not limited to causing the protein to enter the cell. In one aspect of the invention, the method comprises contacting the synthetic receptors with the target cells. "Target cells" according to the invention is understood to include, without limitation, bacterial, fungal, plant, insect, avian, reptilian, amphibian, and mammalian cells, including human or animal cells.

Any suitable duration of growth of the target cells of contacting of the target cells with a synthetic receptor may be used in the present invention. There are no particular limitations to the different conditions in the culturing of the target cells and the methods that are ordinarily used may be carried out, where bacterial, fungal, plant, insect, avian, reptilian, amphibian, and mammalian cells are cultured in suitable media. General growth conditions for culturing the particular cells may be obtained from texts known in the art such as Bergey's Manual of Systematic Bacteriology, Vol. 1, Williams and Wilkins, Baltimore/London (1984), N. R. Krieg, ed.; R. Ian Freshney. Culture of Animal Cells: A Manual of Basic Technique, 4th Edition Wiley-Liss; 4 edition (2000); Victor Vinci. Handbook of Industrial Cell Culture: Mammalian, Microbial, and Plant Cells. Humana Press (2003); The Mycota: A Comprehensive Treatise on Fungi as Experimental Systems for Basic and Applied Research, Volume VIII: Biology of the Fungal Cell. Springer; first edition (2001); Insect Cell Culture Engineering (Biotechnology and Bioprocessing Series). Marcel Dekker. (1993). The introduction of the protein may be confirmed by any means known to one skilled in the art, including for example, immunofluorescence microscopy, confocal laser scanning microscopy, flow cytometry, and ELISA assays.

Among the effects observed from the present invention is the synthetic cell surface receptors' stability, dynamic cycling between the plasma membrane and intracellular endosomes, targeting of ligands to proposed cholesterol and sphingolipid-enriched lipid raft membrane microdomains, and delivery of protein or drug ligands to late endosomes/lysosomes. Therefore, the synthetic receptors with modified linker regions have potential as cellular probes, as they confer dramatic differences in subcellular localization, and would provide useful as probes for cellular mechanisms that regulate the segregation, localization, and sorting of membrane-associated biomolecules.

Experiments have been performed wherein a fluorescent analog of a synthetic receptor was administered to a cell, a cell population, or animal, the insertion of the receptor was detected by excitation/emission spectra of the fluorophore. Thus, in one embodiment of the present invention, the synthetic receptor conjugated to a label or tag with or without the linker region described previously or constructed as a tagged small molecule, fusion protein, peptide, nucleic acid, or carbohydrate can also be utilized as a tool for visualizing cellular or subcellular localization, such as labeling of the cellular plasma membrane, endosomes, or other subcellular compartments, and protein trafficking or cycling from the cell surface to the endosome. The synthetic receptor conjugated to a fluorophore or otherwise tagged or labeled or a synthetic receptor analog can also be used to track or analyze cells in vitro or in vivo. For example, synthetic receptors conjugated to a fluorophore such as fluorescein or fluorescein analogues may be added to cells ex vivo and administered to a recipient. In such experiments, synthetic receptor conjugated to a fluorophore can be inserted into a cell or cell population and detected using standard techniques known to one skilled in the art, including for example, flow cytometry, fluorescence activated cell sorting, fluorescence microscopy, and other histological methods.

In another aspect, the synthetic receptors can be labeled with a detectable moiety. Detection of a synthetic receptor of the present invention can be facilitated by coupling (i.e., physically linking) the synthetic receptor to a detectable moiety. Examples of detectable moieties include various enzymes, prosthetic groups, fluorescent materials, luminescent materials, bioluminescent materials, and radioactive materials. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $I^{125}$, $I^{131}$, $S^{35}$ or $H^3$. The detectable moiety should be capable of producing, either directly or indirectly, a detectable signal. Any method known in the art for conjugating the synthetic receptor to the detectable moiety may be employed, including those methods described by Hunter et al., *Nature*, 144:945 (1962); David et al., *Biochemistry*, 13:1014 (1974); Pain et al., *J. Immunol. Meth.*, 40:219 (1981); and Nygren, *J. Histochem. and Cytochem.*, 30:407 (1982).

In one embodiment of the invention, the synthetic receptor comprises a tag polypeptide which provides an epitope to which an anti-tag antibody can selectively bind. The epitope tag may be placed at the amino- or carboxyl-terminus of the synthetic receptor. The presence of such epitope-tagged forms of the synthetic receptor can be detected using an antibody against the tag polypeptide. Also, provision of the epitope tag enables the synthetic receptor to be readily purified by affinity purification using an anti-tag antibody or another type of affinity matrix that binds to the epitope tag. Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., *Mol. Cell. Biol.*, 8:2159-2165 (1988)]; the c-myc tag and the 8F9, 3C7, 6E10, G4, B7 and 9E10 antibodies thereto [Evan et al., *Molecular and Cellular Biology*, 5:3610-3616 (1985)]; and the Herpes Simplex virus glycoprotein D (gD) tag and its antibody [Paborsky et al., *Protein Engineering*, 3(6):547-553 (1990)]. Other tag polypeptides include the Flag-peptide [Hopp et al., *BioTechnology*, 6:1204-1210 (1988)]; the KT3 epitope peptide [Martin et al., *Science*, 255:192-194 (1992)]; an α-tubulin epitope peptide [Skinner et al., *J. Biol. Chem.*, 266:15163-15166 (1991)]; and the T7 gene 10 protein peptide tag [Lutz-Freyermuth et al., *Proc. Natl. Acad. Sci. USA*, 87:6393-6397 (1990)].

Thus, another aspect of the present invention, synthetic cellular receptors may be used as mechanistic probes. In one aspect, the probe is a fluorescent analog of a synthetic receptor. These fluorescent analogs may contain diverse fluorophores, including for example, without limitation, NBD, fluorescein and its derivatives, for example, the red-shifted hexachlorofluorescein, texas red, rhodamine, coumarin derivatives, Cy3, AlexaFluor dyes, and fluorescent quantum dots.

The invention also relates to a method for delivering in vitro, ex vivo or in vivo at least one protein into target cells according to which the cell is brought into contact with a synthetic receptor bound to a protein according to the invention.

In another embodiment, the present invention provides a method of treating a disease, disorder, or condition comprising administering a therapeutically effective amount of a protein into a target cell using a synthetic cell receptor to a subject in need thereof. The synthetic receptor for delivering a protein into a cell comprises a protein-binding motif and a membrane-binding element. The membrane-binding element may include, for example, cholesterylamine, dihydrocholesterylamine, ergosterylamine, derivatives of cholesterylamine, dihydrocholesterylamine, ergosterylamine and related compounds thereof wherein the element anchors the receptor into a cell plasma membrane. As used herein, "therapeutically effective amount" refers to an amount that is effective in reducing, eliminating, treating, preventing or controlling the symptoms of diseases and conditions. The term "controlling" is intended to refer to all processes wherein there may be a slowing, interrupting, arresting, or stopping of the progression of the diseases and conditions described herein, but does not necessarily indicate a total elimination of all disease and condition symptoms, and is intended to include prophylactic treatment. In another embodiment, the method additionally comprises a synthetic receptor as described above and pharmaceutically acceptable carrier. Pharmaceutically acceptable carriers are generally added that are compatible with the active ingredients and acceptable for pharmaceutical use. Combinations of carriers may also be used. Pharmaceutically acceptable carriers include but are not limited to cyclodextrins, Low-Density Lipoprotein (LDL), and High-Density Lipoprotein (HDL). One of ordinary skill in the art would be familiar with pharmaceutically acceptable carriers and it is described, by way of example, in Remington's Pharmaceutical Sciences, 18th Edition, Mack Publishing Company, Pennsylvania, USA. Except insofar as any conventional media or agent is incompatible with the active ingredient, use thereof in the pharmaceutical compositions of the present invention is contemplated.

In one aspect, a pharmaceutical composition for treating a disease, disorder, or condition comprises a pharmaceutically acceptable carrier and a synthetic cell receptor for delivering a protein into a cell where the receptor comprises a protein- or target-binding motif and a membrane-binding element. The membrane-binding element may include cholesterylamine, dihydrocholesterylamine, ergosterylamine, derivatives of cholesterylamine, dihydrocholesterylamine, ergosterylamine and related compounds thereof to anchor into a cell plasma membrane. In one aspect of the present invention, the synthetic receptor bound to a protein according to the invention can be used to treat a disease, disorder, or condition, or as a prophylactic. Accordingly, the subject of the invention may be used in enzyme replacement therapy or to treat a variety of diseases, disorders, or conditions, including without limitation, viral, yeast, and bacterial infections, cancer, inflammation, and autoimmune diseases. In one aspect of the invention, the synthetic receptors may be used to deliver an enzyme to a cell in need of the enzyme replacement therapy. As used herein, unless otherwise defined in conjunction with specific diseases or disorders, the term "treating" refers to: (i) preventing a disease, disorder or condition from occurring in an animal or human that may be predisposed to the disease, disorder and/or condition but has not yet been diagnosed as having it; (ii) inhibiting the disease, disorder or condition, i.e., arresting its development; and/or (iii) relieving the disease, disorder or condition, i.e., causing regression of the disease, disorder and/or condition.

In another aspect of the current invention, synthetic receptors may be employed to deliver proteins, peptides, or small molecules that inhibit viruses that replicate in the cytoplasm. These proteins include, for example, nucleic acid aptamers or antibodies that bind proteins important in viral life cycles. Examples of viruses that replicate in the cytoplasm belong to the families: Picornaviridae, Caliciviridae, Togaviridae, Flaviviridae, Coronaviridae, Paramyxoviridae, Reoviridae, Bunyaviridae, Arenaviridae, Paramyxoviridae, Rhabdoviridae, Poxviridae, and Hepadnaviridae. This is important since many viruses do not have vaccines to provide immunity. Thus, the present invention offers new prospects for applications as tools for drug delivery.

Over time, many strains of gram-positive bacteria, such as *Staphylococcus aureus*, have evolved to become resistant to virtually all antibiotics. Often times, when no other antibiotic is effective in killing bacterial pathogens, physicians turn to vancomycin, described as the drug of "last resort." A further impediment is that many antibiotics do not effectively permeate the cell's plasma membranes to reach its pathogenic target.

Remarkably, the present inventors have found a method for treating microbes that elude antibiotics and related glycopeptide antibiotics administered in a traditional manner. For example, *Listeria moncytogenes* (*L. monocytogenes*), a potentially fatal food-borne pathogen, eludes the antimicrobial activity of glycopeptide antibiotics by replicating in the cytoplasm of the mammalian cells. The present inventors have found that the present invention may be used to deliver vancomycin, a glycopeptide antibiotic, and/or other related glycopeptide antibiotics into the cytoplasm of cells infected with *L. moncytogenes*. As a control, the present inventors treated non-infected mammalian cells with a synthetic receptor containing an enhanced vancomycin-binding motif linked to 3β-cholesterylamine. The synthetic receptor bound the vancomycin derivative, underwent endocytosis, released the vancomycin derivative in the endosome/lysosome where it was degraded, allowing the synthetic receptor to recycle to the cell surface to recommence the delivery process. Thus, in one aspect of the present invention, once the protein-bound synthetic receptor has entered the cell, the endosome/lysosome in particular, the protein is released from the synthetic receptor.

However, in cells infected with *L. moncytogenes*, the pathogen secretes membrane-disruptive proteins that disrupt the integrity of the endosome so that the pathogen can escape from the endosome and replicate in the cytoplasm. The present invention capitalizes on this event so that when the synthetic receptor bound with vancomycin undergoes endocytosis, the vancomycin is delivered to the endosome, but escapes into the cytoplasm using the same route that the pathogen created. In this way, the antibiotic is able to encounter and bind *L. monocytogenes*, inhibiting the construction of the bacterial cell walls. Therefore, in another aspect, once the protein-bound synthetic receptor has entered the cell, the protein is released from the synthetic receptor and may enter the cytoplasm. The receptor is then free to recycle to the cell surface for additional rounds of delivery. Therefore, in one aspect of the present invention, the synthetic receptors have bacteriocidal or bacteriostatic effects as shown in viability assays. Examples 15-19.

Accordingly, these synthetic receptors with modified linker regions have unlimited potential to treat bacteria and viruses. As described, the present inventors have identified a composition and method that effectively enhances the delivery of poorly permeable antibiotics, such as vancomycin or teicoplanin, to cells. This invention will provide an effective tool for the war on drug-resistant bacteria. Once internalized, the drug can accumulate within the cells where it has a therapeutic effect. Not only does the current invention deliver an antibiotic to the pathogenic replicative source but also does so in an efficient manner using any "custom-designed" binding motif. For example, in one embodiment of the present invention, the synthetic receptor contains an enhanced binding motif for vancomycin, resulting in improved affinity for the antibiotic.

In one aspect of the invention, a synthetic receptor having an ergosterol-derived membrane-binding element can be used to treat bacteria or yeast infections in a subject. In one aspect, the method comprises contacting a synthetic receptor with yeast or bacterial cells in vitro or in vivo, causing the synthetic receptor to insert into the cells' membranes, so that the yeast or bacterial cells displaying the synthetic receptors in vivo, for example, in a mammal, would be recognized as foreign by the mammal's immune system and destroyed. In another aspect, a synthetic receptor having an ergosterol-derived or brassicasterol-derived membrane-binding element can be used as probe in avian, reptilian, amphibian, insect, yeast, bacterial, or plant cells.

In still another aspect of the present invention, synthetic receptors may be used to modulate therapeutically important extracellular ligands. These ligands include but are not limited to cytokines, growth factors, hormones, antibodies, and angiogenic factors. These ligands are secreted by a number of cells and act through cell surface receptors to elicit biochemical responses in their target cells, such as cell differentiation and proliferation. The present invention contemplates the removal of extra-cellular ligands from circulation in physiological fluids, including, for example, blood, using synthetic receptors.

Receptors displaying the desired ligand-binding motif would bind the cognate ligand, deliver the ligand to the endosome, where it would be released and degraded. The receptor would then be recycled back to the surface to bind and remove more ligands from circulation. This has been demonstrated by removal of antibodies from cell culture media using synthetic receptors bearing antibody-binding motifs. Therefore, use of the present invention to remove targeted ligands from circulation would allow for the modulation of the immune response, cellular proliferation such as cancer proliferation, or cellular differentiation. As used herein, the various forms of the term "modulating of the immune response" means increasing or decreasing either the amount of a component of the immune system or the activity by which a component of the immune system is characterized, increasing or decreasing the amount of receptor present on the surface of an immune cell, or increasing or decreasing the number of immune cells present in the mammal. In the context of the use of a method of treatment in vivo according to the present invention, it is, in addition, a treatment designed deplete a patient of a particular protein.

In another aspect of the present invention, the synthetic receptors may be used to treat cancer. Many tumor cells do not express the necessary cell surface receptor to "take in" anti-cancer drugs or express the cell surface receptor at insufficient levels. However, by using the present invention, the drug can still be delivered. For example, cancer cells may become resistant to methotrexate by stopping production of the folate receptors. Thus, according to the present invention synthetic folate receptors can be expressed on the surface of tumor cells. The protein-binding motif of the synthetic folate receptor can then bind the anti-cancer drug methotrexate and undergo receptor-mediated endocytosis, thereby inhibiting the enzyme dihydrofolate reductase.

Another embodiment of the present invention includes receptors containing calixarenes as protein-binding motifs. Calixarenes can be prepared by those skilled in the art to bind the vascular epidermal growth factor (VEGF), platelet-derived growth factor (PDGF), and other proteins. These compounds could be used to remove these and related cancer-promoting growth factors from circulation to stop tumor growth or conversely could be used to activate receptors for these proteins by promoting the association of growth factors with cell surfaces.

Another embodiment of the present invention includes synthetic receptors containing cyclic peptides as protein binding motifs. Cyclic peptides can be prepared by those skilled in the art to bind immunoglobulins and other proteins. This would allow for modulation the immune system by promoting the endocytic destruction of antibodies such as antibodies involved in autoimmune diseases such as lupus and pemphigus. For example, cysteine-disulfide constrained cyclic peptides containing the sequence DCAWHLGELVWCT exhibit high affinity for the hinge region of human immunoglobulins. Other cyclic peptides can be identified by techniques such as phage display that bind to specific proteins.

The effective dose and method of administration of a particular synthetic receptor thereof can vary based on the individual needs of the patient and the treatment or preventative measure sought. Therapeutic efficacy and toxicity of such compounds can be determined by standard pharmaceutical procedures in cell cultures or experimental animals, e.g., ED50 (the dose therapeutically effective in 50% of the population). For example, the synthetic receptors discussed above, can be administered to the mice and the effect on certain tissues or cells can be determined using histology, flow cytometry, ELISA and other assays. The data obtained from these assays is then used in formulating a range of dosage for use with other organisms, including humans. The dosage varies within this range depending upon type of synthetic receptor or binding protein, the dosage form employed, sensitivity of the organism, and the route of administration.

Normal dosage amounts of various synthetic receptors can vary from approximately 1 to 100,000 micrograms, up to a total dose of about 10 grams, depending upon the route of administration. A constant infusion of the synthetic receptors can also be provided so as to maintain a stable concentration in the tissues as measured by blood levels.

The exact dosage is chosen by the individual physician in view of the patient to be treated. Dosage and administration are adjusted to provide sufficient levels of the active moiety or to maintain the desired effect. Additional factors that can be taken into account include the severity of the disease, age of the organism, and weight or size of the organism; diet, time and frequency of administration, drug combination(s), reaction sensitivities, and tolerance/response to therapy. Synthetic receptors may be administered hourly, daily, weekly, monthly or as needed. Routes of administration of the synthetic receptors of the invention include, but are not limited to, topical, transdermal, parenteral, gastrointestinal, transbronchial, and transalveolar. Transdermal administration is accomplished by application of a cream, rinse, gel, etc. capable of allowing the pharmacologically active compounds to penetrate the skin. Parenteral routes of administration include, but are not limited to, electrical or direct injection such as direct injection into a central venous line, intravenous, intramuscular, intraperitoneal, intradermal, or subcutaneous injection. Gastrointestinal routes of administration include, but are not limited to, ingestion and rectal. Transbronchial and transalveolar routes of administration include, but are not limited to, inhalation, either via the mouth or intranasally.

Synthetic receptors of this invention that are suitable for transdermal or topical administration include, but are not limited to, pharmaceutically acceptable suspensions, oils, creams, and ointments applied directly to the skin or incorporated into a protective carrier such as a transdermal device ("transdermal patch"). Examples of suitable creams, ointments, etc. can be found, for instance, in the Physician's Desk Reference. Examples of suitable transdermal devices are described, for instance, in U.S. Pat. No. 4,818,540 issued Apr. 4, 1989 to Chinen, et al., herein incorporated by reference.

Synthetic receptors of this invention that are suitable for parenteral administration include, but are not limited to, pharmaceutically acceptable sterile isotonic solutions. Such solutions include, but are not limited to, saline and phosphate buffered saline for injection into a central venous line, intravenous, intramuscular, intraperitoneal, intradermal, or subcutaneous injection.

Synthetic receptors of this invention that are suitable for transbronchial and transalveolar administration include, but not limited to, various types of aerosols for inhalation. Devices suitable for transbronchial and transalveolar administration of these are also embodiments. Such devices include, but are not limited to, atomizers and vaporizers. Many forms of currently available atomizers and vaporizers can be readily adapted to deliver compositions having the pharmacologically active compounds of the invention.

Synthetic receptors of this invention that are suitable for gastrointestinal administration include, but not limited to, pharmaceutically acceptable powders, pills or liquids for ingestion and suppositories for rectal administration. Once the synthetic receptors has been obtained, it can be administered to a organism in need to treat or prevent a disease, disorder, or condition.

The synthetic receptors according to the present invention can be administered orally, by subcutaneous or other injection, intravenously, intracerebrally, intramuscularly, parenternally, transdermally, nasally or rectally. The appropriate route of administration and dosage vary according to various parameters, for example the individual or disease to be treated or alternatively the polynucleotide to be transferred. The form in which the synthetic receptors is administered depends at least in part on the route by which the synthetic receptors is administered.

While the present invention is disclosed with reference to embodiments and examples detailed above, it is to be understood that these examples are intended in an illustrative rather than limiting sense, as it is contemplated that modifications will readily occur to those skilled in the art, which modifications will be within the spirit of the invention and the scope of the appended claims. The references cited in this application are incorporated herein in their entirety.

Example 1

Design and Synthesis of Receptors for Anti-DNP IgG Ligands

The numbered receptors in examples 1-14 refer to those shown in FIGS. 1-13 and in examples 1-14. Synthetic receptors were designed that incorporate 2,4-dinitrophenyl (DNP) and structurally similar green fluorescent 7-nitrobenz-2-oxa-1,3-diazole (NBD) headgroups. These headgroups were linked to N-alkyl and N-acyl derivatives of 3β-cholesterylamine via tethers containing 6-aminohexanoic acid and β-alanine subunits as seen in FIG. 1.

Example 2

Fluorescent Polarization Assays to Determine Binding Affinity Between the Headgroups and its Ligand The affinity of DNP and NBD headgroups affinity for rabbit polyclonal anti-DNP IgG were evaluated using fluorescent derivatives. Both DNP and fluorescent NBD derivatives bound tightly to this IgG with dissociation constants ($K_d$) values of 23±1.5 nM(DNP) and 820±144 nM.

Example 3

Scheme Showing the Synthesis of 3Beta-Cholesterylamine and Derivatives from Cholesterol

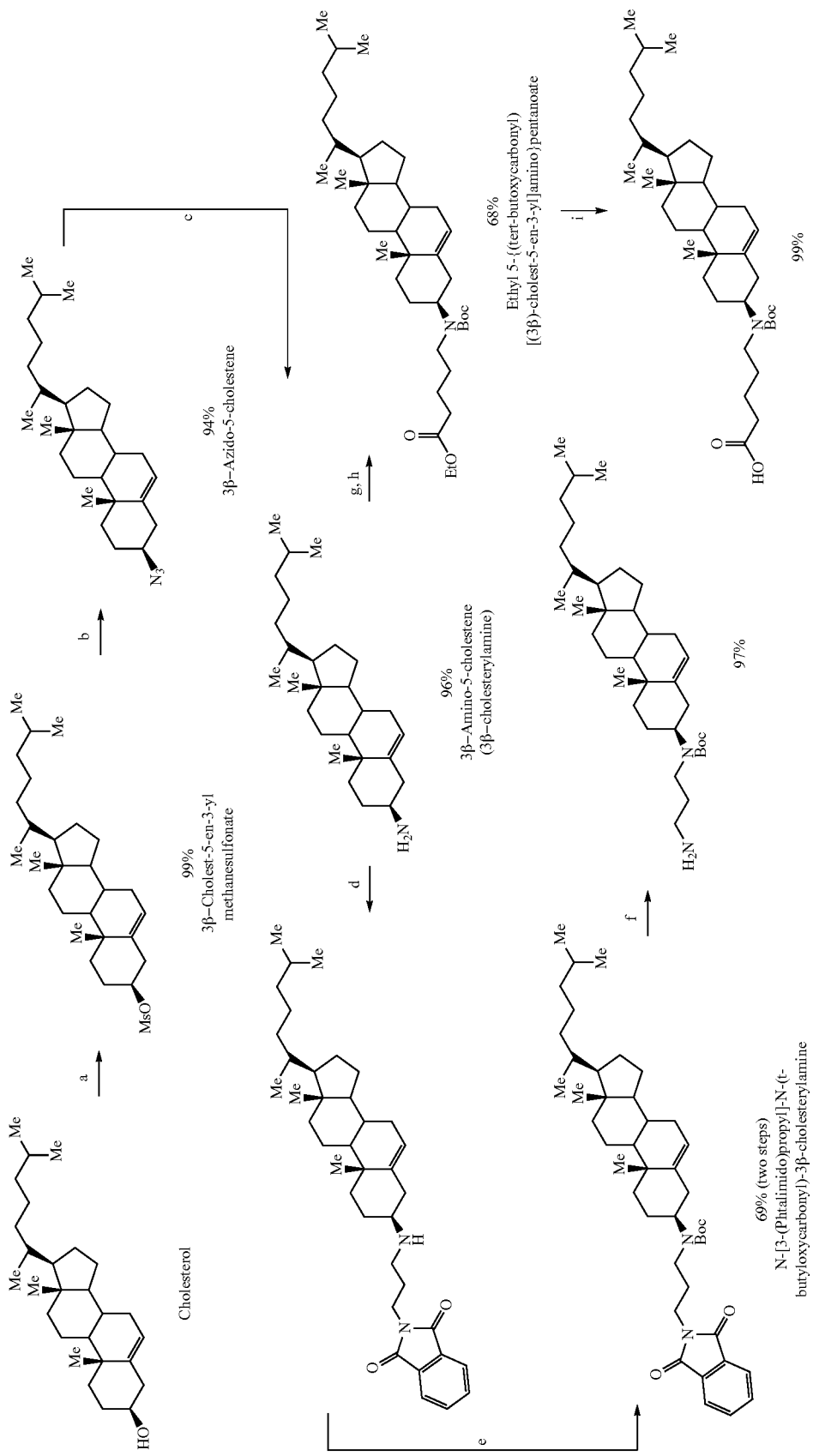

The schematic of example 3 is illustrated above and conveys to one of ordinary skill in the art the process. In word terms, it is as follows:

The present inventors have discovered a novel method for synthesis of 3beta-azido-5-cholestene by Vorbruggen-type coupling of electrophilic cholesterol derivatives (shown as step b in the above scheme). In one aspect, the method for synthesis of 3beta-Azido-5-cholestene by Vorbruggen-type coupling of electrophilic cholesterol derivatives comprises reacting cholesterol or a cholesterol bearing a leaving group at the 3-position, for example, cholesterol triflate, cholesterol mesylate, cholesterol tosylate or cholesteryl esters, with a Lewis acid, for example, boron trifluoride etherate, in the presence of an azide, for example, a silyl azide such as trimethylsilyl azide, at a temperature between minus 150° C. to plus 200° C. and a Lewis acid catalyst to obtain a reaction mixture containing 3beta-azido-5-cholestene.

As used herein, the term "azide" refers to any compound or derivative having the $N_3^-$; moiety therein, including azide derivatives or salts thereof. The azide can be a metal azide wherein the metal is an alkali metal such as potassium, sodium, lithium, rubidium or cesium. The metal can be a transition metal such as, but not limited to, iron, cobalt, nickel, copper or zinc. The azide of the present invention can also be an organic azide or ammonium azide. The present inventors contemplate that other Lewis acids may be used in these synthesis methods, including, without limitation, boron trifluoride, tin tetrachloride, aluminum trichloride, titanium tetrachloride or trimethylsilyl triflate, BBr3, SnCl4, ZnCl2, MgCl2, or MgBr2 Et2O or any salt thereof.

The present inventors have discovered a novel method for synthesis of N-[3-(phthalimido)propyl]-N-cholesterylamine by SN2 reaction of cholesterylamine with an electrophile (shown as step d in the above scheme). In one aspect, the method for synthesis of N-[3-(phthalimido)propyl]-N-cholesterylamine by SN2 reaction of cholesterylamine with an electrophile comprises reacting cholesterylamine with 3-bromopropyl phthalimide, $K_2CO_3$, and DMF at a temperature between −78° C. and 250° C.

The present inventors have discovered a novel method for synthesis of N-[3-(phthalimido)propyl]-N-(t-butyloxycarbonyl)-3β-cholesterylamine by nucleophilic acyl substitution of N-[3-(phthalimido)propyl]-3β-cholesterylamine (shown as step e in the above scheme). In one aspect, the method for synthesis of N-[3-(phthalimido)propyl]-N-(t-butyloxycarbonyl)-cholesterylamine by nucleophilic acyl substitution of N-[3-(phthalimido)propyl]-N-cholesterylamine comprises reacting N-[3-(phthalimido)propyl]-N-cholesterylamine with (Boc)2O, DIEA, $CH_2Cl_2$.

The present inventors have discovered a novel method for synthesis of ethyl 5-{(tert-butoxycarbonyl)[(3beta)-cholest-5-en-3-yl]amino}pentanoate (3). In one aspect, the method for synthesis of ethyl 5-{(tert-butoxycarbonyl)[(3beta)-cholest-5-en-3-yl]amino}pentanoate comprises adding to DMF (10 mL) 3β-amino-5-cholestene (2, 386 mg, 1.0 mmol), ethyl 5-bromovalerate (174 microL, 1.1 mmol) and K2CO3 (276 mg, 2.0 mmol), heating the solution to 60° C., stirring the solution for 24 hours, cooling the reaction to 23° C., removing the DMF in vacuo to generate a solid residue, adding $CH_2Cl_2$ (10 mL) to the resulting solid residue, removing insoluble salts from residue by filtration, and washing the solids with additional $CH_2Cl_2$ (5 mL) to generate a solution containing the crude secondary amine product, added (Boc) 2O (327 mg, 1.5 mmol) and DIEA (0.5 mL, 3.0 mmol) to the solution, stirring the reaction for 3 hours at 23° C., concentrating the reaction in vacuo, using Flash column chromatography (hexanes/ethyl acetate, 10:1) to obtain 3 (417 mg, 68%) as a white solid. (See Example 17 of the present disclosure).

The present inventors contemplate that other Lewis acids may be used in these synthesis methods, including, without limitation, boron trifluoride, tin tetrachloride, aluminum trichloride, titanium tetrachloride or trimethylsilyl triflate, BBr3, SnCl4, ZnCl2, MgCl2, or MgBr2 Et2O. Based upon the present disclosure including the schemes and methods provided above, those skilled in the art would understand how to modify any part of these methods of synthesizing these compounds under various conditions and concentrations to achieve the desired result, including the use of or substitution of other solvents, bases, and lewis acids in these reactions.

Example 4

Construction of Synthetic Receptors

Various synthetic receptors were constructed by modifying a 3β-cholesterylamine as shown in Example 3 above. Cholesterol may alternatively be modified to become a nosyl-protected 3β-cholesterylamine via a Swern oxidation, reduction to epicholesterol, and synthesis of 3beta-azido-5-cholestene via Mitsunobu reaction with hydrazoic acid. The compound underwent further modification to become a receptor by reduction, protection as a nosyl sulfonamide, and use of Fukuyama's amine synthesis methodology and/or deprotection and sequential amide bond formation reactions.

Example 5

General

Chemical reagents were obtained from Acros, Aldrich, Alfa Aesar, or TCI America. Solvents were from EM Science. Media and antibiotics were purchased from Gibco BRL. Cholera toxin B subunit-Alexa Fluor 488 (CT-B-AF488), Transferrin-Alexa Fluor-488, Protein A Alexa Fluor 488 (PrA-AF488), Protein A Alexa Fluor 594 (PrA-AF594), Protein A Alexa Fluor 633 (PrA-AF633), and BODIPY TR ceramide were from Molecular Probes. Rabbit polyclonal anti-dinitrophenyl (anti-DNP) IgG was from Sigma. Commercial grade reagents were used without further purification unless otherwise noted. Tetrahydrofuran and diethyl ether were distilled from sodium benzophenone ketyl under nitrogen. Dichloromethane was distilled from calcium hydride under nitrogen. N,N-Dimethylformamide was from a freshly-opened bottle. All reactions were performed under an atmosphere of dry argon. Reactions were monitored by analytical thin-layer chromatography on plates coated with 0.25 mm silica gel 60 $F_{254}$ (EM Science). TLC plates were visualized by UV irradiation (254 nm) or stained with a solution of phosphomolybdic acid and sulfuric acid in ethanol (1:1:20). Flash column chromatography employed ICN SiliTech Silica Gel (32-63 μm). Purification by preparative reverse phase HPLC employed an Agilent 1100 preparative pump/gradient extension instrument equipped with a Hamilton PRP-1 (polystyrene-divinylbenzene) reverse phase column (7 μm particle size, 21.5 mm×25 cm). The HPLC flow rate was increased from 10 mL/min (t=0 min) to 20 mL/min (t=1 min) and maintained at 20 mL/min for the remainder of the run unless otherwise noted. Melting points were measured with a Thomas Hoover capillary melting point apparatus and are uncorrected. Infrared spectra were obtained with a Perkin Elmer 1600 Series FTIR. NMR spectra were obtained with Bruker AMX-360, DRX-400, or AMX-2-500 instruments with chemical shifts reported in parts per million (ppm, δ) referenced to either CDCl$_3$ ($^1$H 7.27 ppm; $^{13}$C 77.23 ppm), DMSO-d$_6$ ($^1$H 2.50 ppm; $^{13}$C 39.51 ppm), or (CH$_3$)$_4$Si. High-resolution mass spectra were obtained from the University of Texas at Austin Mass Spectrometry Facility (ESI and CI). Peaks are reported as m/z.

Synthetic Procedures and Compound Characterization Data

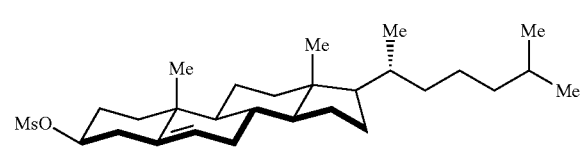

3β-Cholest-5-en-3-yl methanesulfonate. A solution of cholesterol (19.3 g, 50.0 mmol) in anhydrous CH$_2$Cl$_2$ (250 mL) was cooled to 4° C. by ice-water bath. To this solution, triethylamine (13.9 mL, 100.0 mmol) was added, followed by the dropwise addition of methanesulfonyl chloride (4.3 mL, 55 mmol) in anhydrous CH$_2$Cl$_2$ (50 mL). The reaction was maintained at 4° C. and stirred for 3 h. When the cholesterol was consumed as analyzed by TLC (hexanes/ethyl acetate, 5:1), the solvent was removed in vacuo. The resulting residue was redissolved in CH$_2$Cl$_2$ (15 mL), the product was precipitated by addition of MeOH (150 mL), and the product collected by vacuum filtration. The solid was washed with MeOH (30 mL) and dried under vacuum to yield the product (23.0 g, 99.0%) as a white solid, mp 119-120° C.; $^1$H NMR (300 MHz, CDCl$_3$) δ 5.41 (s, 1H), 4.56-4.45 (m, 1H), 3.00 (s, 3H), 2.57-2.43 (m, 2H), 2.04-0.81 (m, 38H), 0.67 (s, 3H); $^{13}$C NMR (75 MHz, CDCl$_3$) δ 138.6, 123.7, 81.9, 56.5, 56.0, 49.9, 42.2, 39.6, 39.4, 39.1, 38.7, 36.8, 36.3, 36.1, 35.7, 31.8, 31.7, 28.9, 28.1, 27.9, 24.2, 23.8, 22.8, 22.5, 20.9, 19.1, 18.6, 11.8; IR (film) ν max 3029, 2944, 2908, 2861, 1468, 1440, 1415, 1353, 1330, 1173 cm$^{-1}$; ESI+ m/z ((MNa)$^+$ 487.3237, C$_{28}$H$_{48}$O$_3$SNa requires 487.3222).

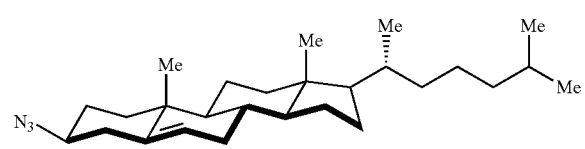

3β-Azido-5-cholestene. To a solution of 3β-cholest-5-en-3-yl methanesulfonate (9.30 g, 20.0 mmol) in anhydrous CH$_2$Cl$_2$ (100 mL), TMSN$_3$ (2.95 mL, 22.0 mmol) was added, followed by boron trifluoride etherate (5.0 mL, 40.0 mmol). The reaction was stirred at 22° C. for 2 h. When the starting material was no longer visible by TLC analysis (hexanes), the reaction was slowly poured into saturated aqueous NaHCO$_3$ (100 mL) and vigorously stirred for 10 min. The organic layer was separated and the aqueous layer was extracted with diethyl ether (60 mL×2). The organic layers were combined, washed with deionized water (100 mL), dried over anhydrous Na$_2$SO$_4$ and concentrated under reduced pressure to give the crude product as light yellow solid. Flash column chromatography (hexanes) afforded the product (7.75 g, 94.1%) as white solid, mp 84-86° C.; $^1$H NMR (300 MHz, CDCl$_3$) δ 5.38 (s, 1H), 3.26-3.15 (m, 1H), 2.28 (d, J=7.9 Hz, 2H), 2.05-0.85 (m, 38H), 0.68 (s, 3H); $^{13}$C NMR (75.4 MHz, CDCl$_3$) δ 139.8, 122.5, 61.1, 56.7, 56.1, 50.1, 42.3, 39.7, 39.5, 38.1, 37.6, 36.6, 36.2, 35.8, 31.8, 31.7, 28.2, 28.0, 27.9, 24.2, 23.8, 22.8, 22.5, 21.0, 19.2, 18.7, 11.8; IR (film) ν max 2934, 2896, 2861, 2097, 1464, 1443, 1377, 1367, 1243, 1231 cm$^{-1}$; APCI m/z 411.3607 (M$^+$, C$_{27}$H$_{45}$N$_3$ requires 411.3613).

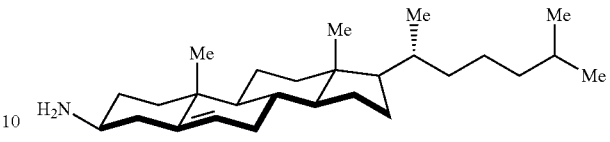

3β-Amino-5-cholestene. A solution of 3β-azido-5-cholestene (6.18 g, 15.0 mmol) in anhydrous diethyl ether (100 mL) was cooled to 4° C. by ice-water bath. To this solution, LiAlH$_4$ (855 mg, 22.5 mmol) was added in four equal portions. The reaction was maintained at 4° C. for 30 min, warmed to 22° C. and stirred for 2 h. When the starting material disappeared by TLC analysis (hexanes), the reaction was cooled to 4° C. and carefully quenched by slow dropwise addition of cold deionized water (10 mL). The resulting solution was poured into ice water (90 mL), the organic layer was separated, and the aqueous layer was extracted with ethyl acetate (50 mL×2). The organic layers was combined, washed with saturated aqueous sodium chloride (100 mL), dried over anhydrous Na$_2$SO$_4$ and concentrated in vacuo. The resulting residue was redissolved in CHCl$_3$ (30 mL) and insoluble salts were removed by filtration. Concentration of the filtrate afforded the product (5.57 g, 96.3%) as white solid, mp 92-94° C.; $^1$H NMR (300 MHz, CDCl$_3$) δ 5.27 (s, 1H), 2.60-2.52 (m, 1H), 2.10-0.81 (m, 40H), 0.64 (s, 3H); $^{13}$C NMR (75 MHz, CDCl$_3$) δ 141.7, 120.5, 56.7, 56.1, 51.9, 50.2, 43.3, 42.2, 39.7, 39.4, 38.1, 36.5, 36.1, 35.7, 32.6, 31.8 (×2), 28.2, 27.9, 24.2, 23.8, 22.7, 22.5, 20.9, 19.4, 18.6, 11.8; IR (film) ν 3354, 3260, 3154, 2936, 2896, 2849, 1464, 1437, 1381 cm$^{-1}$;

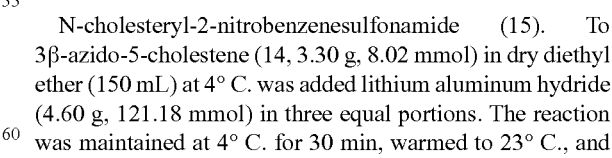

N-cholesteryl-2-nitrobenzenesulfonamide (15). To 3β-azido-5-cholestene (14, 3.30 g, 8.02 mmol) in dry diethyl ether (150 mL) at 4° C. was added lithium aluminum hydride (4.60 g, 121.18 mmol) in three equal portions. The reaction was maintained at 4° C. for 30 min, warmed to 23° C., and stirred for an additional 1.5 h. The reaction was quenched by addition of diethyl ether (50 mL) followed by careful dropwise addition of deionized H$_2$O (60 mL). The organic layer was washed with saturated aqueous NaCl (2×100 mL), dried over anhydrous Na$_2$SO$_4$, and concentrated in vacuo to afford 2.90 g (85%) of crude 3β-amino-5-cholestene. This aminosteroid was dissolved in dry THF (150 mL), and diisopropylethylamine (2.61 mL, 15.03 mmol) was added. 2-Nitrobenzenesulfonyl chloride (2.20 g, 9.92 mmol) in dry THF (40 mL) was added by addition funnel over 30 min. After 2 h at 23° C., solvents were removed in vacuo, $CH_2Cl_2$ was added (75 mL), and this organic solution was washed with aqueous $NaHCO_3$ (10%, 1×100 mL) and saturated aqueous NaCl (2×100 mL). The organic extracts were dried over anhydrous $Na_2SO_4$ and concentrated in vacuo to yield a crude yellow solid. Recrystallization ($CH_2Cl_2$/MeOH, 1:5) followed by flash column chromatography (EtOAc/hexanes, 1:5) afforded off-white 15 (3.50 g, 83%), mp 202-203° C.; $^1$H NMR (300 MHz, $CDCl_3$) δ 8.16-8.12 (m, 1H), 7.86-7.82 (m, 1H), 7.75-7.67 (m, 2H), 5.19 (s, 1H), 5.16 (s, 1H), 3.28-3.18 (m, 1H), 2.18-0.83 (m, 40H), 0.63 (s, 3H); $^{13}$C NMR (75.41 MHz, $CDCl_3$) δ 148.1, 139.9, 135.4, 133.6, 133.1, 131.0, 125.6, 122.7, 56.9, 56.3, 55.2, 50.2, 42.5, 40.3, 39.9, 39.7, 38.0, 36.6, 36.4, 36.0, 32.0, 31.9, 30.2, 28.4, 28.2, 24.4, 24.0, 23.0, 22.8, 21.1, 19.4, 18.9, 12.0; IR (film) $v_{max}$ 3331, 2936, 2359, 1541 cm$^{-1}$; CI m/z 571.3567 (MH$^+$, $C_{33}H_{51}N_2O_4S$ requires 571.3569).

N-[3-(tert-butoxycarbonylamino)propyl]-N-cholesteryl-2-nitrobenzenesulfonamide (16)

N-cholesteryl-2-nitrobenzenesulfonamide (15, 3.50 g, 6.14 mmol), potassium carbonate (12.50 g, 90.44 mmol) and Boc-3-chloropropylamine (2.50 g, 12.91 mmol, prepared as previously reported[5]) were added to dimethylacetamide (200 mL). This mixture was heated to 120° C. for 20 h. The reaction was filtered to remove excess potassium carbonate and the solvent was removed in vacuo. To the crude product was added $CH_2Cl_2$ (200 mL) and the organic solution was washed with aqueous citric acid (10%, 2×50 mL) and deionized water (50 mL). The organic layer was dried over anhydrous $Na_2SO_4$ and the solvent was removed in vacuo. Flash column chromatography (EtOAc/hexanes, 1:5 to 3:10) afforded 16 (3.56 g, 78%), mp 158-159° C.; $^1$H NMR (400 MHz, $CDCl_3$) δ 7.94 (m, 1H), 7.61 (m, 2H), 7.53 (m, 1H), 5.17 (d, J=4.8 Hz, 1H), 4.78 (br s, 1H), 3.55 (m, 1H), 3.29 (t, J=7.2 Hz, 2H), 3.12 (m, 2H), 2.36 (t, J=12.0 Hz, 1H), 1.97-0.91 (m, 37H), 0.89 (s, 3H), 0.84 (d, J=6.8 Hz, 3H), 0.80 (d, J=2.0 Hz, 3H), 0.78 (d, J=1.6 Hz, 3H), 0.59 (s, 3H); $^{13}$C NMR (100.6 MHz, $CDCl_3$) δ 156.5, 148.4, 140.4, 134.5, 133.8, 132.0, 131.1, 124.5,

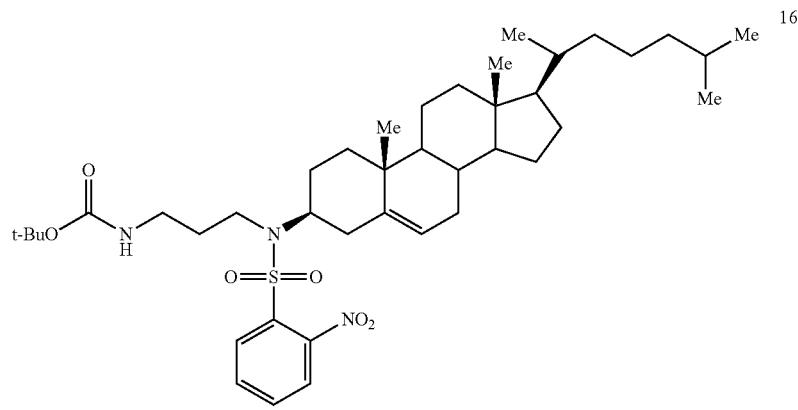

16

122.8, 79.6, 59.4, 57.1, 56.5, 50.4, 42.7, 42.1, 40.1, 39.9, 38.6, 38.1, 37.0, 36.6, 36.2, 32.6, 32.2, 32.1, 28.8 (×3), 28.7, 28.6, 28.4, 27.8, 24.6, 24.2, 23.2, 23.0, 21.3, 19.8, 19.1, 12.3; IR (film) $v_{max}$ 3400, 2800, 1700, 1550, 1320 cm$^{-1}$; MALDIFTMS (DHB) m/z 728.4669 (MH$^+$, $C_{41}H_{65}N_3O_6S$ requires 728.4672).

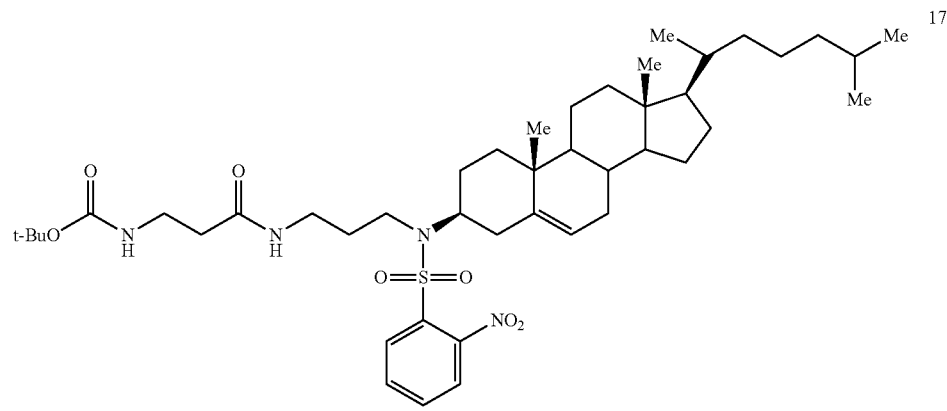

17 tert-butyl-3-[(3-{(3β)-cholest-5-en-3-yl[(2-nitrophenyl)sulfonyl]amino}propyl)amino]-3-oxopropylcarbamate (17). Trifluoroacetic acid in CH$_2$Cl$_2$ (2:25, 20 mL) was added to N-[3-(tert-butoxycarbonylamino)propyl]-N-cholesteryl-2-nitrobenzenesulfonamide (16, 100 mg, 0.138 mmol). After 1 h at 23 C, TLC analysis (MeOH/CH$_2$Cl$_2$, 1:50) revealed conversion to the more polar primary amine. Aqueous NaOH (1 M, 40 mL) was added, and the mixture was extracted with CH$_2$Cl$_2$ (2×10 mL). The organic layers were combined and dried over anhydrous Na$_2$SO$_4$. The solvent was removed in vacuo, and CH$_2$Cl$_2$ (18 mL), Boc-β-alanine N-hydroxysuccinimidyl ester (119 mg, 0.415 mmol), and diisopropylethylamine (50 μL, 0.277 mmol) were added. After 5 h at 23° C., CH$_2$Cl$_2$ (10 mL) and aqueous citric acid (10%, 50 mL) were added. This mixture was extracted with CH$_2$Cl$_2$ (2×10 mL), the organic extracts were combined, dried over anhydrous Na$_2$SO$_4$, and solvent removed in vacuo. Flash column chromatography (MeOH/CH$_2$Cl$_2$, 3:100) afforded 17 (103 mg, 93%), mp 154-156° C.; $^1$HNMR (400 MHz, CDCl$_3$) δ 8.00-7.97 (m, 1H), 7.71-7.66 (m, 2H), 7.61-7.58 (m, 1H), 6.29 (br s, 1H), 5.28 (br s, 1H), 5.22 (d, J=4.7 Hz, 1H), 3.69-3.58 (m, 1H), 3.42-3.39 (m, 6H), 2.45-2.40 (m, 3H), 2.00-0.97 (m, 29H), 1.42 (s, 9H), 0.94 (s, 3H), 0.90 (d, J=6.49 Hz, 3H), 0.86 (d, J=1.81 Hz, 3H), 0.84 (d, J=1.80 Hz, 3H), 0.65 (s, 3H); $^{13}$C NMR (75.4 MHz, CDCl$_3$) δ 172.0, 156.2, 148.2, 140.1, 134.0, 133.7, 131.8, 130.7, 124.2, 122.6, 79.3, 59.3, 56.8, 56.2, 50.1, 42.4, 41.7, 39.8, 39.7, 38.4, 37.8, 36.8, 36.7, 36.4, 36.3 (×2), 35.9, 32.0, 31.9, 31.7, 28.6 (×3), 28.4, 28.2, 27.7, 24.4, 24.0, 23.0, 22.7, 21.1, 19.6, 18.9, 12.0; IR (film) ν$_{max}$ 3413, 3321, 2937, 2868, 1702, 1655, 1546, 1367 cm$^{-1}$; CI m/z 799.5062 (MH$^+$, C$_{44}$H$_{71}$N$_4$O$_7$S requires 799.5043).

tert-butyl-3-({3-[(3-{(3β)-cholest-5-en-3-yl[(2-nitrophenyl)sulfonyl]amino}propyl)amino]-3-oxopropyl}amino)-3-oxopropylcarbamate (18). Trifluoroacetic acid in CH$_2$Cl$_2$ (2:25, 10 mL) was added to tert-butyl 3-[(3-{(3β)-cholest-5-en-3-yl[(2-nitrophenyl)sulfonyl]amino}propyl)amino]-3-oxopropylcarbamate (17) (50 mg, 0.062 mmol). After 1 h at 23° C., TLC analysis (MeOH/CH$_2$Cl$_2$, 1:50) revealed conversion to the more polar primary amine. Aqueous NaOH (1 M, 20 mL) was added, the mixture was extracted with CH$_2$Cl$_2$ (2×5 mL), the combined organic extracts were dried over anhydrous Na$_2$SO$_4$, and solvent was removed in vacuo. Boc-β-alanine N-hydroxysuccinimidyl ester (54 mg, 0.189 mmol), CH$_2$Cl$_2$ (9 mL) and diisopropylethylamine (50 μL, 0.277 mmol) were added. After stirring for 5 h at 23° C., CH$_2$Cl$_2$ (5 mL) and aqueous citric acid (10%, 25 mL) were added followed by extraction with CH$_2$Cl$_2$ (2×5 mL). The organic extracts were dried over anhydrous Na$_2$SO$_4$ and removed in vacuo. Flash column chromatography (MeOH/CH$_2$Cl$_2$, 3:100) afforded 18 (52 mg, 95%), mp 96-98° C.; $^1$H NMR (400 MHz, CDCl$_3$) δ 8.03-7.97 (m, 1H), 7.73-7.67 (m, 2H), 7.65-7.59 (m, 1H), 6.66 (br s, 1H), 6.58 (br s, 1H), 5.30 (br s, 1H), 5.21 (d, J=4.6 Hz, 1H), 3.63-3.52 (m, 3H), 3.40-3.32 (m, 6H), 2.46-2.35 (m, 5H), 2.01-0.98 (m, 29H), 1.42 (s, 9H), 0.95 (s, 3H), 0.91 (d, J=6.5 Hz, 3H), 0.87 (d, J=1.8 Hz, 3H), 0.86 (d, J=1.8 Hz, 3H), 0.66 (s, 3H); $^{13}$C NMR (75.5 MHz, CDCl$_3$) δ 172.2, 171.8, 156.3, 148.1, 140.1, 134.0, 133.8, 131.9, 130.8, 124.3, 122.7, 79.3, 59.3, 56.8, 56.3, 50.1, 42.4, 41.8, 39.8, 39.7, 38.4, 37.8, 37.0, 36.7, 36.4 (×2), 36.3 (×2), 35.9, 35.8, 32.0 (×2), 31.9, 28.6 (×3), 28.4, 28.2, 27.7, 24.4, 24.0, 23.0, 22.7, 21.1, 19.6, 18.9, 12.0; IR (film) ν$_{max}$ 3378, 3284, 2935, 2867, 1688, 1643, 1548, 1366 cm$^{-1}$; CI m/z 870.5407 (MH$^+$, C$_{47}$H$_{76}$N$_5$O$_8$S requires 870.5415).

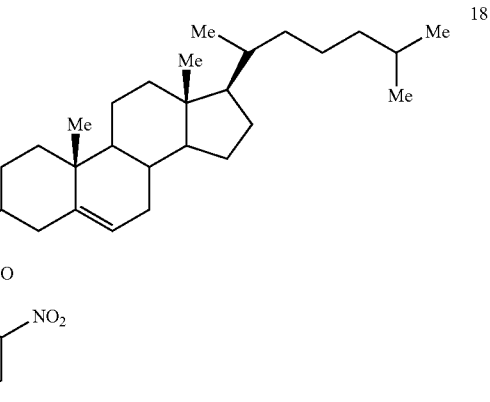

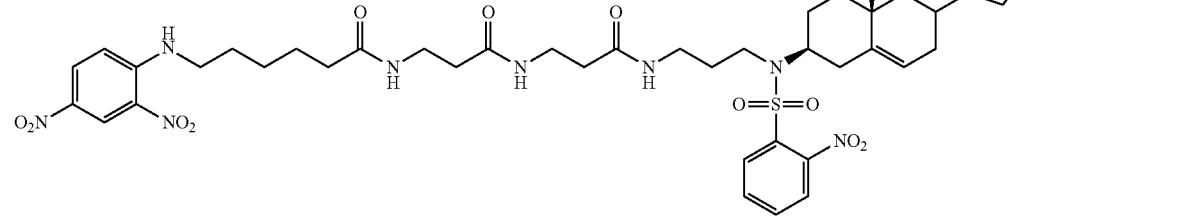

N-[3-({3-[(3-{(3β)-cholest-5-en-3-yl[(2-nitrophenyl)sulfonyl]amino}propyl)amino]-3-oxopropyl}amino)-3-oxopropyl]-6-[(2,4-dinitrophenyl)amino]hexanamide (21). tert-butyl 3-({3-[(3-{(3β)-cholest-5-en-3-yl[(2-nitrophenyl)sulfonyl]amino}propyl)amino]-3-oxopropyl}amino)-3-oxopropylcarbamate (18, 52 mg, 0.060 mmol) was treated with trifluoroacetic acid in $CH_2Cl_2$ (2:25, 10 mL). After 1 h at 23° C., TLC analysis ($MeOH/CH_2Cl_2$, 1:25) revealed conversion to the more polar primary amine. Aqueous NaOH (1 M, 40 mL) was added, the mixture was extracted with $CH_2Cl_2$ (2×10 mL), the organic layers were dried over anhydrous $Na_2SO_4$, and the solvent was removed in vacuo. The remaining residue was dissolved in $CH_2Cl_2$ (10 mL) and 6-(2,4-dinitrophenyl)aminohexanoic acid succinimidyl ester (71 mg, 0.180 mmol) and diisopropylethylamine (50 μL, 0.287 mmol) were added. After 8 h at 23° C., ethylenediamine (50 μL) was added with stirring for 30 min to consume the excess active ester. $CH_2Cl_2$ (5 mL) and aqueous citric acid (10%, 25 mL) were added followed by extraction with $CH_2Cl_2$ (2×5 mL). The organic layer was dried over anhydrous $Na_2SO_4$ and removed in vacuo. Flash column chromatography ($MeOH/CH_2Cl_2$, 1:25) afforded 21 (60 mg, 96%), mp 106-108° C.; $^1H$ NMR (500 MHz, $CDCl_3$) δ 9.10 (d, J=2.59 Hz, 1H), 8.57 (t, J=4.98 Hz, 1H), 8.25 (dd, J=2.6 Hz, J=9.5 Hz, 1H), 8.01-7.97 (m, 1H), 7.74-7.68 (m, 2H), 7.64-7.59 (m, 1H), 6.93 (d, J=9.6 Hz, 1H), 6.70 (t, J=5.5 Hz, 1H), 6.65 (t, J=5.7 Hz, 1H), 6.58 (d, J=5.1 Hz, 1H), 5.19 (d, J=4.9 Hz, 1H), 3.57-3.51 (m, 5H), 3.44-3.34 (m, 6H), 2.43 (t, J=5.9 Hz, 2H), 2.38 (t, J=5.9 Hz, 2H), 2.21 (d, J=7.4 Hz, 2H), 2.01-1.67 (m, 13H), 1.58-1.22 (m, 14H), 1.18-0.97 (m, 9H), 0.94 (s, 3H), 0.90 (d, J=6.5 Hz, 3H), 0.87 (d, J=2.4 Hz, 3H), 0.86 (d, J=2.2 Hz, 3H), 0.66 (s, 3H); $^{13}C$ NMR (125.8 MHz, $CDCl_3$) δ 172.9, 172.1 (×2), 148.6, 148.1, 140.0, 136.1, 133.9, 133.8, 131.9, 130.8, 130.5, 130.4, 124.5, 124.3, 122.7, 114.2, 59.3, 56.8, 56.3, 50.2, 43.5, 42.5, 41.8, 39.8, 39.7, 38.4, 37.8, 36.7, 36.4, 36.4, 36.3, 35.9, 35.9, 35.8, 34.1, 32.0, 31.9, 28.6, 28.4, 28.2, 27.7, 26.6, 25.8, 25.2, 25.1, 24.4, 24.0, 23.0, 22.7, 21.1, 19.6, 18.9, 12.0; IR (film) $v_{max}$ 3378, 3287, 2937, 2867, 1634, 1622, 1548, 1337 $cm^{-1}$; CI m/z 1049.5764 ($MH^+$, $C_{54}H_{81}N_8O_{11}S$ requires 1049.5745).

N-(3-{[3-({3-[(3β)-cholest-5-en-3-ylamino]propyl}amino)-3-oxopropyl]amino}-3-oxopropyl)-6-[(2,4-dinitrophenyl)amino]hexanamide (2). To a slurry of N-[3-({3-[(3-{(3β)-cholest-5-en-3-yl[(2-nitrophenyl)sulfonyl]amino}propyl)amino]-3-oxopropyl}amino)-3-oxopropyl]-6-[(2,4-dinitrophenyl)amino]hexanamide (21, 60 mg, 0.057 mmol) and $K_2CO_3$ (90 mg, 0.651 mmol) in DMF (4 mL) and THF (1 mL) was added thiophenol (80 μL, 0.874 mmol). After 18 h at 23° C., solids were removed by filtration and solvent was removed in vacuo. The crude product was purified by flash column chromatography ($CH_2Cl_2$/MeOH/TEA, 93: 4:3) to afford 2 (36 mg, 72%) mp 191-193° C.; $^1H$ NMR (400 MHz, $CDCl_3$) δ 9.14 (d, J=2.6 Hz, 1H), 8.56 (t, J=4.9 Hz, 1H), 8.27 (dd, J=2.6 Hz, J=9.50 Hz, 1H), 7.40 (t, J=5.2 Hz, 1H), 6.93 (d, J=9.6 Hz, 1H), 6.69 (t, J=5.5 Hz, 1H), 6.60 (t, J=5.4 Hz, 1H), 5.32 (d, J=4.4 Hz, 1H), 3.54-3.50 (m, 4H), 3.42 (dt, J=6.9 Hz, J=5.6 Hz, 2H), 3.34 (dt, J=5.6 Hz, J=5.60 Hz, 2H), 2.76 (t, J=5.6 Hz, 2H), 2.39-2.34 (m, 5H), 2.21 (t, J=7.3 Hz, 2H), 2.02-1.00 (m, 37H), 0.98 (s, 3H), 0.91 (d, J=6.5 Hz, 3H), 0.87 (d, J=1.6 Hz, 3H), 0.86 (d, J=1.6 Hz, 3H), 0.67 (s, 3H); $^{13}C$ NMR (125.8 MHz, $CDCl_3$) δ 172.5, 171.8, 171.3, 148.3, 141.2, 136.0, 130.5, 130.3, 124.3, 121.1, 113.9, 58.3, 56.8, 56.2, 50.3, 45.5, 43.3, 40.1, 39.8, 39.5, 39.3, 38.0, 37.0, 36.2 (×2), 35.8, 35.6 (×2), 35.5, 35.4, 31.9 (×2), 29.7, 29.6, 28.8, 28.4, 28.2, 28.0, 26.4, 25.0, 24.3, 23.8, 22.8, 22.5, 21.0, 19.4, 18.7, 11.8; IR (film) $v_{max}$ 3295, 2927, 2849, 1633, 1546, 1340 $cm^{-1}$; CI m/z 864.5959 ($MH^+$, $C_{48}H_{78}N_7O_7$ requires 864.5963).

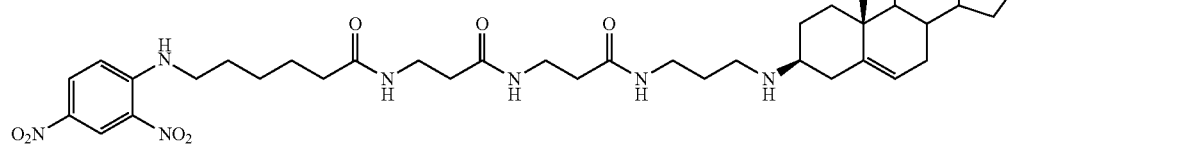

2

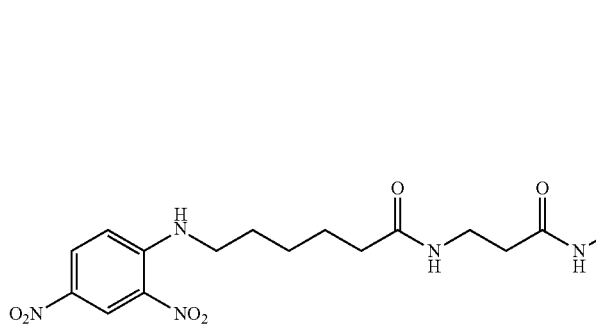
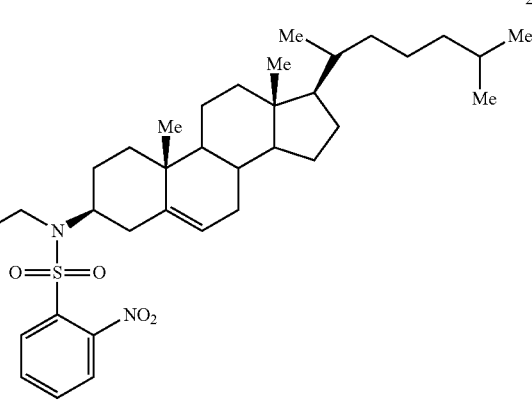

N-{3-[(3-{(3β)-cholest-5-en-3-yl[(2-nitrophenyl)sulfonyl]amino}propyl)amino]-3-oxopropyl}-6-[(2,4-dinitrophenyl)amino]hexanamide (20). Trifluoroacetic acid in CH$_2$Cl$_2$ (2:25, 7.5 mL) was added to tert-butyl 3-[(3-{(3β)-cholest-5-en-3-yl[(2-nitrophenyl)sulfonyl]amino}propyl)amino]-3-oxopropylcarbamate (17, 100 mg, 0.125 mmol). After 1 h at 23° C., TLC analysis (MeOH in CH$_2$Cl$_2$, 1:50) revealed conversion to the more polar primary amine. Aqueous NaOH (1 M, 35 mL) was added, the mixture was extracted with CH$_2$Cl$_2$ (2×20 mL), the organic extracts were combined, dried over anhydrous Na$_2$SO$_4$, and solvent was removed in vacuo. The remaining residue was dissolved in CH$_2$Cl$_2$ (17 mL) and 6-(2,4-dinitrophenyl)aminohexanoic acid succinimidyl ester (54 mg, 0.137 mmol) and diisopropylethylamine (50 μL, 0.277 mmol) were added. After 6 h at 23° C., ethylenediamine (100 μL) was added to consume excess active ester, and the mixture was stirred at 23° C. for 30 min. CH$_2$Cl$_2$ (10 mL) and aqueous citric acid (10%, 45 mL) were added followed by extraction with CH$_2$Cl$_2$ (2×10 mL). The organic extracts were combined, dried over anhydrous Na$_2$SO$_4$, and solvent removed in vacuo. Flash column chromatography (MeOH/CH$_2$Cl$_2$, 1:50) afforded 20 (121 mg, 99%), mp 86-87° C.; $^1$H NMR (360 MHz, CDCl$_3$) δ 9.10 (d, J=2.7 Hz, 1H), 8.55 (t, J=4.8 Hz, 1H), 8.24 (dd, J=9.5 Hz, J=2.64 Hz, 1H), 8.00-7.97 (m, 1H), 7.71-7.68 (m, 2H), 7.61-7.58 (m, 1H), 6.92 (d, J=9.6 Hz, 1H), 6.51 (t, J=5.7 Hz, 1H), 6.36 (t, J=5.9 Hz, 1H), 5.19 (d, J=4.8 Hz, 1H), 3.61-3.52 (m, 3H), 3.44-3.32 (m, 6H), 2.46-2.42 (m, 3H), 2.21 (t, J=7.3 Hz, 2H), 1.97-0.97 (m, 35H), 0.94 (s, 3H), 0.90 (d, J=6.5 Hz, 3H), 0.87 (d, J=1.6 Hz, 3H), 0.85 (d, J=1.6 Hz, 3H), 0.65 (s, 3H); $^{13}$C NMR (125.8 MHz, CDCl$_3$) δ 172.7, 172.0, 148.4, 147.9, 139.8, 135.8, 133.7, 133.6, 131.7, 130.6, 130.3, 130.2, 124.3, 124.1, 122.5, 114.0, 59.1, 56.6, 56.1, 49.9, 43.3, 42.2, 41.5, 39.6, 39.5, 38.2, 37.6, 36.5, 36.2 (×2), 36.1, 35.7, 35.5 (×2), 31.8, 31.7 (×2), 28.4, 28.2, 28.0, 27.5, 26.4, 25.0, 24.2, 23.8, 22.8, 22.5, 20.9, 19.4, 18.7, 11.8; IR (film) ν$_{max}$ 3365, 3305, 2938, 2867, 1648, 1621, 1544, 1336 cm$^{-1}$; CI m/z 978.5370 (MH$^+$, C$_{51}$H$_{76}$N$_7$O$_{10}$S requires 978.5374).

N-[3-({3-[(3β)-cholest-5-en-3-ylamino]propyl}amino)-3-oxopropyl]-6-[(2,4-dinitrophenyl)amino]hexanamide (3). To a slurry of N-{3-[(3-{(3β)-cholest-5-en-3-yl[(2-nitrophenyl)sulfonyl]amino}propyl)amino]-3-oxopropyl}-6-[(2,4-dinitrophenyl)amino]hexanamide (20, 121 mg, 0.124 mmol) and K$_2$CO$_3$ (137 mg, 0.991 mmol) in N,N-dimethylformamide (8 mL) and tetrahydrofuran (4 mL) was added thiophenol (100 μL, 0.971 mmol). After stirring at 23° C. for 18 h, the mixture was filtered and solvent removed in vacuo. Flash column chromatography (MeOH/triethylamine/CH$_2$Cl$_2$, 3:5:100) afforded 3 (50 mg, 51%) mp 157-158° C.; $^1$H NMR (360 MHz, CDCl$_3$) δ 9.12 (d, J=2.6 Hz, 1H), 8.55 (t, J=5.0 Hz, 1H), 8.26 (dd, J=2.6 Hz, J=9.5 Hz, 1H), 6.91 (d, J=9.6 Hz, 1H), 6.62 (t, J=5.5 Hz, 1H), 5.30 (d, J=4.7 Hz, 1H), 3.51 (dt, J=5.8 Hz, J=5.7 Hz, 2H), 3.41 (dt, J=7.0 Hz, J=5.5 Hz, 2H), 3.33 (dt, J=5.9 Hz, J=5.7 Hz, 2H), 2.74 (t, J=6.0 Hz, 2H), 2.38-2.31 (m, 3H), 2.21-2.14 (m, 3H), 2.01-1.00 (m, 37H), 0.97 (s, 3H), 0.90 (d, J=6.5 Hz, 3H), 0.86 (d, J=1.4 Hz, 3H), 0.84 (d, J=1.4 Hz, 3H), 0.66 (s, 3H); $^{13}$C NMR (125.8 MHz, CDCl$_3$) δ 172.6, 171.8, 148.5, 141.6, 136.2, 130.6, 130.5, 124.6, 121.2, 114.1, 58.4, 57.0, 56.3, 50.5, 45.7, 43.5, 42.5, 40.4, 40.0, 39.7, 39.5, 38.2, 37.2, 36.5, 36.4, 36.0, 35.7, 35.5, 32.1 (×2), 29.9, 29.1, 28.6, 28.4, 28.2, 26.7, 25.2, 24.5, 24.0, 23.0, 22.7, 21.2, 19.6, 18.9, 12.0; IR (film) ν$_{max}$ 3354, 3299, 2933, 2868, 1647, 1620, 1335 cm$^{-1}$; CI m/z 793.5584 (MH$^+$, C$_{45}$H$_{73}$N$_6$O$_6$ requires 793.5592).

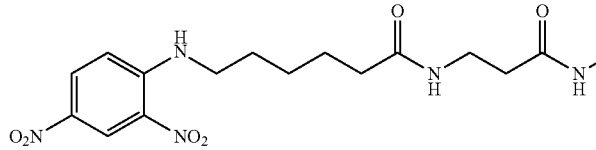

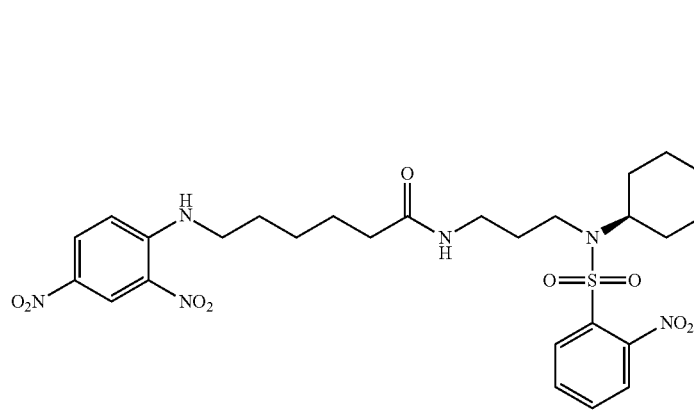
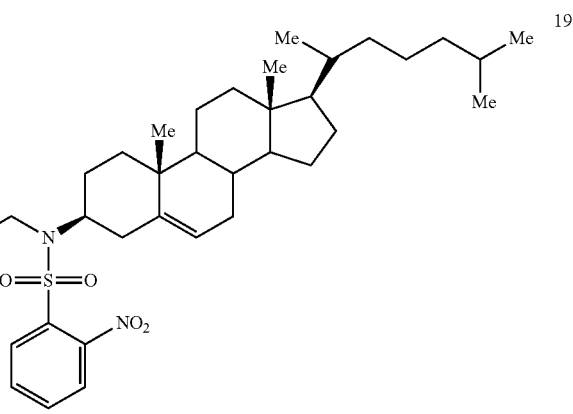

N-(3-{(3β)-cholest-5-en-3-yl[(2-nitrophenyl)sulfonyl]amino}propyl)-6-[(2,4-dinitrophenyl)amino]hexanamide (19). N-[3-(tert-butoxycarbonylamino)propyl]-N-cholesteryl-2-nitrobenzenesulfonamide (16, 234 mg, 0.323 mmol) was treated with trifluoroacetic acid in CH$_2$Cl$_2$ (2:50, 47 mL). After 1 h at 23° C., TLC analysis (MeOH/CH$_2$Cl$_2$, 1:50) revealed conversion to the more polar primary amine. Aqueous NaOH (1 M, 40 mL) was added followed by extraction with CH$_2$Cl$_2$ (3×25 mL). The organic layers were combined, dried over anhydrous Na$_2$SO$_4$, and the solvent was removed in vacuo. The remaining residue was dissolved in CH$_2$Cl$_2$ (40 mL) and 6-(2,4-dinitrophenyl)aminohexanoic acid succinimidyl ester (130 mg, 0.330 mmol) and diisopropylethylamine (62 μL, 0.355 mmol) were added. After 6 h at 23° C., ethylenediamine (100 μL) was added as an active ester scavenger and allowed to react for 30 min. CH$_2$Cl$_2$ (20 mL) and aqueous citric acid (10%, 50 mL) were added followed by extraction with CH$_2$Cl$_2$ (2×30 mL). The organic extracts were combined, dried over anhydrous Na$_2$SO$_4$, and solvent removed in vacuo. Flash column chromatography (MeOH/CH$_2$Cl$_2$, 1:25) afforded 19 (195 mg, 66%), mp 80-82° C.; $^1$H NMR (400 MHz, CDCl$_3$) δ 9.05 (d, J=2.7 Hz, 1H), 8.58 (t, J=5.1 Hz, 1H), 8.20 (dd, J=2.6 Hz, J=9.5 Hz, 1H), 7.99-7.97 (m, 1H), 7.75-7.68 (m, 2H), 7.62-7.59 (m, 1H), 6.95 (d, J=9.6 Hz, 1H), 6.42 (t, J=5.9 Hz, 1H), 5.19 (d, J=4.6 Hz, 1H), 3.62-3.56 (m, 1H), 3.47-3.34 (m, 6H), 2.46-2.40 (m, 1H), 2.27 (t, J=7.3 Hz, 2H), 2.00-0.97 (m, 35H), 0.94 (s, 3H), 0.90 (d, J=6.5 Hz, 3H), 0.87 (d, J=1.8 Hz, 3H), 0.85 (d, J=1.8 Hz, 3H), 0.65 (s, 3H); $^{13}$C NMR (75.5 MHz, CDCl$_3$) δ 173.0, 148.5, 148.0, 140.0, 135.8, 133.8, 133.7, 131.8, 130.6, 130.3, 130.2, 124.2, 124.1, 122.5, 114.2, 59.2, 56.7, 56.2, 50.0, 43.4, 42.3, 41.7, 39.7, 39.5, 38.3, 37.7, 36.6, 36.4, 36.2, 35.8, 34.0, 31.9, 31.8, 31.6, 28.4, 28.2, 28.0, 27.5, 26.5, 25.1, 24.3, 23.9, 22.9, 22.6, 21.0, 19.4, 18.8, 11.9; IR (film) ν$_{max}$ 3365, 2934, 2866, 1621, 1545, 1336 cm$^{-1}$; CI m/z 907.5003 (MH$^+$, C$_{48}$H$_{71}$N$_6$O$_9$S requires 907.5003).

N-{3-[(3β)-cholest-5-en-3-ylamino]propyl}-6-[(2,4-dinitrophenyl)amino]hexanamide (4). To a slurry of N-(3-{(3β)-cholest-5-en-3-yl[(2-nitrophenyl)sulfonyl]amino}propyl)-6-[(2,4-dinitrophenyl)amino]hexanamide (19, 164 mg, 0.180 mmol) and K$_2$CO$_3$ (270 mg, 1.954 mmol) in N,N-dimethylformamide (20 mL) was added thiophenol (80 μL, 0.777 mmol). After stirring at 23° C. for 18 h, the mixture was filtered and solvent was removed in vacuo. The crude product was purified by flash column chromatography (MeOH/triethylamine/CH$_2$Cl$_2$, 2:5:100) to afford 4 (77 mg, 59%) mp 165-166° C.; $^1$H NMR (500 MHz, CDCl$_3$) δ 9.11 (d, J=2.6 Hz, 1H), 8.53 (br s, 1H), 8.25 (dd, J=2.5 Hz, J=9.5 Hz, 1H), 6.99 (t, J=4.3, 1H), 6.90 (d, J=9.5 Hz, 1H), 5.29 (d, J=4.8 Hz, 1H), 3.42-3.38 (m, 2H), 3.34 (dt, J=5.8 Hz, J=5.9 Hz, 2H), 2.74 (t, J=6.1 Hz, 2H), 2.39-2.34 (m, 1H), 2.23-2.17 (m, 3H), 2.04-1.92 (m, 4H), 1.84-0.98 (m, 32H), 0.95 (s, 3H), 0.90 (d, J=6.5 Hz, 3H), 0.85 (d, J=2.1 Hz, 3H), 0.84 (d, J=2.1 Hz, 3H), 0.65 (s, 3H); $^{13}$C NMR (75.5 MHz, CDCl$_3$) δ 172.5, 148.5, 141.5, 136.2, 130.5 (×2), 124.5, 121.2, 114.7, 58.4, 56.9, 56.3, 50.4, 45.5, 43.6, 42.5, 40.3, 39.9, 39.7, 39.3, 38.1, 37.2, 36.6, 36.4, 36.0, 32.1, 32.0, 29.7, 29.2, 28.7., 28.4, 28.2, 26.8, 25.3, 24.4, 24.0, 23.0, 22.7, 21.2, 19.6, 18.9, 12.0; IR (film) ν$_{max}$ 3362, 3295, 2934, 2867, 1622, 1336 cm$^{-1}$; CI m/z 722.5229 (MH$^+$, C$_{42}$H$_{68}$N$_5$O$_5$ requires 722.5220).

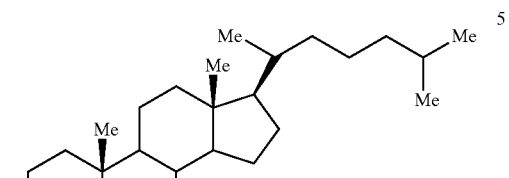
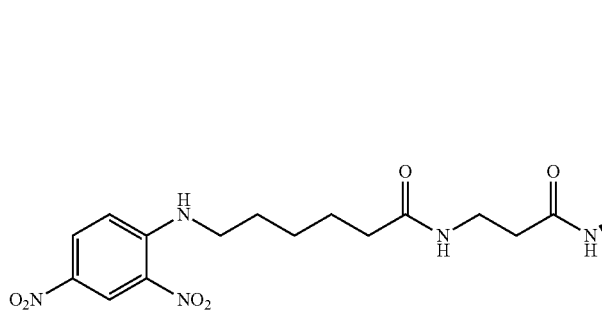

N-{3-[(3β)-cholest-5-en-3-ylamino]-3-oxopropyl}-6-[(2,4-dinitrophenyl)amino]hexanamide (5). To 3-(tert-butoxycarbonylamino)-N-cholesterylpropionamide (44 mg, 0.079 mmol, prepared as previously reported[6]) was added trifluoroacetic acid in $CH_2Cl_2$ (1:20, 10 mL). After 2 h at 23° C., TLC analysis (MeOH/$CH_2Cl_2$, 1:20) revealed conversion to the more polar primary amine. Aqueous NaOH (1 M, 40 mL) was added followed by extraction with $CH_2Cl_2$ (2×15 mL). The organic extracts were combined, dried over anhydrous $Na_2SO_4$, and solvent was removed in vacuo. $CH_2Cl_2$ (10 mL) was added followed by 6-(2,4-dinitrophenyl)aminohexanoic acid succinimidyl ester (37 mg, 0.095 mmol) and diisopropylethylamine (80 μL, 0.459 mmol). After 6 h at 23° C., $CH_2Cl_2$ (10 mL) and aqueous citric acid (10%, 30 mL) were added. This mixture was extracted with $CH_2Cl_2$ (2×15 mL), the organic layer was dried over anhydrous $Na_2SO_4$, and solvent was removed in vacuo. Flash column chromatography (MeOH/$CH_2Cl_2$, 1:50) afforded 5 (47 mg, 80%), mp 197-198° C.; $^1$H NMR (400 MHz, CDCl$_3$) δ 9.15 (d, J=2.7 Hz, 1H), 8.56 (br s, 1H), 8.28 (dd, J=2.5 Hz, J=9.6 Hz, 1H), 6.92 (d, J=9.6 Hz, 1H), 6.46 (d, J=5.5 Hz, 1H), 5.56 (d, J=8.0 Hz, 1H), 5.36-5.35 (m, 1H), 3.71-3.63 (m, 1H), 3.55-3.51 (m, 2H), 3.44-3.40 (m, 2H), 2.39 (t, J=5.8 Hz, 2H), 2.30-2.26 (m, 1H), 2.21 (t, J=7.3 Hz, 2H), 2.09-1.00 (m, 33H), 0.98 (s, 3H), 0.92 (d, J=6.52 Hz, 3H), 0.88 (d, J=1.8 Hz, 3H), 0.86 (d, J=1.8 Hz, 3H), 0.68 (s, 3H); $^{13}$C NMR (90.6 MHz, CDCl$_3$) δ 172.8, 171.0, 148.6, 140.3, 136.3, 130.6 (×2), 124.6, 122.4, 114.1, 56.9, 56.4, 50.3, 50.1, 43.5, 42.5, 39.9, 39.7, 39.5, 38.0, 36.8, 36.5, 36.4, 36.0, 35.8, 35.7, 32.1, 29.9, 29.3, 28.6, 28.4, 28.2, 26.7, 25.2, 24.5, 24.0, 23.0, 22.8, 21.2, 19.5, 18.9, 12.1; IR (CDCl$_3$) $v_{max}$ 3691, 2937, 2868, 1660, 1622, 1475, 1338 cm$^{-1}$; CI m/z 736.5013 (MH$^+$, $C_{42}H_{66}N_5O_6$ requires 736.5013).

N-[3-({3-[(3-{(3β)-cholest-5-en-3-yl[(2-nitrophenyl)sulfonyl]amino}propyl)amino]-3-oxopropyl}amino)-3-oxopropyl]-6-(7-nitrobenzofurazan-4-ylamino)hexanamide (24). tert-butyl 3-({3-[(3-{(3β)-cholest-5-en-3-yl[(2-nitrophenyl)sulfonyl]amino}propyl)amino]-3-oxopropyl}amino)-3-oxopropyl carbamate (18, 41 mg, 0.047 mmol) was treated with trifluoroacetic acid in $CH_2Cl_2$ (2:25, 10 mL). After 2 h at 23° C., TLC analysis (MeOH/$CH_2Cl_2$, 1:25) revealed conversion to the more polar primary amine. Aqueous NaOH (1 M, 10 mL) was added, the mixture was extracted with $CH_2Cl_2$ (2×10 mL), the organic extracts were combined, dried over anhydrous $Na_2SO_4$, and solvent was removed in vacuo. $CH_2Cl_2$ (10 mL) was added followed by 6-(N-(7-nitrobenz-2-oxa-1,3-diazol-4-yl)amino)hexanoic acid succinimidyl ester (22 mg, 0.057 mmol) and diisopropylethylamine (100 μL, 0.471 mmol). After 8 h at 23° C., aqueous citric acid (10%, 20 mL) was added followed by extraction with $CH_2Cl_2$ (2×10 mL). The organic extracts were dried over anhydrous $Na_2SO_4$ and solvent removed in vacuo. Flash column chromatography (MeOH/$CH_2Cl_2$, 1:25) afforded 24 (36 mg, 72%), mp 113-114° C.; $^1$H NMR (300 MHz, CDCl$_3$) δ 8.45 (d, J=8.72 Hz, 1H), 7.99 (m, 1H), 7.71 (m, 2H), 7.61 (m, 1H), 7.48 (br s, 1H), 6.80 (t, J=5.6 Hz, 1H), 6.71 (t, J=5.6 Hz, 2H), 6.17 (d, J=8.8 Hz, 1H), 5.18 (d, J=4.1 Hz, 1H), 3.64-3.46 (m, 7H), 3.41-3.34 (m, 4H), 2.47-2.38 (m, 5H), 2.23 (t, J=6.9 Hz, 2H), 2.16-0.97 (m, 35H), 0.93 (s, 3H), 0.90 (d, J=6.4 Hz, 3H), 0.87 (d, J=1.2 Hz, 3H), 0.85 (d, J=1.2 Hz, 3H), 0.65 (s, 3H); $^{13}$C NMR (75.4 MHz, CDCl$_3$) δ 173.3, 172.2 (×2), 148.1, 144.7, 144.5, 144.3, 140.0, 137.0, 133.9, 133.8, 132.0, 130.7, 124.3, 123.2, 122.8, 98.8, 59.3, 56.8, 56.3, 50.1, 44.0, 42.5, 41.8, 39.8, 39.7, 38.4, 37.8, 36.7, 36.5, 36.3 (×2), 36.1 (×2), 36.0 (×2), 35.9, 32.0, 31.9, 29.9, 28.4, 28.2, 27.9, 27.7, 26.4, 25.0, 24.4, 24.0, 23.0, 22.8, 21.1, 19.6,

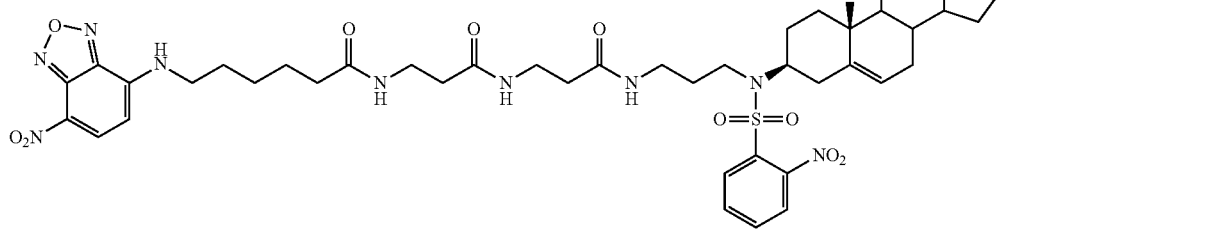

18.9, 12.0; IR (film) $v_{max}$ 3292, 2936, 2868, 1650, 1585, 1547, 1300 cm$^{-1}$; CI m/z 1046.5723 (MH$^+$, C$_{54}$H$_{80}$N$_9$O$_{10}$S requires 1046.5749).

N-{3-[(3-{(3β)-cholest-5-en-3-yl[(2-nitrophenyl)sulfonyl]amino}propyl)amino]-3-oxopropyl}-6-(7-nitrobenzofurazan-4-ylamino)hexanamide (23). Trifluoroacetic acid in

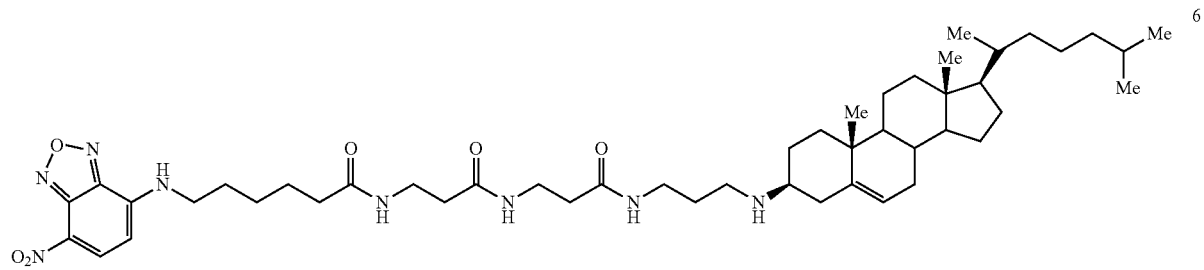

N-(3-{[3-({3-[(3β)-cholest-5-en-3-ylamino]propyl}amino)-3-oxopropyl]amino}-3-oxopropyl)-6-(7-nitrobenzofurazan-4-ylamino)hexanamide (6). To a slurry of N-[3-({3-[(3-{(3β)-cholest-5-en-3-yl[(2-nitrophenyl)sulfonyl]amino}propyl)amino]-3-oxopropyl}amino)-3-oxopropyl]-6-(7-nitrobenzofurazan-4-ylamino)hexanamide (24, 29 mg, 0.028 mmol) and K$_2$CO$_3$ (76 mg, 0.552 mmol) in N,N-dimethylformamide (6 mL) and tetrahydrofuran (2 mL) was added thiophenol (40 µL, 0.389 mmol). After 18 h at 23° C., the suspension was filtered and solvent removed in vacuo. Purification by preparative reverse-phase HPLC (gradient: 59.9% MeCN, 40% H$_2$O, and 0.1% TFA to 99.9% MeCN, 0% H$_2$O, and 0.1% TFA over 14 min; retention time=10.6 min) afforded 6 (15 mg, 52%) mp 170-171° C.; $^1$H NMR (500 MHz, CDCl$_3$) δ 9.54 (br s, 1H), 8.68 (br s, 1H), 8.50 (d, J=8.4 Hz, 1H), 8.07 (t, J=5.35, 1H), 7.92 (t, J=5.4 Hz, 1H), 7.80 (t, J=5.3 Hz, 1H), 6.40 (d, J=8.9 Hz, 1H), 5.36 (m, 1H), 3.43 (m, 1H), 3.24-3.17 (m, 4H), 3.10 (m, 2H), 2.88 (br s, 3H), 2.35 (d, J=7.2 Hz, 2H), 2.23 (t, J=6.9 Hz, 2H), 2.18 (t, J=7.1 Hz, 2H), 2.04 (t, J=7.2 Hz, 2H), 1.94-0.96 (m, 35H), 0.93 (s, 3H), 0.86 (d, J=6.2 Hz, 3H), 0.84 (d, J=2.1 Hz, 3H), 0.82 (d, J=2.1 Hz, 3H), 0.62 (s, 3H); $^{13}$C NMR (125.8 MHz, DMSO d$_6$) δ 171.9, 170.8, 170.3, 145.1, 144.4, 144.2, 138.6, 137.9 122.3, 120.5, 99.1, 56.6, 56.1, 55.5, 49.3 (×2), 45.5, 43.3, 41.8 (×2), 41.5, 36.4, 36.2, 35.6 (×2), 35.5 (×2), 35.3 (×2), 35.2, 35.1, 34.3, 31.2, 27.7, 27.4, 27.3, 26.2, 26.0, 24.9, 24.3, 23.8, 23.2, 22.6, 22.4, 20.5, 18.8, 18.5, 11.6; IR (film) $v_{max}$ 3173, 3075, 2919, 2848, 1634, 1538, 1331 cm$^{-1}$; CI m/z 861.5965 (MH$^+$, C$_{48}$H$_{77}$N$_8$O$_6$ requires 861.5966).

CH$_2$Cl$_2$ (2:25, 7.5 mL) was added to tert-butyl 3-[(3-{(3β)-cholest-5-en-3-yl[(2-nitrophenyl)sulfonyl]amino}propyl)amino]-3-oxopropylcarbamate (17, 51 mg, 0.064 mmol). After 2 h at 23° C., TLC analysis (MeOH/CH$_2$Cl$_2$, 1:25) revealed conversion to the more polar primary amine. Aqueous NaOH (1 M, 25 mL) was added and the mixture was extracted with CH$_2$Cl$_2$ (2×20 mL). The organic extracts were combined, dried over anhydrous Na$_2$SO$_4$, and solvent was removed in vacuo. CH$_2$Cl$_2$ (10 mL) was added followed by 6-(N-(7-nitrobenz-2-oxa-1,3-diazol-4-yl)amino)hexanoic acid succinimidyl ester (30 mg, 0.077 mmol) and diisopropylethylamine (110 µL, 0.631 mmol). After 8 h at 23° C., aqueous citric acid (10%, 45 mL) was added followed by extraction with CH$_2$Cl$_2$ (2×20 mL). The combined organic extract was dried over anhydrous Na$_2$SO$_4$ and concentrated in vacuo. Flash column chromatography (MeOH/CH$_2$Cl$_2$, 1:50) afforded 23 (58 mg, 92%), mp 86-89° C.; (500 MHz, CDCl$_3$) δ 8.67 (d, J=8.7 Hz, 1H), 7.96 (m, 1H), 7.69 (m, 2H), 7.58 (m, 1H), 7.28 (br s, 1H), 6.66 (br s, 1H), 6.61 (br s, 1H), 6.16 (d, J=8.4 Hz, 1H), 5.16 (br s, 1H), 3.61-3.45 (m, 5H), 3.38-3.32 (m, 4H), 2.46 (t, J=5.5 Hz, 2H), 2.39 (t, J=12.7 Hz, 1H), 2.23 (t, J=7.0 Hz, 2H), 1.98-0.96 (m, 35H), 0.91 (s, 3H), 0.89 (d, J=6.4 Hz, 3H), 0.86 (d, J=2.1 Hz, 3H), 0.84 (d, J=2.1 Hz, 3H), 0.64 (s, 3H); $^{13}$C NMR (125.8 MHz, CDCl$_3$) δ 173.4, 172.3, 148.1, 144.7, 144.5, 144.2, 140.0, 137.0, 133.9, 133.8, 132.0, 130.7, 124.3, 123.1, 122.7, 98.7, 59.3, 56.8, 56.3, 50.1, 44.4, 42.4, 41.8, 39.8, 39.7, 38.4, 37.8, 36.7, 36.6, 36.3, 36.2, 35.9 (×2), 35.8, 31.9, 29.8, 28.6, 28.3, 28.2, 28.0, 27.6, 26.4, 25.0, 24.4, 24.0, 23.0, 22.7, 21.1, 19.5, 18.9, 12.0; IR (film) $v_{max}$

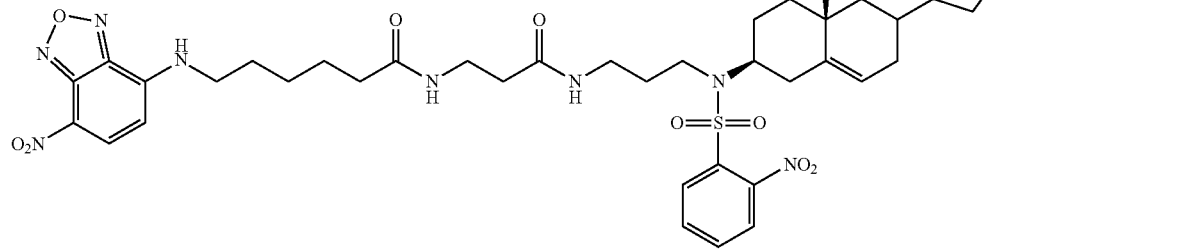

3281, 2937, 2868, 1652, 1587, 1545, 1301 cm$^{-1}$; CI m/z 975.5377 (MH$^+$, C$_{51}$H$_{75}$N$_8$O$_9$S requires 975.5378).

lesteryl-2-nitrobenzenesulfonamide (16, 38 mg, 0.053 mmol) was treated with trifluoroacetic acid in CH$_2$Cl$_2$ (2:25, 10 mL).

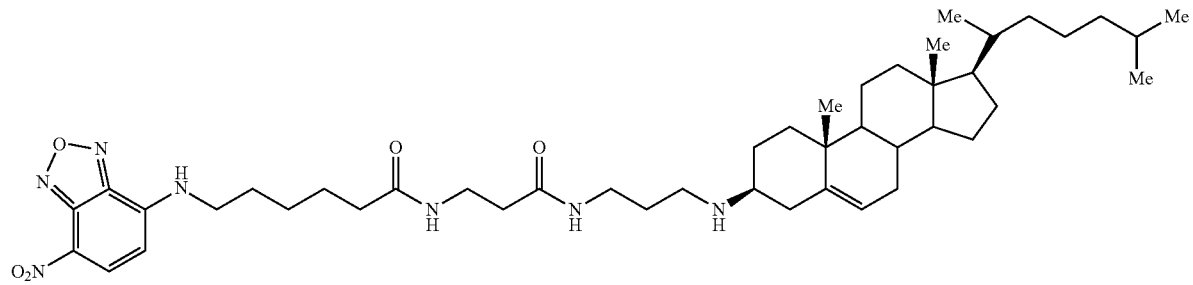

7

N-[3-({3-[(3β)-cholest-5-en-3-ylamino]propyl}amino)-3-oxopropyl]-6-(7-nitrobenzofurazan-4-ylamino)hexanamide (7). To a slurry of N-{3-[(3-{(3β)-cholest-5-en-3-yl[(2-nitrophenyl)sulfonyl]amino}propyl)amino]-3-oxopropyl}-6-(7-nitrobenzofurazan-4-ylamino)hexanamide (23, 58 mg, 0.059 mmol) and K$_2$CO$_3$ (139 mg, 1.008 mmol) in N,N-dimethylformamide (8 mL) and tetrahydrofuran (2 mL), was added thiophenol (61 μL, 0.590 mmol). After 18 h at 23° C., the suspension was filtered and solvent removed in vacuo. The crude product was purified by preparative reverse-phase HPLC (gradient: 59.9% MeCN, 40% H$_2$O, and 0.1% TFA to 99.9% MeCN, 0% H$_2$O, and 0.1% TFA over 10 min; retention time=7.6 min) to afford 7 (15 mg, 32%) mp 101-104° C.; $^1$H NMR (500.13 MHz, CDCl$_3$) δ 9.54 (br s, 1H), 8.50 (d, J=8.9 Hz, 1H), 8.42 (br s, 1H), 8.01 (t, J=5.7, 1H), 7.82 (t, J=5.7 Hz, 1H), 6.39 (d, J=6.4 Hz, 1H), 5.36 (d, J=4.7 Hz, 1H), 3.43 (m, 1H), 3.22 (m, 1H), 3.11 (m, 2H), 2.93-2.84 (m, 3H), 2.39-2.28 (m, 2H), 2.22 (t, J=7.0 Hz, 2H), 2.04 (t, J=7.4 Hz, 2H), 1.97-0.94 (m, 36H), 0.92 (s, 3H), 0.86 (d, J=6.5 Hz, 3H), 0.84 (d, J=2.4 Hz, 3H), 0.82 (d, J=2.4 Hz, 3H), 0.61 (s, 3H); $^{13}$C NMR (125 MHz, DMSO d$_6$) δ 171.9, 170.9, 145.1, 144.4, 144.1, 138.5, 137.9 122.4, 120.5, 99.0, 56.6, 56.0, 55.5, 49.3, 43.3, 41.8 (×2), 41.6, 40.5, 36.4, 36.1 (×2), 35.6, 35.5 (×2), 35.3, 35.2, 35.1, 34.3, 31.2, 27.7, 27.4, 27.3, 26.3, 26.0, 24.9, 24.4, 23.8, 23.2, 22.6, 22.4, 20.4, 18.7, 18.5, 11.6; IR (film) ν$_{max}$ 3257, 3093, 2940, 2858, 1636, 1548, 1377 cm$^{-1}$; CI m/z 790.5605 (MH$^+$, C$_{45}$H$_{72}$N$_7$O$_5$ requires 790.5595).

After 2 h at 23° C., TLC analysis (MeOH/CH$_2$Cl$_2$, 1:50) revealed conversion to the more polar primary amine. Aqueous NaOH (1 M, 20 mL) was added, and the mixture was extracted with CH$_2$Cl$_2$ (3×20 mL). The organic extracts were combined, dried over anhydrous Na$_2$SO$_4$, and solvent was removed in vacuo. CH$_2$Cl$_2$ (10 mL) was added followed by 6-(N-(7-nitrobenz-2-oxa-1,3-diazol-4-yl)amino)hexanoic acid succinimidyl ester (25 mg, 0.063 mmol) and diisopropylethylamine (92 μL, 0.529 mmol). After 8 h at 23° C., aqueous citric acid (10%, 50 mL) was added followed by extraction with CH$_2$Cl$_2$ (2×20 mL). The organic extracts were combined, dried over anhydrous Na$_2$SO$_4$, and solvent removed in vacuo. Flash column chromatography (MeOH/CH$_2$Cl$_2$, 1:50) afforded 22 (32 mg, 67%), mp 77-79° C.; $^1$H NMR (500 MHz, CDCl$_3$) δ 8.38 (d, J=8.7 Hz, 1H), 7.96 (m, 1H), 7.68 (m, 2H), 7.57 (m, 1H), 7.16 (br s, 1H), 6.42 (m, 1H), 6.15 (d, J=8.44 Hz, 1H), 5.14 (d, J=3.3 Hz, 1H), 3.60-3.45 (m, 3H), 3.38-3.34 (m, 4H), 2.39 (t, J=12.4 Hz, 2H), 2.25 (t, J=7.1 Hz, 2H), 1.97-0.93 (m, 34H), 0.90 (s, 3H), 0.87 (d, J=6.4 Hz, 3H), 0.84 (d, J=2.2 Hz, 3H), 0.83 (d, J=2.2 Hz, 3H), 0.62 (s, 3H); $^{13}$C NMR (125.8 MHz, CDCl$_3$) δ 173.3, 148.0, 144.6, 144.4, 144.1, 140.0, 137.0, 133.8 (×2), 131.9, 130.6, 124.2, 123.0, 122.5, 99.0, 59.3, 56.7, 56.2, 50.1, 43.9, 42.4, 41.7, 39.7, 39.6, 38.4, 37.7, 36.7, 36.4, 36.3 (×2), 35.8, 31.9, 31.8, 31.6, 28.3, 28.1, 28.0, 27.6, 26.4, 25.0, 24.3, 23.9, 22.9, 22.7,

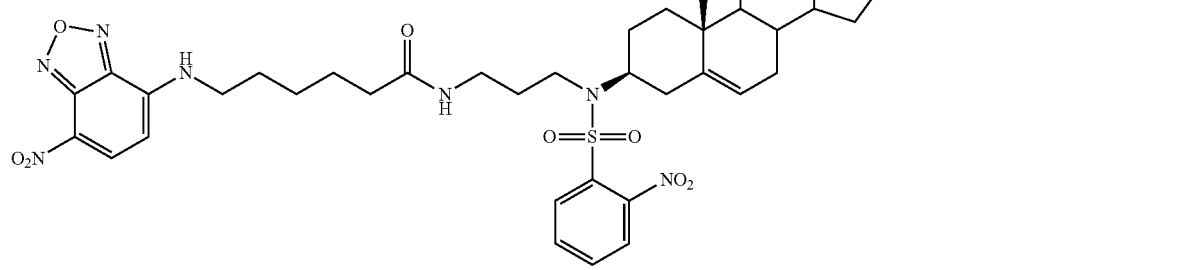

22

N-(3-{(3β)-cholest-5-en-3-yl[(2-nitrophenyl)sulfonyl]amino}propyl)-6-(7-nitrobenzofurazan-4-ylamino)hexanamide (22). N-[3-(tert-butoxycarbonylamino)propyl]-N-cho- 20.9, 19.4, 18.8, 11.9; IR (film) ν$_{max}$ 3299, 2928, 2851, 1738, 1586, 1545, 1301 cm$^{-1}$; CI m/z 904.5021 (MH$^+$, C$_{48}$H$_{70}$N$_7$O$_8$S requires 904.5007).

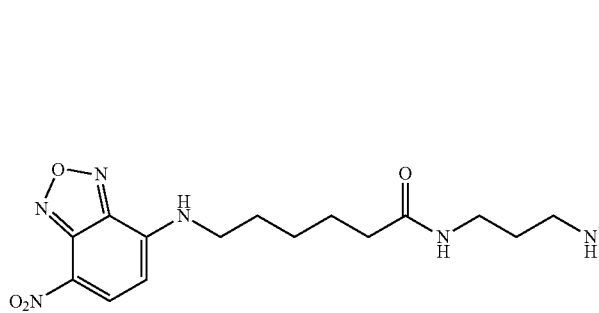 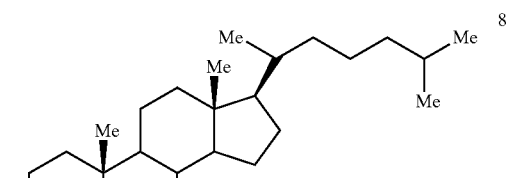

N-{3-[(3β)-cholest-5-en-3-ylamino]propyl}-6-(7-nitrobenzofurazan-4-ylamino)hexanamide (8). To a slurry of N-(3-{(3β)-cholest-5-en-3-yl[(2-nitrophenyl)sulfonyl]amino}propyl)-6-(7-nitrobenzofurazan-4-ylamino)hexanamide (22, 88 mg, 0.097 mmol) and K$_2$CO$_3$ (134 mg, 0.970 mmol) in N,N-dimethylformamide (8 mL) and tetrahydrofuran (2 mL), was added thiophenol (79 μL, 0.767 mmol). After 18 h at 23° C., the suspension was filtered and solvent removed in vacuo. Purification by preparative reverse-phase HPLC (gradient: 69.9% MeCN, 30% H$_2$O, and 0.1% TFA to 99.9% MeCN, 0% H$_2$O, and 0.1% TFA over 10 min; retention time=7.7 min) afforded 8 (20 mg, 29%) mp 78-80° C.; $^1$H NMR (500 MHz, DMSO d$_6$) δ 9.54 (br s, 1H), 8.50 (d, J=8.8 Hz, 1H), 8.43 (br s, 1H), 7.99 (t, J=5.8, 1H), 6.38 (d, J=9.0 Hz, 1H), 5.34 (br s, 1H), 3.43 (m, 1H), 3.11 (m, 2H), 2.94-2.81 (m, 3H), 2.30 (m, 2H), 2.09 (t, J=7.3 Hz, 2H), 1.92-0.94 (m, 35H), 0.90 (s, 3H), 0.87 (d, J=6.4 Hz, 3H), 0.84 (d, J=2.4 Hz, 3H), 0.83 (d, J=2.4 Hz, 3H), 0.60 (s, 3H); $^{13}$C NMR (125.8 MHz, DMSO d$_6$) δ 172.7, 145.1, 144.4, 144.1, 138.5, 137.9 122.4 (×2), 99.0, 56.6, 56.0, 55.5, 49.3, 43.3, 41.8, 41.7, 41.6, 36.4, 36.1, 35.6, 35.4, 35.1 (×2), 34.3, 31.2 (×2), 27.7, 27.4, 26.3, 26.1, 24.9, 24.4, 23.8, 23.7, 23.1, 22.6, 22.4, 20.4, 18.7, 18.5 (×2), 11.6; IR (film) ν$_{max}$ 3269, 2949, 2868, 1649, 1585, 1530, 1300 cm$^{-1}$; CI m/z 719.5224 (MH$^+$, C$_{42}$H$_{67}$N$_6$O$_4$ requires 719.5224).

0.194 mmol, prepared as previously reported[6]) was added trifluoroacetic acid in CH$_2$Cl$_2$, (2:25, 10 mL). After 2 h at 23° C., TLC analysis (MeOH/CH$_2$Cl$_2$, 1:20) revealed conversion to the more polar primary amine. Aqueous NaOH (1 M, 20 mL) was added followed by extraction with CH$_2$Cl$_2$ (2×35 mL). The organic extracts were combined, dried over anhydrous Na$_2$SO$_4$, and solvent was removed in vacuo. CH$_2$Cl$_2$ (15 mL), 6-(N-(7-nitrobenz-2-oxa-1,3-diazol-4-yl)amino)hexanoic acid succinimidyl ester (68 mg, 0.174 mmol), and diisopropylethylamine (338 μL, 1.940 mmol) were added. After 6 h at 23° C., aqueous citric acid (10%, 30 mL) was added followed by extraction with CH$_2$Cl$_2$ (2×35 mL). The organic extracts were combined, dried over anhydrous Na$_2$SO$_4$, and solvent removed in vacuo. Flash column chromatography (MeOH/CH$_2$Cl$_2$, 1.5:100) afforded 9 (103 mg, 81%), mp 72-74° C.; $^1$H NMR (500 MHz, CDCl$_3$) δ 8.43 (d, J=8.7 Hz, 1H), 7.30 (br s, 1H), 6.80 (br s, 1H), 6.15 (d, J=7.9, 1H), 6.04 (d, J=7.2 Hz, 1H), 3.57-3.52 (m, 2H), 3.44 (m, 1H), 2.44 (t, J=5.4 Hz, 2H), 2.22 (t, J=7.1 Hz, 2H), 1.83-1.66 (m, 8H), 1.55-0.93 (m, 29H), 0.98 (s, 3H), 0.87 (d, J=6.6 Hz, 3H), 0.84 (d, J=2.1 Hz, 3H), 0.82 (d, J=2.1 Hz, 3H), 0.67 (s, 3H); $^{13}$C NMR (125.8 MHz, CDCl$_3$) δ 173.1, 171.3, 144.5, 144.4, 144.2, 136.9 (×2), 123.2, 107.8, 98.6, 56.3, 56.2, 52.2, 47.5, 42.9, 42.8, 40.1, 39.6, 36.5, 36.2 (×2), 35.9 (×2), 35.8, 35.3, 33.3, 30.9, 28.3, 28.1, 26.4, 26.2, 25.0, 24.9, 24.4, 23.9, 22.9,

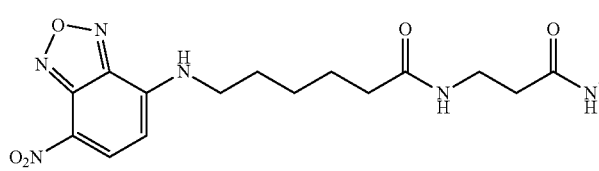 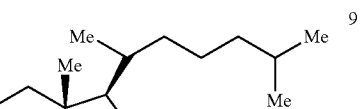

N-{3-[(3β)-cholest-5-en-3-ylamino]-3-oxopropyl}-6-(7-nitrobenzofurazan-4-ylamino)hexanamide (9). To 3-(tert-butoxycarbonylamino)-N-cholesterylpropionamide (108 mg, 22.7 (×2), 20.1, 18.8, 12.4, 11.9; IR (CDCl$_3$) ν$_{max}$ 3269, 2949, 2868, 1649, 1620, 1584, 1530, 1300 cm$^{-1}$; CI m/z 733.5004 (MH$^+$, C$_{42}$H$_{65}$N$_6$O$_5$ requires 733.5016).

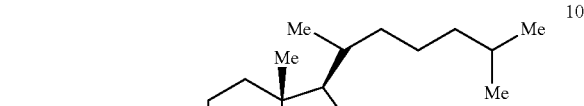
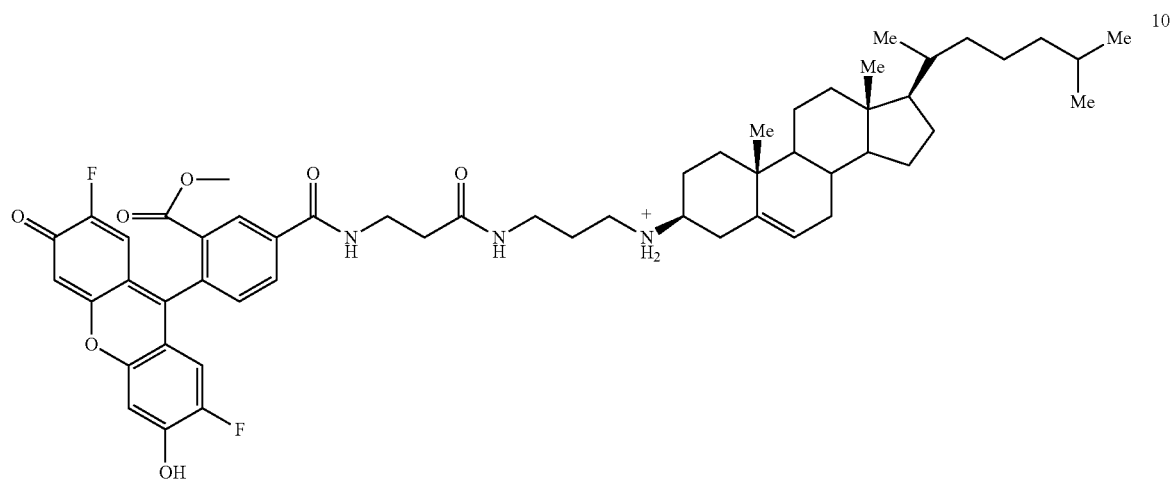

5-({[3-({3-[(3β-cholest-5-en-3-ylamino]propyl}amino)-3-oxopropyl]amino}carbonyl)-2-(2,7-difluoro-6-hydroxy-3oxo-3H-xanthene-9-yl)benzoate (10). Trifluoroacetic acid in CH$_2$Cl$_2$ (2:25, 2 mL) was added to tert-butyl 3-[(3-{(3β)-cholest-5-en-3-yl[(2-nitrophenyl)sulfonyl]amino}propyl)amino]-3-oxopropylcarbamate (17, 11 mg, 0.014 mmol). After 2 h at 23° C., TLC analysis (MeOH/CH$_2$Cl$_2$, 1:25) revealed conversion to the more polar primary amine. Aqueous NaOH (1 M, 5 mL) was added and the mixture was extracted with CH$_2$Cl$_2$ (2×10 mL). The organic extracts were combined, dried over anhydrous Na$_2$SO$_4$, and solvent was removed in vacuo. DMF (5 mL) was added followed by 5-carboxyoregon green succinimidyl ester (5 mg, 0.010 mmol). To this solution was added diisopropylethylamine (5 µL, 0.028 mmol). After stirring at 23° C. for 20 h, the reaction mixture was concentrated in vacuo. The product was purified by preparative reverse-phase HPLC (gradient: 89.9% CH$_3$CN, 10% ddw, and 0.1% TFA to 98.9% CH$_3$CN, 1% ddw, and 0.1% TFA over 10 min followed by isocratic at 98.9% CH$_3$CN, 1% ddw, and 0.1% TFA for an additional 10 min; retention time=16.2 min (215 nm)) to yield an orange oil (5.5 mg, 50%) corresponding to the nosyl-protected precursor. CI m/z 1093.4837 (MH$^+$, C$_{60}$H$_{70}$F$_2$N$_4$O$_{11}$S requires 1093.4809). To a slurry of this nosyl-protected precursor (5.5 mg, 0.005 mmol) was added K$_2$CO$_3$ (7.0 mg, 0.050 mmol), DMF (2 mL), and thiophenol (2.8 mg, 0.025 mmol). This mixture was stirred at 23° C. for 16 h, filtered, and solvent removed in vacuo to yield a crude solid that was purified by preparative reverse-phase HPLC (gradient: 89.9% CH$_3$CN, 10% ddw, and 0.1% TFA to 98.9% CH$_3$CN, 1% ddw, and 0.1% TFA over 10 min followed by isocratic at 98.9% CH$_3$CN, 1% ddw, and 0.1% TFA for an additional 10 min; retention time=11.6 min (215 nm)) to yield an orange oil (3.1 mg, 69%). $^1$H NMR (CDCl$_3$:CD$_3$OD, 8:2, 400 MHz) δ 8.38 (s, 1H), 8.14 (d, J=7.4 Hz, 1H), 7.20 (d, J=7.9 Hz, 1H), 6.84-6.70 (m, 2H), 6.34-6.28 (m, 2H), 5.36 (s, 1H), 3.72-3.62 (m, 2H), 3.11-3.05 (m, 2H), 2.96-2.90 (m, 2H), 2.88-2.76 (m, 1H), 2.57-2.48 (m, 2H), 2.40-2.31 (m, 2H), 1.98-0.79 (m, 40H), 0.60 (s, 3H); CI m/z 908.5085 (MH$^+$, C$_{54}$H$_{68}$F$_2$N$_3$O$_7$ requires 908.5026).

Synthesis of a fluorescent DNP-derived probe for fluorescence polarization assays. The synthesis of fluorescent probe 27 is outlined in Scheme S1. This fluorescent probe (27) was employed to determine the apparent affinity of DNP for rabbit polyclonal anti-DNP IgG by fluorescence polarization.

Scheme S1.

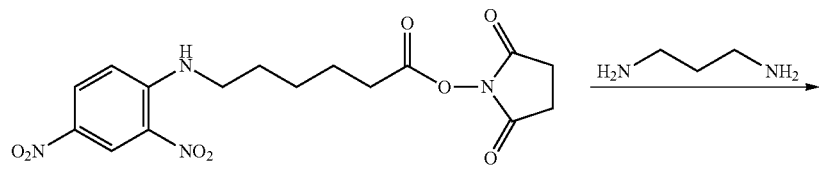

25

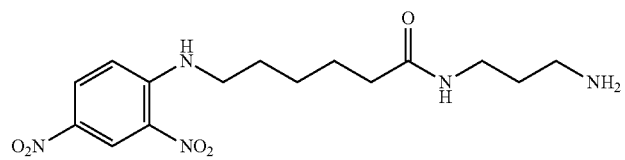

26

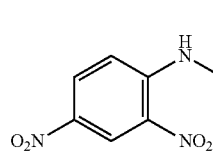
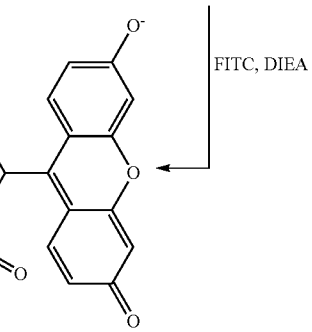

27

3-aminopropyl-6-[(2,4-dinitrophenyl)amino]hexanamide (26). 6-(2,4-dinitrophenyl)aminohexanoic acid succinimidyl ester (200 mg, 0.510 mmol) was added to 1,3-diaminopropane (8.6 mL, 102.09 mmol). After 1 h at 23° C., aqueous NaOH (1 M, 200 mL) was added followed by extraction with $CH_2Cl_2$ (5×50 mL). The organic extracts were combined and washed with 1 M HCl (5×50 mL). The acidic aqueous layers were combined, rendered basic to litmus with aqueous NaOH (1 M), and extracted with dichloromethane (5×50 mL). The combined organic extracts were dried over anhydrous $Na_2SO_4$, and solvent was removed in vacuo to afford 26 as a dark orange oil (93 mg, 53%). $^1H$ NMR ($CDCl_3/CD_3OD$, 8:2, 300 MHz) δ 8.95 (d, J=2.7 Hz, 1H), 8.49 (t, J=4.7 Hz, 1H), 8.14 (dd, J=2.7 Hz, J=9.6 Hz, 1H), 7.08-7.00 (m, 1H), 6.87 (d, J=9.6 Hz, 1H), 3.38-3.29 (m, 2H), 3.22-3.16 (m, 2H), 2.63 (t, J=6.7 Hz, 2H), 2.13 (t, J=7.4 Hz, 2H), 1.75-1.51 (m, 6H), 1.44-1.36 (m, 2H); $^{13}C$ NMR (75.4 MHz) δ 173.7, 148.3, 135.6. 130.3, 130.0, 124.2, 114.1, 43.2, 38.7, 36.6, 36.0, 31.7, 28.3, 26.4, 25.1; IR (film) $v_{max}$ 3413, 3321, 2937, 2868, 1702, 1655, 1546, 1367 cm$^{-1}$; CI m/z 354.1756 (MH$^+$, $C_{15}H_{24}N_5O_5$ requires 354.1772).

N-{3-[5-fluoresceinisothiourea]propyl-6-[(2,4-dinitrophenyl)amino]hexanamide (27). To 3-aminopropyl-6-[(2,4-dinitrophenyl)amino]hexanamide (26, 45 mg, 0.128 mmol) in THF/MeOH (3:2, 5 mL) was added 5-fluorescein isothiocyanate (55 mg, 0.141 mmol) and diisopropylethylamine (44 μL, 0.253 mmol). After stirring at 23° C. for 20 h, solvent was removed in vacuo, and the crude product was purified by preparative reverse-phase HPLC (gradient: 9.9% MeCN, 90% $H_2O$, and 0.1% TFA to 98.9% MeCN, 1% $H_2O$, and 0.1% TFA over 40 min; retention time=15.0 min). The product was lyophilized from water to yield 27 as an orange solid (61 mg, 64%), mp 136-139° C. $^1H$ NMR ($CDCl_3/CD_3OD$, 8:2, 360 MHz) δ 8.88d, J=2.7 Hz, 1H), 8.14 (d, J=1.9 Hz, 1H), 8.04 (dd, J=2.7 Hz, J=9.6 Hz, 1H), 7.79 (dd, J=2.0 Hz, J=8.3 Hz, 1H), 6.99 (d, J=8.3 Hz, 1H), 6.92 (d, J=9.0 Hz, 2H), 6.79 (m, 3H), 6.63 (dd, J=2.2 Hz, J=9.0 Hz, 2H), 3.50 (t, J=5.8 Hz, 2H), 3.24 (t, J=7.1 Hz, 2H), 3.15-3.13 (m, 1H), 3.09 (t, J=6.2 Hz, 2H), 2.06 (t, J=7.3 Hz, 2H), 1.66-1.47 (m, 6H), 1.34-1.25 (m, 2H); $^{13}C$ NMR (75.4 MHz) δ 181.1, 174.4, 168.5, 164.1 (×2), 155.2 (×2), 148.3 (×2), 141.1, 135.6, 130.6 (×2), 130.3 (×2), 130.0, 129.0, 126.6, 124.2 (×2), 121.7, 115.4 (×2), 114.2 (×2), 112.6, 102.6 (×2), 43.1, 41.1, 36.1, 36.0, 28.6, 28.3, 26.3, 25.2; IR (film) $v_{max}$ 3318, 3097, 2936, 2860, 2502, 1619, 1584 cm$^{-1}$; CI m/z 743.2184 (MH$^+$, $C_{36}H_{35}N_6O_{10}S$ requires 743.2130).

Example 6

Biological Assays

Cell culture. Jurkat lymphocytes (acute T-cell leukemia, ATCC #TIB-152) were maintained in Roswell Park Memorial Institute (RPMI) 1640 media supplemented with Fetal Bovine Serum (FBS, 10%), penicillin (100 units/mL), and streptomycin (100 μg/mL). RPMI media used for cell culture and wash steps contained antibiotics and FBS unless otherwise noted. OPTI-MEM media employed for transfection was not supplemented with FBS or antibiotics.

Microscopy. Confocal laser scanning microscopy (FIG. 8, FIG. 11, and FIG. 7) employed an Olympus FV300 microscope fitted with a UplanFl objective (60×). Alexa Fluor 488 was excited with a 488 nm Argon ion laser and emitted photons were collected through 510 nm LP and 530 nm SP filters. Excitation of Alexa Fluor 594 and BODIPY TR ceramide employed a 543 nm He—Ne laser and a 565 nm LP filter. Epifluorescence micrographs (FIG. 9 and FIG. 10) were captured through a Zeiss Fluar (100×) objective by a Zeiss Axiocam digital camera interfaced to a Zeiss Axiovert S 100TV microscope. Fluorophores were excited with FITC/Bodipy (Ex. 480/40, Em. 535/50) or Texas Red (Ex. 560/55, Em. 645/75) filter sets (Chroma). Images were processed with Adobe Photoshop 7.0.

Flow cytometry. Analyses were performed with Beckman-Coulter XL-MCL bench-top and EPICS Elite flow cytometers. Forward-scatter (FS) and side-scatter (SSC) dot plots afforded cellular physical properties of size and granularity that allowed gating of live cells. After gating, 10,000 cells were counted. For studies of uptake of anti-DNP/PrA-AF488 mediated by receptors 2-5, AF-488 was excited at 488 nm with a 15 mW air-cooled argon-ion laser, the emission was split with a 550 nm dichroic and filtered through a 510 nm long pass filter and 530/30-nm band pass filter using the XL-MCL cytometer. The PMT voltage for this instrument was set to 724 for detection of AF488. Calibration with Sphero Rainbow Calibration particles (Spherotech) bearing 330,000 molecules of fluorescein/particle provided a fluorescence of 15.6 at this voltage. For studies of uptake of anti-DNP/PrA-AF633 mediated by the green fluorescent NBD-derived receptors 6-9, the EPICS Elite cytometer was employed. Fluorescence detection was derived from simultaneous excitation at 488 nm and 633 nm. A 550 nm dichroic long pass filter split the emission, sending the green light to PMT2, which was interfaced to an additional 525 nm bandpass filter. The emission passed through a 640 nm longpass dichroic which removed laser light with final filtering through a 675 nm bandpass filter. The PMT voltages for this instrument were set to 724 for AF488 and 660 for AF633. Cells treated with receptors 6-9 alone were used to subtract minimal red fluorescent cross talk (<10%) of the NBD fluorophore.

Figure 8:
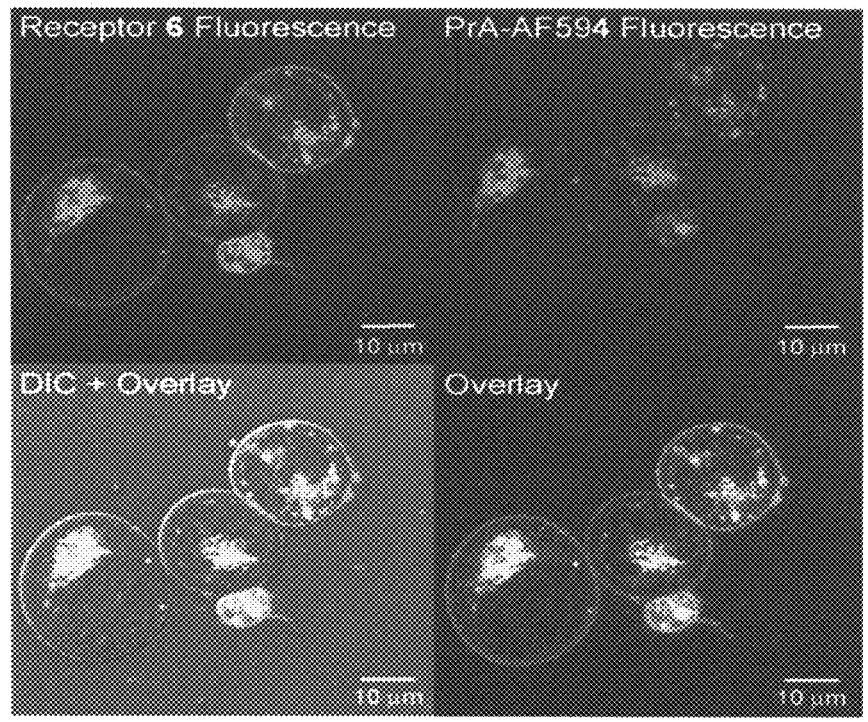
FIG. 8. Synthetic receptor-mediated uptake of protein ligands in Jurkat lymphocytes. Cells were pretreated with receptors for one hour at 37° C. prior to addition of an anti-DNP IgG/PrA complex. Panel A. Confocal laser scanning and differential interference contract (DIC) microscopy of cells treated with green fluorescent receptor 6 (10 μM) followed by the addition of red anti-DNP/PrA-AF594 (for 4 hours). Yellow pixels indicate the localization of green and red fluorophores. Panel B: Dose-dependent magnitude of uptake of anti-DNP/PrA-AF488 quantified by flow cytometry after 4 hours. Right: Competitive inhibition of this uptake (mediated by receptor 2, 1 μM) by addition of 6-(2,4-dinitrophenyl) aminohexanoic acid (DNP-CO2H). Panel C: Kinetics of uptake of anti-DNP/PrA-AF488 quantified by flow cytometry. Left: Relative differences in receptor uptake rates quantified by accumulation of cellular fluorescence. Right: Determination of the rate and half-life of ligand internalization mediated by receptor 2 at 1 μM.
Figure 8:
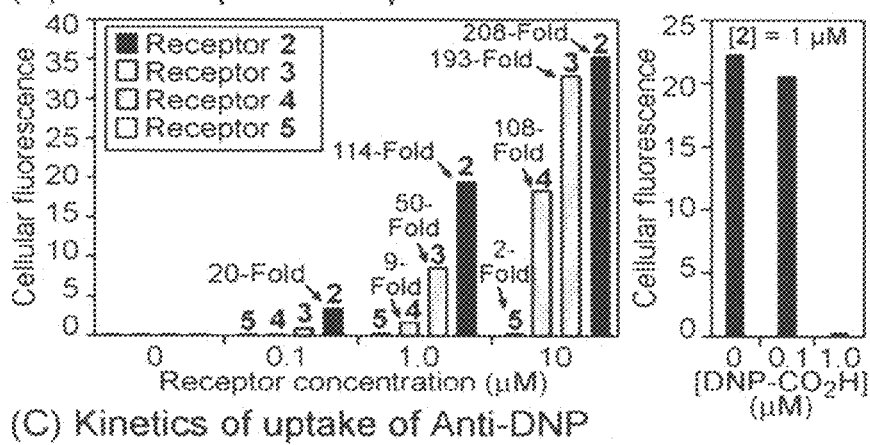
Figure 8:
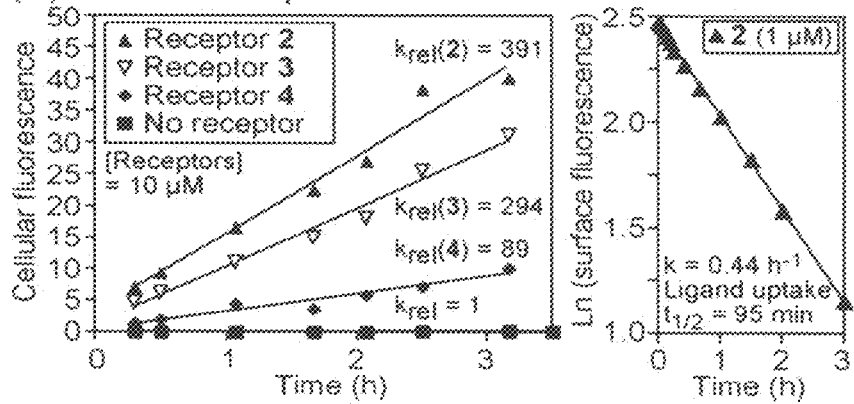
Figure 11:
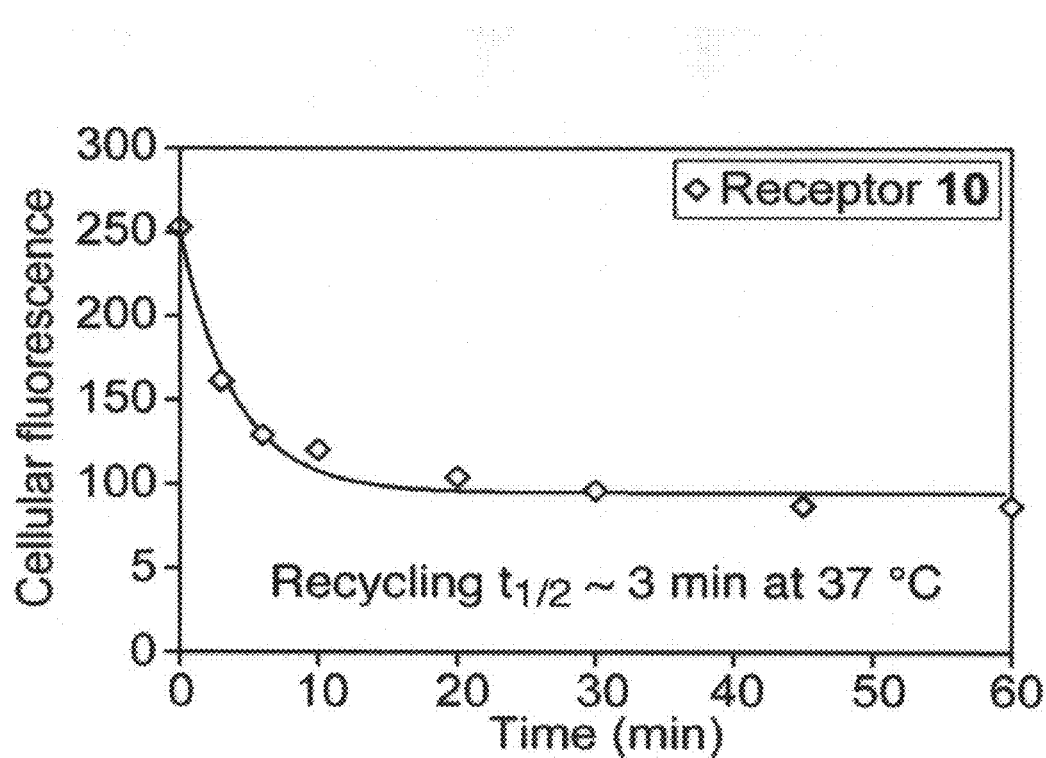
FIG. 11. Quantification of efflux kinetics of receptor 10 from endosomes to the plasma membrane of Jurkat lymphocytes by back exchange. Cells treated with 10 (1 μM, 1 hour) were cooled to 4° C. and cell surface fluorophores removed (>90%) by repeated washing with ice-cold back exchange media containing BSA (1%) and methyl-β-cyclodextrin (2 mM). Cells were resuspended in back exchange media at 37° C. to resume recycling, cellular fluorescence was quantified by flow cytometry, and loss of fluorescence was evaluated with a one-site exponential decay model.

Antibody uptake assays (FIG. 8, Panels A-B, FIG. 10, and FIG. 11). Synthetic receptors 2-9 in DMSO were diluted in RPMI media (0.5 mL, final DMSO concentration=1%) containing Jurkat lymphocytes ($1 \times 10^6$). These receptor-treated cells were incubated at 37° C. for 1 h, washed with RPMI media (2×0.5 mL) to remove unincorporated receptors/DMSO, and resuspended in fresh media (89 µL). To these cells was added a pre-equilibrated complex (preincubated at 23° C. for 1 h) of anti-DNP IgG (9.6 µg) and the PrA-Alexa Fluor conjugate (PrA-AF488 or PrA-AF633, 3 µg) in phosphate-buffered saline (11 µL, pH 7.4, total volume=100 µL). Cells were typically maintained at 37° C. for 4 h to promote synthetic receptor-mediated endocytosis. Prior to analysis, treated cells were washed with media (0.5 mL), washed again with media containing 6-(2,4-dinitrophenyl)aminohexanoic acid (100 µM, 3×0.5 mL×20 min, 1% DMSO) to compete away any non-internalized protein, washed again with media (0.5 mL), and resuspended in media (0.6 mL) for analysis by epifluorescence microscopy, confocal microscopy, or flow cytometry. For the competitive inhibition of uptake experiments shown to the right of FIG. 8, Panel B, 6-(2,4-dinitrophenyl)aminohexanoic acid was preincubated with the anti-DNP IgG/PrA-AF488 complex (23° C. for 1 h in phosphate-buffered saline) prior to addition to cells treated with receptor 2 (1 µM).

Antibody uptake kinetics (FIG. 8, Panel C). To determine the relative uptake rates shown on the left of FIG. 8C, Jurkat lymphocytes were subjected to the antibody uptake assay (cells were treated with receptors 2-5 at 10 µM for 1 h followed by addition of a pre-equilibrated complex (preincubated at 23° C. for 1 h) of anti-DNP-IgG/PrA-AF488 for 15 min to 4 h) and internalized cellular fluorescence was quantified by flow cytometry. Doubling the concentration of pre-equilibrated anti-DNP-IgG/PrA-AF488 did not affect the rate or magnitude of uptake (data not shown), indicating that synthetic receptors were saturated under these conditions. Observed rates of ligand uptake ($L_{obs}$) were calculated with a Michaelis-Menten kinetic model assuming saturating concentrations of substrate ($k_{obs}=(F_t-F_0)/t$). t=time (in minutes), $F_t$=fluorescence at the specified time, and $F_0$=fluorescence at time=0 min. The slope of plots of fluorescence vs. time provided $k_{obs}$ values that were divided by the basal rate of endocytosis (no receptor) to determine the relative rates of uptake.

The rate constant and the ligand internalization half-life shown on the right of FIG. 8C were determined by treatment of Jurkat lymphocytes (in RPMI media, 500 µL) with receptor 2 (1 µM) for 1 h at 37° C. These cells were washed with ice-cold media (500 µL) and maintained at 4° C. A pre-equilibrated (1 h at 23° C.) ice-cold solution of RPMI media (100 µL) containing anti-DNP-IgG (7.2 µg) and PrA-AF488 (2 µg) was added. After 1 h at 4° C., the cells were washed with ice-cold RPMI media (2×500 µL). Cells were equilibrated at 37° C. for 20 min prior to fluorescence measurements to dissociate excess surface-bound antibody. After equilibration, uptake experiments were initiated (this was defined as t=0 min). Cells were subsequently incubated at 37° C. for fixed periods of time (0 to 3 h), cooled to 4° C. on ice, and washed with ice-cold RPMI media containing 6-(2,4-dinitrophenyl)aminohexanoic acid (100 µM, 1% DMSO, 3×0.5 mL×10 min at 4° C. followed by 2×0.5 mL×20 min at 23° C.) to remove non-internalized IgG. Intracellular fluorescence was quantified by flow cytometry. Cell surface fluorescence was calculated by subtracting this intracellular fluorescence from cellular fluorescence measured at t=0 min (after the initial equilibration at 37° C. for 20 min; the competition with 6-(2,4-dinitrophenyl)aminohexanoic acid was omitted to analyze this cellular fluorescence). Curve fitting of the natural log of the calculated cell surface fluorescence against time revealed a linear relationship ($r^2$=0.9991) indicating first order kinetics. The absolute value of the slope provided the rate of uptake (k=0.007327±0.000006 min$^{-1}$), and the ligand internalization half-life ($t_{1/2}$=95 min) was calculated as (ln 2)/k.

Figure 9:
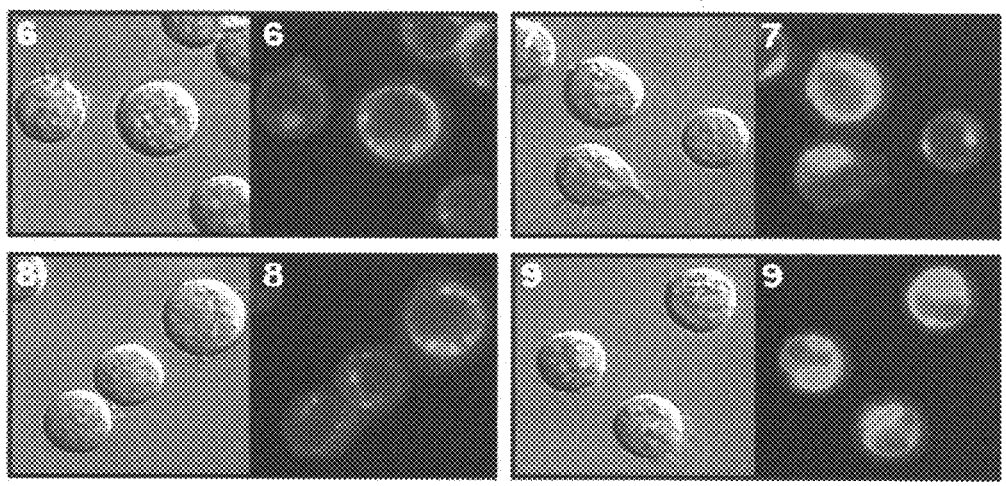
FIG. 9 Subcellular localization of synthetic receptors in living Jurkat lymphocytes. Panel A: DIC (left images) and epifluorescence micrographs (right images) of cells treated for 1 hour with green fluorescent receptors 6-9 (10 μM). Panel B: Quantification of cell surface fluorescence by sodium dithionite quenching of exposed fluorophores. Cells treated as shown in Panel A were washed with sodium dithionite (5 mM) for 10 seconds at 22° C. and residual fluorescence quantified by flow cytometry. Panel C: Quantification of the cellular half-life of receptor 2. Cells were treated with 2 (10 μM) for 1 hour, resuspended in receptor-free media for the times indicated, and 2 was detected on the cell surface with anti-DNP/PrA-AF488.
Figure 9:
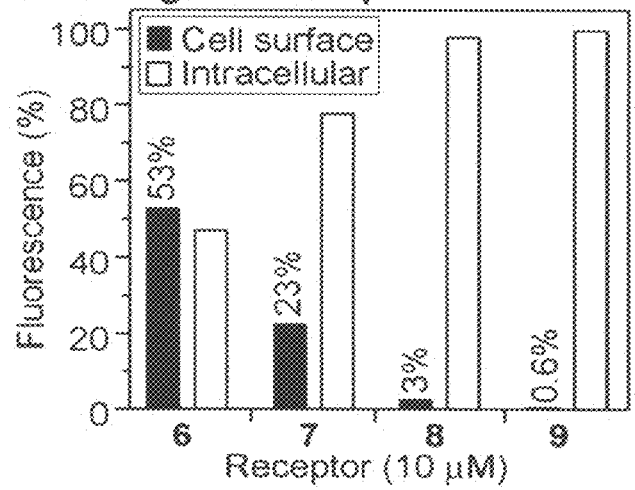
Figure 9:
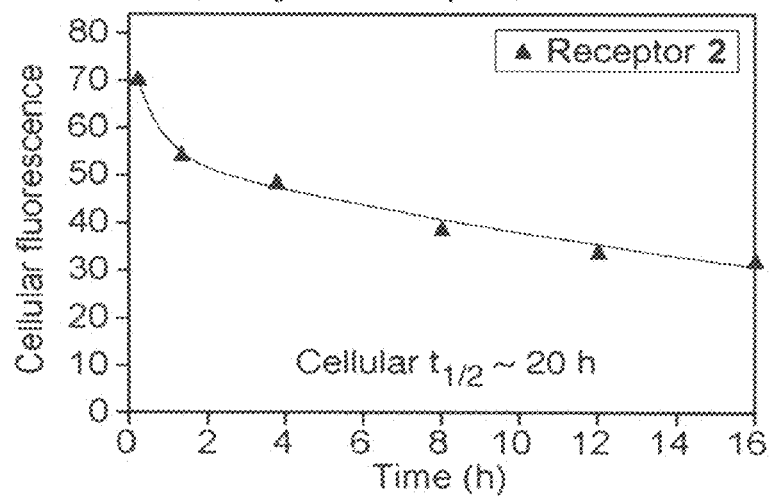

Quantification of the percentage of receptors 6-9 on the cell surface (FIG. 9, Panel B). Jurkat lymphocytes in media ($1 \times 10^6$, 0.5 mL, 1% DMSO) were incubated with receptors 6-9 (10 µM) for 1 h at 37° C. Cells were washed with media (0.5 mL), resuspended in media (0.5 mL), and divided into two equal portions. One portion was treated with sodium dithionite ($Na_2S_2O_4$, 5 mM) in media (0.5 mL) for 10 seconds to irreversibly quench cell surface fluorophores. Cells were immediately washed with media (2×0.5 mL), and the fluorescence of the treated portion and control portion was analyzed by flow cytometry. The fluorescence of the treated cells was subtracted from the control (total) cellular fluorescence to determine the population of intracellular and cell surface fluorophores.

Quantification of the cellular stability of receptor 2 (FIG. 9, Panel C). Jurkat lymphocytes ($1 \times 10^7$) were incubated with receptor 2 in media (5 mL, 10 µM receptor, 1% DMSO) for 1 h at 37° C. in a 15 mL aerated centrifuge tube. Cells were washed with media (2×5 mL) to remove unincorporated receptor, resuspended in media (10 mL), transferred to a tissue culture flask (25 cm$^2$), and maintained at 37° C. At fixed time points, an aliquot of this culture (1 mL) was removed from the flask and cells isolated by centrifugation. These cells were resuspended in media (89 µL) and a pre-equilibrated (23° C. for 1 h) complex of anti-DNP IgG (9.6 µg) and PrA488 (3 µg) in phosphate buffered saline (PBS, 11 µL, pH 7.4) was added for 5 min at 37° C. Treated cells were centrifuged (1300 g for 2 min), the supernatant was removed, cells were resuspended in media (0.5 mL), and cellular fluorescence was analyzed by flow cytometry. The loss of cellular fluorescence was fit to the two-phase exponential decay model provided by GraphPad Prism version 3.0 software (plateau=0, GraphPad Software, San Diego, Calif.) to yield the cell surface half-life of 20 h.

Analysis of cycling of fluorescent receptor 6 between endosomes and the cell surface (FIG. 10). Jurkat lymphocytes ($4 \times 10^6$) were suspended in media (2 mL, 1% DMSO) containing receptor 6 (10 µM) and incubated for 1 h at 37° C. Cells were washed with media (2×2 mL), and cooled on ice (2 min) to block plasma membrane recycling. Ice-cold media containing sodium dithionite (30 mM, 1 mL) was added and the cells were maintained at 4° C. for 5 min to irreversibly quench cell surface fluorophores. Cells were washed with serum free recycling media (composition described on page S16, 2×1 mL), resuspended in serum-free recycling media (368 µL), and equally partitioned into four 1.5 mL Eppendorf tubes designated A, B, C, and D. Tubes A and B were incubated at 37° C. for 30 min to allow internalized receptor to return to the cell surface. Tubes C and D were maintained on ice to inhibit recycling. Tubes A and B were cooled on ice (2 min), and a pre-equilibrated complex (preincubated at 23° C. for 1 h) of anti-DNP IgG (5 µg) and PrA633 (2 µg) in phosphate buffered saline (PBS, 8 µL, pH 7.4) was added to tubes A and C. PBS (8 µL, pH 7.4) was added to tubes B and D as control experiments. The four tubes were maintained at 4° C. for an additional 15 min, washed with ice-cold serum free recycling media (1 mL), resuspended in ice-cold serum free recycling media (1 mL), and the fluorescence of bound anti-DNP/PrA-AF633 was analyzed by flow cytometry. The background fluorescence of cells in tubes B and D was subtracted from values obtained from cells in tubes A and C respectively to correct for minor spectral overlap (<10%) of the NBD and AF633 fluorophores.

Quantification of efflux kinetics of receptor 10 from endosomes to the plasma membrane by back exchange (FIG. 11). The efficiency of removal of 10 from the plasma membrane was examined prior to analysis of efflux kinetics. Jurkat lymphocytes ($3\times10^6$) were suspended in ice-cold serum free recycling media (1.5 mL) and maintained on ice (2 min) to block plasma membrane recycling. These cells were resuspended in ice-cold serum free recycling media (1.5 mL, 1% DMSO) containing 10 (1 μM) and maintained on ice (10 min) to allow association of 10 with the plasma membrane. Receptor-treated cells were washed with ice-cold serum free recycling media ($2\times0.5$ mL), resuspended in ice-cold serum free recycling media (1.5 mL), and analyzed by flow cytometry. Cells were isolated by centrifugation, resuspended in ice-cold back-exchange media (serum free recycling media containing 2 mM Me-β-cyclodextrin and 1% BSA, 1.5 mL), maintained on ice (2 min), and analyzed by flow cytometry (this single wash with back-exchange media resulted in a 44% loss of total cellular fluorescence). The cells were maintained on ice, washed again with ice-cold back exchange media ($3\times10$ min$\times$1.5 mL), and analyzed by flow cytometry (this combination of four total wash steps with back-exchange media resulted in a 84% loss of total cellular fluorescence; additional wash steps resulted in >90% removal of receptor from the cell surface).

To determine the half-life of receptor recycling back to the plasma membrane, Jurkat lymphocytes ($3\times10^6$) were resuspended in serum free recycling media containing 10 (1 μM, 1% DMSO, 1.5 mL) and incubated for 10 min at 37° C. These cells were washed with serum free recycling media ($2\times1$ mL) to remove unincorporated receptor (10). These receptor-treated cells were cooled on ice (5 min) to halt recycling and washed with ice-cold back-exchange media ($6\times1.5$ mL$\times$10 min) to selectively remove 10 from the cell surface without affecting the population of 10 in intracellular endosomes. These cells were resuspended in warm back exchange media (37° C., 1.5 mL) to initiate plasma membrane recycling and immediately analyzed by flow cytometry (defined as t=0 min). Cells were isolated by centrifugation, resuspended in warm back exchange media (1.5 mL, 37° C.), incubated at 37° C., and analyzed by flow cytometry as a function of time. The loss of cellular fluorescence was fit to a one-phase exponential decay model using GraphPad Prism version 3.0 software (GraphPad Software, San Diego, Calif.), to yield a recycling half-life of 2.8±0.8 min.

Serum free recycling media. This media was prepared as previously described[7] and included NaCl (150 mM), KCl (5 mM), CaCl$_2$ (1 mM), MgCl$_2$ (1 mM), glucose (2 g/L), and Hepes (20 mM, pH 7.4).

Figure 12:
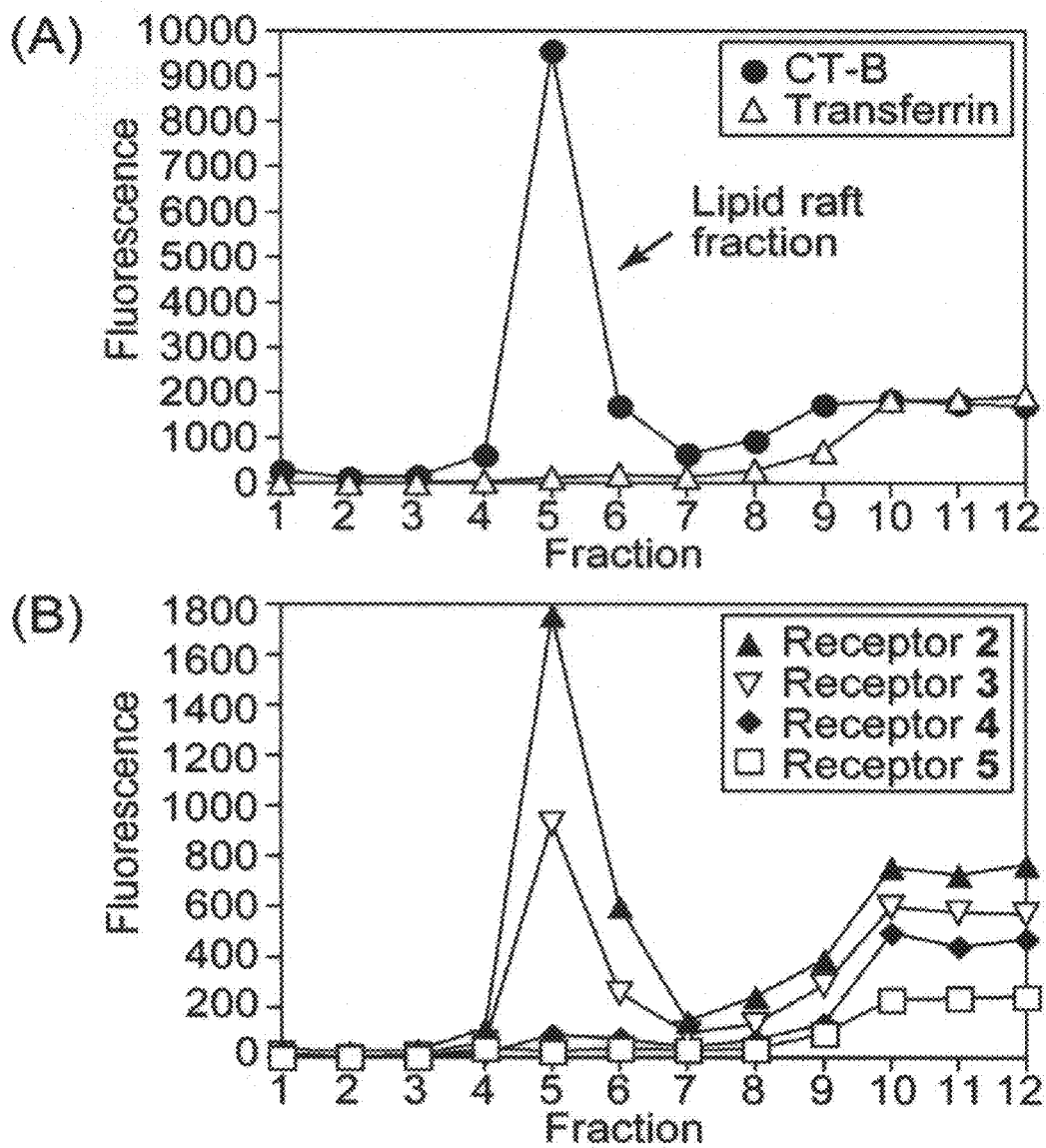
FIG. 12. Association of receptor-ligand complexes with putative lipid raft functions of plasma membranes of Jurkat lymphocytes. Panel A: Cells were treated with AF488-labeled protein ligand for 30 minutes at 4° C. Panel B: Cells were treated with receptors 2-5 (1 μM) for 1 hour at 37° C. followed by anti-DNP-AF488 for 30 minutes at 4° C. Cells fractionated by ultracentrifugation for 20 hours at 4° C. in a 2% to 40% sucrose step gradient containing 0.2% Triton-X. CT-B: Cholera toxin B subunit.

Isolation of lipid rafts by sucrose density gradient ultracentrifugation (FIG. 12). A previously reported[8] method was modified to analyze the association of protein ligands with lipid raft subdomains of cellular plasma membranes. Rabbit polyclonal anti-DNP IgG was directly conjugated to AF488 with a N-hydroxysuccinimidyl ester labeling kit (Molecular Probes). This fluorescent protein was compared with Cholera toxin-AF488 (CT-AF488) and Transferrin-AF488 from Molecular Probes. Jurkat lymphocytes ($1\times10^7$) in 15 mL Corning tubes (5 mL media, 1% DMSO) were incubated with synthetic receptors 2-5 (1 μM) for 1 h at 37° C. These cells were washed with media ($2\times5$ mL) and resuspended in ice-cold media (285 μL). To synthetic receptor-treated cells was added anti-DNP-AF488 conjugate in PBS (15 μL, 1 mg/mL). To control cells was added CT-AF488 or transferrin-AF488 in PBS (15 μL, 1 mg/mL). Cells were maintained at 4° C. for 30 min and washed with ice-cold media ($2\times0.5$ mL). Cells were lysed at 4° C. in an ultracentrifugation tube (ultra clear $14\times89$ mm, Beckmann Instruments) by addition of TNEV lysis buffer (2 mL, 0.2% Triton X-100 (v/v), 150 mM NaCl, 5 mM EDTA, 5 mM Na$_3$VO$_4$, 25 mM Tris-HCl, pH 7.4) followed by vortex mixing for 20 seconds every 20 min for 1 h. This lysate was combined with a solution of 80% sucrose in TNEV lysis buffer (2 mL, w/v) to yield 4 mL of a 40% sucrose solution at the bottom of the ultracentrifugation tube. This 40% sucrose solution was overlayed with 30% sucrose in TNEV lysis buffer (4 mL), followed by 5% sucrose in TNEV lysis buffer (2 mL), and a final solution of 2% sucrose in TNEV lysis buffer (2 mL) by syringe. Masses of ultracentrifugation tubes were balanced to within 1 mg by the addition of 2% sucrose solution in TNEV lysis buffer. Tubes were centrifuged at 33,000 rpm (134,409 g) for 20 h at 4° C. in a Beckman Optima™ LE-80K preparative ultra centrifuge using a SW41 swinging bucket rotor. Fractions ($12\times1$ mL) were harvested by aspiration with a capillary tube and small pump beginning with the highest density fraction at the bottom of the ultracentrifugation tube. The fluorescence of these fractions were quantified with a Packard Fusion microtiterplate reader fitted with a 480 nm excitation filter and 535 nm emission filter.

Fluorescence polarization assays (FIG. 9). Fluorescence polarization binding experiments employed a Packard Fusion microtiterplate reader equipped with a 485 nm excitation filter and a 535 nm polarization emission filter. Apparent dissociation constants for binding of NBD and DNP derivatives to rabbit polyclonal anti-DNP IgG were determined by analyzing a fixed concentration of FITC-DNP (27, 20 nM) or 6-(7-nitrobenzofuran-4-ylamino)hexanoic acid (28, 100 nM) in PBS (pH 7.4, 100 μL). Fluorescent probes were equilibrated for 30 min with varying concentrations of rabbit anti-DNP IgG in black 96 well plates (Costar) prior to fluorescence polarization measurements in triplicate. Dissociation constants were calculated by nonlinear regression using a sigmoidal dose-response model with variable slope (GraphPad Prism 3.0 software). Polarization values for binding of 28 to rabbit anti-DNP were corrected to compensate for partial binding-induced quenching of the NBD fluorophore.[2,3]

Transient Transfection of Jurkat Lymphocytes with EGFP-lgp120 as a green fluorescent marker of late endosomes and lysosomes (FIG. 11). The plasmid vector pEGFP-lgp120[4] (2 μg in 100 μL OPTI-MEM media) was combined with a solution of DMRIE-C (Invitrogen, 2 μL in 100 μL OPTI-MEM) in a single well on a 24-well plate. This solution was incubated at 23° C. for 45 min. Jurkat lymphocytes ($4\times10^5$) resuspended in OPTI-MEM (60 μL) were added to this well with gentle swirling to mix the components. The 24-well plate was incubated at 37° C. in a humidified CO$_2$ incubator for 4 h. RPMI media (400 μL) containing FBS (15%), PHA-L (1 μg/mL), and PMA (5 ng/mL), but no antibiotics, was added to the plate. Maximal transfection efficiency (~40%) was obtained after incubation for 24 to 36 h (37° C., 5% CO$_2$).

Analysis of receptor cytotoxicity. Jurkat lymphocytes were treated with receptor 3 (10 μM) for 1 h followed by Anti-DNP-IgG/PrA488 for 4 h under the antibody uptake assay conditions. These cells were washed twice with media and incubated for an additional 24 h at 37° C. The dead-cell stain propidium iodide (10 μg/mL) was added to cells prior to analysis, and viability was quantified from flow cytometry forward and side-scatter dot plots. Greater than 95% of cells remained viable under these conditions. Additionally, cells were examined after treatment with receptor 2 (10 μM) for 1 h, removal of unincorporated 2 by resuspension in receptor-free cell culture media, and longer-term growth in culture. After an additional 96 h in culture, >90% of these cells remained viable and were morphologically indistinguishable from untreated cells.

Example 7

Kinetics of Ligand Uptake for Synthetic Receptors

Synthetic receptors were evaluated as mediators of cellular uptake of protein ligands in living Jurkat lymphocytes, a human T cell line. Confocal laser scanning microscopy and flow cytometry were employed to analyze cells treated with compounds 2-9 for 1 hour followed by addition of anti-DNP IgG complexed with fluorescent conjugates of the IgG-binding protein A (PrA) from S. aureus. Treatment of cells with green fluorescent NBD derivatives 6 (10 μM) and anti-DNP IgG labeled red fluorescent with PrA-Alexa Fluor-594 (PrA-AF594) revealed that the receptor 6 becomes localized both on the cell surface and embedded in the plasma membrane and in intracellular compartments (FIG. 9, Panel A). Red fluorescent IgG delivered into these intracellular compartments only partially co-localized with receptor 6 suggesting intracellular dissociation of the receptor from the ligand. (FIG. 9, Panel A). This intracellular red fluorescence was 59-fold lower in the absence of receptor 6 consistent with a synthetic receptor-mediated uptake mechanism. The IgG-loaded intracellular compartments were identified as late endosomes and lysosomes by co-localization studies in cells transfected with EGFP-lgp120, a fluorescent protein marker of these compartments. Excess anti-DNP IgG/PrA-AF594 added to cells treated with 6 did not appreciably deplete this receptor from the cell surface despite extensive uptake of this protein complex. These results are consistent with a delivery mechanism involving the binding of IgG/PrA to receptor 6 at the cell surface, internalization of the complex by endocytosis, dissociation of IgG from 6 in acidic endosomes, and return of receptor 6 to the cell surface by plasma membrane recycling.

Example 8

Efficiency of Uptake Mediated by the DNP-Based Receptors 2-5

To investigate the efficiency of uptake mediated by the higher affinity DNP-based receptors 2-5, the magnitude and kinetics of delivery of a green fluorescent anti-DNP/PrA-AF488 complex was quantified by flow cytometry as shown in FIG. 8., panels B and C. These experiments revealed that the longest of the receptors (2) was by far the most efficient in terms of both magnitude and relative rate of delivery of IgG into cells. After treatment of cells for 1 hour with 10 μM of 2, this receptor (2) enhanced the cellular uptake of anti-DNP IgG by 208-fold in magnitude and 391-fold in rate compared with basal levels of endocytosis. No significant cellular toxicity was observed. Sequential removal of beta-alanine subunits from the linker of 2 to afford receptors 3 and 4 dramatically diminished the effectiveness of these compounds as mediators of ligand uptake. Furthermore, the conversion of the secondary amine of receptor 4 to the secondary amide group of receptor 5 essentially abolished internalization of IgG, reducing delivery by over 50-fold at 10 μM as shown in FIG. 9, panel B.

Example 9

Effect of Linker Structure on Subcellular Localization of Synthetic Receptors

Cells were treated with structurally similar green fluorescent receptors (6-9). Epifluorescence microscopy and fluorescence quenching assays were employed to investigate the differences in cellular fluorescence and subcellular localization. As shown in FIG. 10. Panel A, the overall fluorescence resulting from treatment with 10 μM of these compounds was within 2-fold. However, the subcellular localization of these compounds differed dramatically. Receptor 6 bearing two β-alanine linker subunits was observed predominantly on the cell surface. However, the single β-alanine containing receptor 7 exhibited lower cell surface localization, and the absence of B-alanine in the linker of 8 rendered this compound primarily intracellular. Remarkably, the amide analog 9 was essentially completely associated with internal membranes which explain the inability of this analog to mediate significant cellular uptake of the anti-IgG ligand. This amide analog nearly completely localized with a red fluorescent probe of the cellular golgi apparatus and nuclear membrane, indicating a unique intracellular destination of this receptor.

The fraction of receptors 6-9 at the cell surface was quantified by irreversible quenching of exposed NBD fluorophores on the cell surface. This was accomplished by brief treatment of cells with relatively cell-impermeable reducing agent (sodium hypodisulfite, $NaO_2S-SO_2Na$), which rapidly reduces the nitro functionality of extracellular NBD headgroups to the amine, enabling quantification of differences in cell surface and intracellular fluorescence. Quantitative dithionite quenching assays demonstrated dramatic differences in receptor subcellular localization that paralleled the magnitude and kinetics of IgG uptake observed with receptors 2-5, as shown in FIG. 10, Panel B. Thus, differences in trafficking to intracellular membranes control the efficiency of these synthetic receptors.

Example 10

Temporal Stability of Receptor 2

To evaluate the temporal stability of receptor 2 on the cell surface, the half-life of this compound on Jurkat lymphocytes was quantified by addition of a soluble antibody. Cells were treated with this receptor for 1 hour (10 μM), unincorporated receptor was removed by washing cells with fresh media, and the abundance of 2 as a function of time was detected with a green fluorescent anti-DNP/PrA-AF488 complex. As shown in FIG. 10. Panel C, curve fitting of the flow cytometry data revealed a cell surface half-life of 20 hours. This value is similar to the 24 hour half-life of natural folate receptor that is anchored to the cell surface by covalently attached GPI lipids.

Example 11

Cycling of Receptor 6 Between the Cell Surface and Intracellular Endosomes in Jurkat Lymphocytes To examine whether the green fluorescent receptor 6 might under dynamic cycling, a fluorescent-quenching assay with sodium dithionite was employed. As shown in FIG. 11, Jurkat cells were treated with receptor 6 (10 μM) and cooled to 4° C. to stop plasma membrane recycling. Fluorescence at the cell surface was quenched by treatment with ice-cold sodium dithionite, and cells were washed with cold media to remove this reducing agent (FIG. 11, Panel A). This cell culture was split into two equal portions; one portion was maintained at 4° C., shown in FIG. 11, Panel B, for 30 minutes, and the other portion was allowed to return to 37° C. for 30 minutes to reactivate plasma membrane recycling as shown in FIG. 11, Panel C. Significant return of green fluorescence back to the plasma membrane was observed only in the panel warmed to 37° C. Compare Panels B and C in FIG. 11. NBD headgroups that have returned to the cell's surface were detected with an NBD-binding red fluorescent anti-DNP/PrA-AF633 complex. These results demonstrate that the intracellular fraction of synthetic receptors is in dynamic exchange with the cellular plasma membrane, consistent with synthetic cell surface receptors accessing an active plasma membrane recycling pathway.

Example 12

Quantifying the Rate of Plasma Membrane Recycling of Receptor 10

To quantify the rate of plasma membrane recycling, oregon green-derived receptor 10 was employed. Unlike the more strongly cell-associated DNP and NBD-based receptors, the compound 10 binds proteins in cell culture media and can be rapidly and efficiently depleted from cell surfaces by washing cells with "back exchange" media containing bovine serum albumin (BSA, 1%) and methyl-beta-cyclodextrin (Me-beta-CD, 2 mM). This concentration of Me-beta-CD is known to affect neither endocytosis nor plasma membrane recycling. The oregon green-fluorophore of 10 was also chosen for these studies because unlike structurally similar carboxydfluorescein the fluorescence of oregon green is not appreciably quenched in acidic environment of endosomal compartments. Cells treated with 10 (1 µM) exhibited bright green fluorescence both at the cell surface and in intracellular (endosomal) compartments; patterns of cellular fluorescence were similar to treatment with the structurally related receptor 7 (data not shown). Cells were treated with 10 and cooled to 4° C. to stop dynamic plasma recycling. These cells were washed four times with ice-cold back exchange media to extensively deplete 10 from the cell surface without affecting the population of this compound in intracellular endosomes. Back exchange media pre-warmed to 37° C. was subsequently added to these cells to reactivate plasma membrane recycling. This temperature jump resulted in rapid return of 10 to the plasma membrane by endocytosis, and the added back exchange media rapidly removed the recycled receptors from the cell surface. Quantification of cellular fluorescence as a function of time provided the fluorescence decay curve shown in FIG. 12. Fitting of this data with one-site exponential decay model yielded a recycling half life of 2.8±0.8 minutes, indicating rapid recycling of synthetic cell surface receptors. This recycling rate is similar to the rate of plasma membrane recycling of the fluorescent lipid C6-NBD sphingomyelin.

Example 13

Synthetic Receptor/Ligand Complexes Co-Fractionate with Lipid Raft Components of Cellular Plasma Membranes Another hallmark of many natural cell surface receptors is the proposed association of these biomolecules with cholesterol and sphingolipid-enriched lipid raft subdomains of cellular plasma membranes. These subdomains are generally biochemically characterized as low density fractions of the plasma membrane insoluble in buffers containing non-ionic detergents such as Triton-X at 4° C. Ganglioside GM1 (1) is prototypical example of a small lipid raft-associated cell surface receptor, and complexes of this glycolipid with a fluorescent cholera toxin protein are often used as a marker for lipid rafts. In addition, macromolecules receptors including B-cell receptors, T cell receptors, and growth factor receptors are thought to associate with these membrane subdomains. In certain cases, binding of ligands to receptors initiates formation of lipid rafts. This ligand-mediated concentration of specific membrane lipids has been proposed to recruit intracellular raft-associated kinases to activate cellular signaling pathways.

Figure 13:
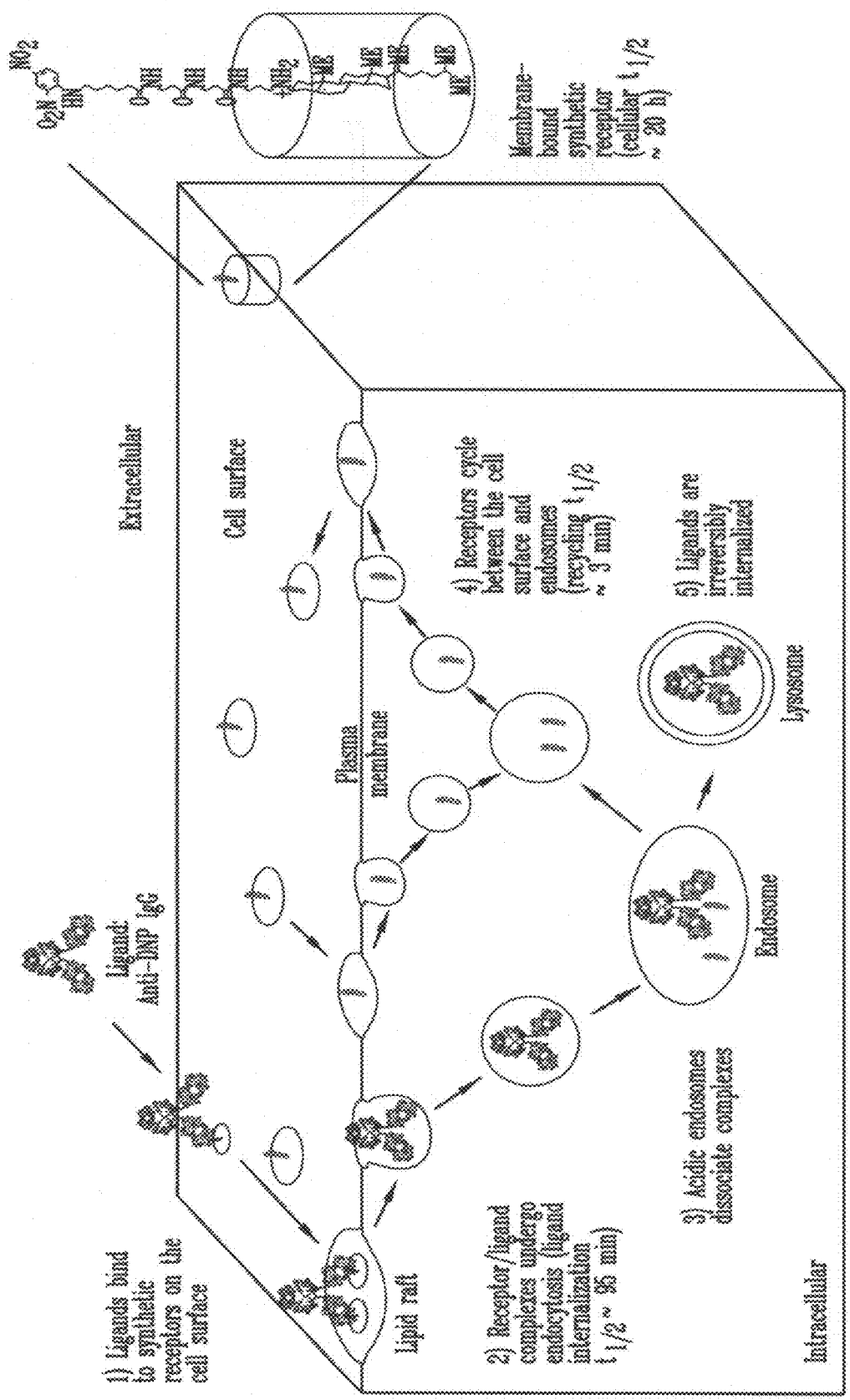
FIG. 13. A simple model of synthetic receptor-mediated endocytosis. Synthetic receptors embedded in cellular plasma membranes rapidly cycle between the cell surface and intracellular endosomes. Binding of the ligand (IgG) results in association with lipid rafts and uptake of the complex by endocytosis. Dissociation in endosomes frees the receptor to return to the cell surface. The protein ligand is sorted to late endosomes and lysosomes.
Figure 14:
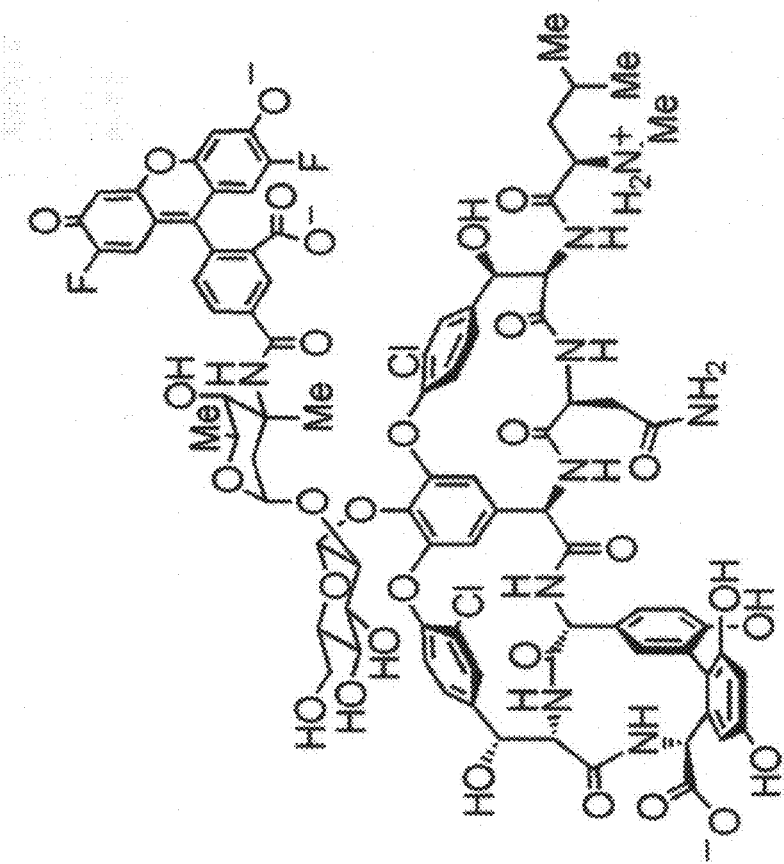
FIG. 14. Structures of the antibiotic vancomycin (1) and a green fluorescent derivative oregon green vancomycin (2).
Figure 14:
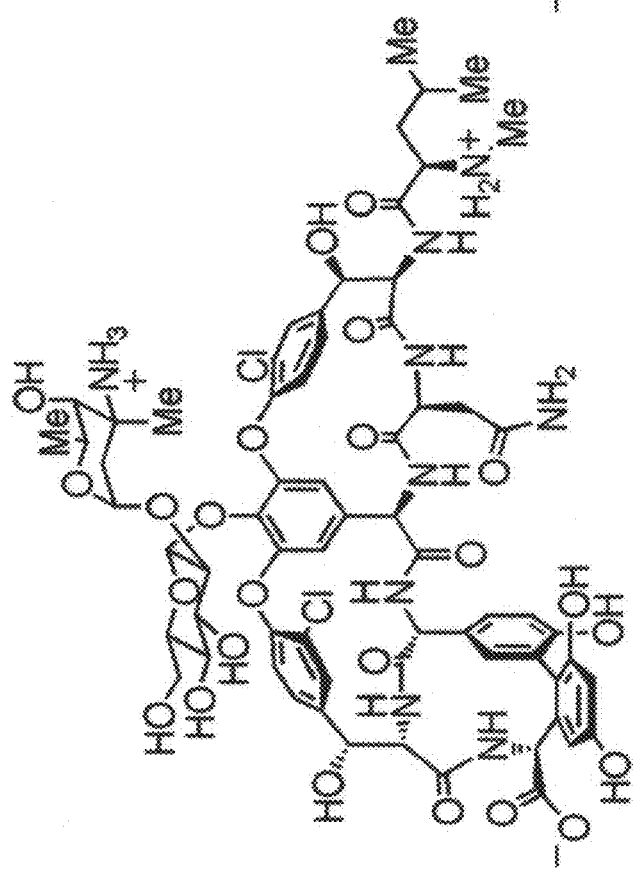
Figure 15:
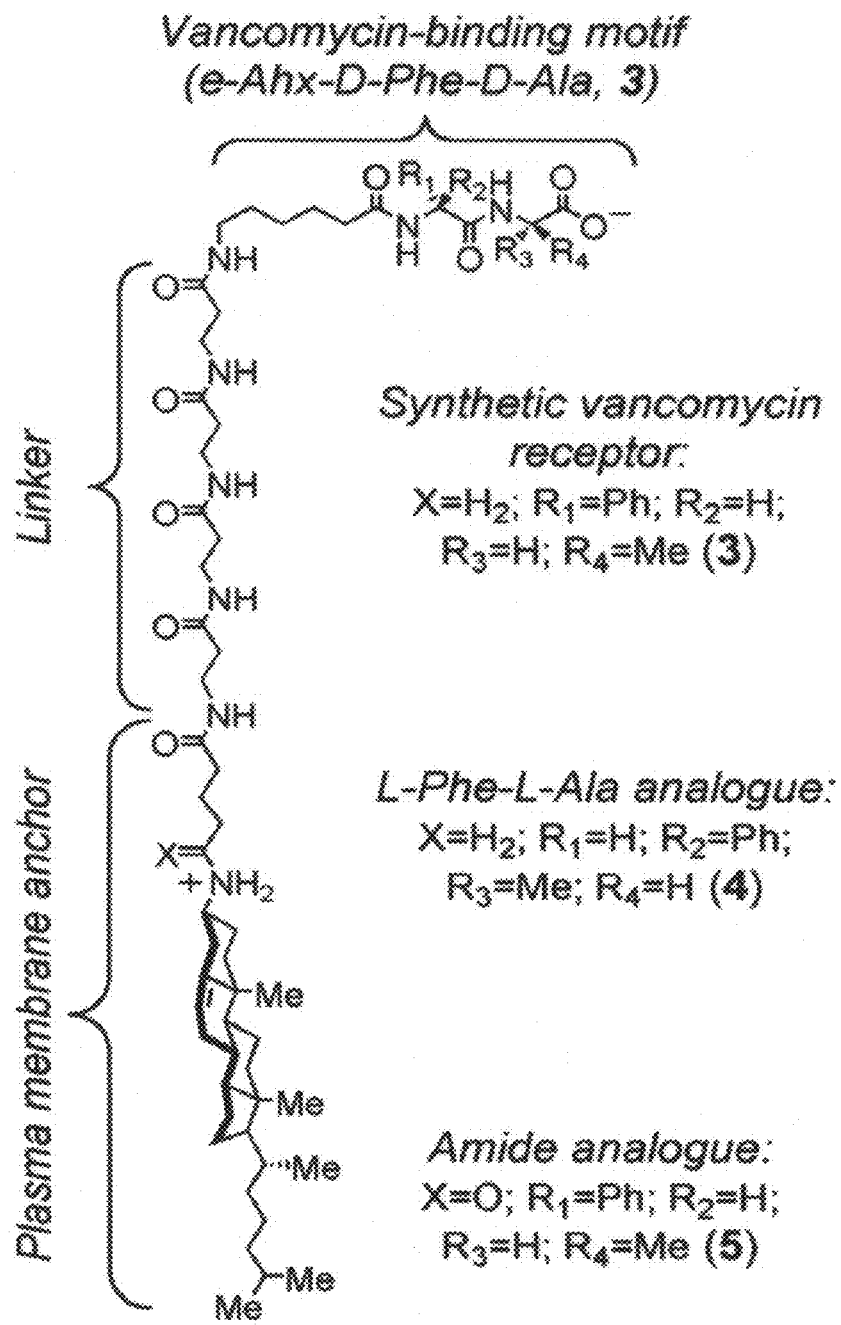
FIG. 15. Structures of a vancomycin-binding synthetic receptor bearing a D-Phe-D-Ala motif (3), a related L-Phe-L-Ala analogue that does not bind vancomycin (4), and an amide analogue that binds vancomycin but exhibits a lower affinity for the cellular plasma membrane (5).

To determine whether synthetic cell surface receptors (2-5) might co-fractionate with ganglioside GM 1 (1) in lipid rafts, sucrose density gradient ultracentrifugation was employed to fractionate cellular membranes containing receptor-ligand complexes (FIG. 13). As positive and negative control experiments, Jurkat cells were treated with green fluorescent cholera toxin B subunit protein and green fluorescent transferrin protein. Unlike binding of cholera toxin to ganglioside GM 1 (1), binding of transferrin to the transferrin receptor on the cell surface does not result in association with lipid rafts. As shown in FIG. 13, a low density fluorescent membrane fraction (#5) was observed upon treatment of the cells with cholera toxin B subunit, but this fraction was not observed until upon treatment with transferrin, consistent with previous studies of lipid raft association of these proteins. Application of this analysis to receptors 2-5 (1 µM) revealed that only receptors 2 and 3 enabled the isolation of this fluorescent low-density membrane fraction (#5). These results paralleled the magnitude of protein uptake mediated by synthetic receptors 2-5 (FIG. 9, Panel B). Unlike the IgG-bound receptors, fractionation of cells treated with green fluorescent receptor 6 alone did not reveal any significant lipid raft association of the free receptor (data not shown). Free receptors may be associated with less well-ordered "lipid shell" domains of cellular membranes. These results suggest additional mechanistic similarities between the IgG-bound synthetic receptors and uptake of cholera toxin mediated by ganglioside GM 1 (FIG. 1).

Example 14

References for Examples 1-13

(1) Sjoback, R.; Nygren, J.; Kubista, M. *Spectrochimica Acta Part a-Molecular and Biomolecular Spectroscopy* 1995, 51, L7-L21.
(2) Dandliker, W. B.; Hsu, M. L.; Levin, J.; Rao, B. R. *Methods Enzymol.* 1981, 74 Pt C, 3-28.
(3) Panvera Corp., M., WI 53711 1998.
(4) Patterson, G. H.; Lippincott-Schwartz, J. *Science* 2002, 297, 1873-1877.
(5) Wu, S.; Lee, S.; Beak, P. *J. Am. Chem. Soc.* 1996, 118, 715-721.
(6) Hussey, S. L.; Peterson, B. R. *J. Am. Chem. Soc.* 2002, 124, 6265-6273.
(7) Hao, M.; Maxfield, F. R. *J. Biol. Chem.* 2000, 275, 15279-15286.
(8) Blank, N.; Gabler, C.; Schiller, M.; Kriegel, M.; Kalden, J. R.; Lorenz, H. M. *J. Immunol. Methods* 2002, 271, 25-35.

Example 15

Figure 16:
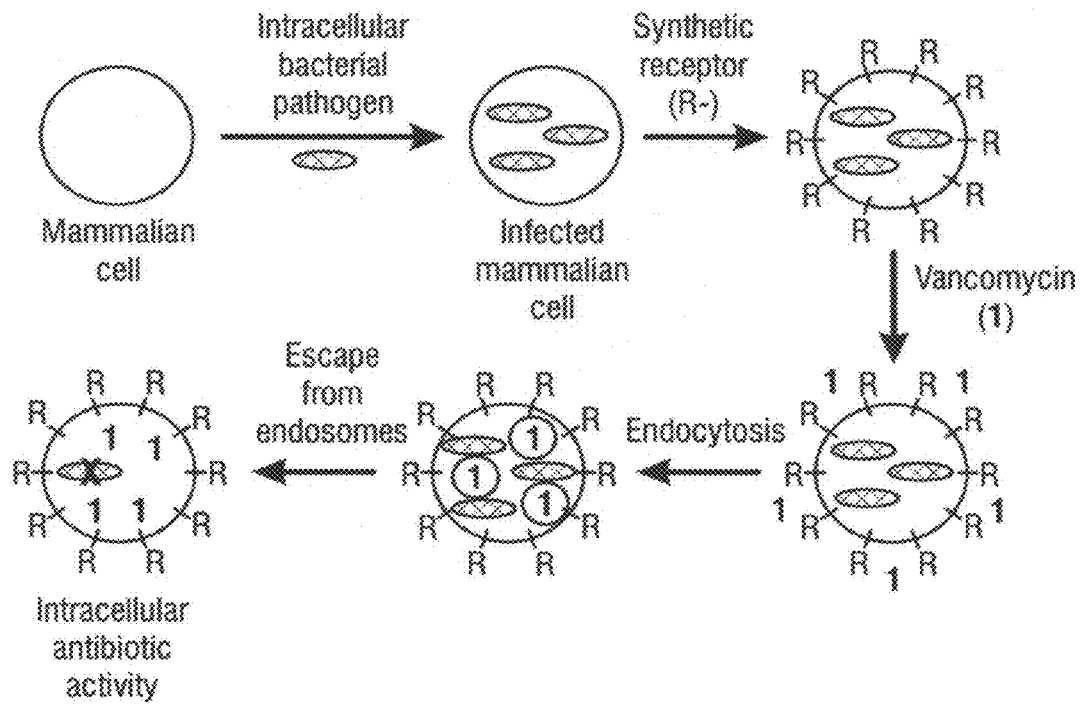
FIG. 16. The synthetic receptor targeting strategy for endocytic delivery of vancomycin (1). The synthetic receptor targeting approach for enhancing the effectiveness of poorly permeable drugs such as vancomycin against intracellular pathogens such as L. monocytogenes and S. auerus.

Design and Synthesis of Receptors for Vancomycin and Related Glycopeptide Antibiotic Ligands The numbered receptors in examples 15-21 refer to those shown in FIGS. 14-19 and in Examples 15-21. We hypothesized that the delivery of vancomycin (1) into endosomes of cells infected with pathogenic bacteria might enable access of this cell-impermeable antibiotic to the cytoplasm. To explore this hypothesis, we synthesized a fluorescent derivative of vancomycin (2) and an artificial cell surface receptor (3) comprising the vancomycin-binding motif D-Phe-D-Ala linked to 3β-cholesterylamine. The D-Phe-D-Ala dipeptide was chosen because of its improved affinity for vancomycin ($K_d$~7 µM) compared with the natural D-Ala-D-Ala substrate.[6] This binding group was coupled to 3β-cholesterylamine to add a membrane anchor previously shown by our laboratory to access a membrane trafficking pathway involving rapid cycling between the plasma membrane and endosomes of mammalian cells.[7] Control compounds that do not bind vancomycin (L-Ala-L-Ala analogue 4) or that exhibit lower affinity for the cellular plasma membrane (amide analogue 5) were also synthesized for comparison. Addition of synthetic receptor 3 to healthy (non-infected) mammalian cells was envisioned to accomplish the following: (a) the vancomycin-binding motif would be projected from the cell surface; (b) interactions of the receptor (3) with vancomycin (1) would shuttle this drug into endosomes; (c) the antibiotic would dissociate from the receptor in endosomes allowing the free receptor to cycle back to the cell surface for additional rounds of delivery; and (d) vancomycin would become trapped in endosomes/lysosomes and degraded. In contrast, in cells infected with a microbial pathogen, we hypothesized that step (d) would be altered by the secretion of membrane disruptive proteins by the pathogen. These proteins were predicted to disrupt vancomycin-loaded endosomes and release the antibiotic into the cytoplasm harboring the bacterial parasite. This strategy, termed synthetic receptor targeting,[7] is illustrated in FIG. 16.

Example 16

Figure 17:
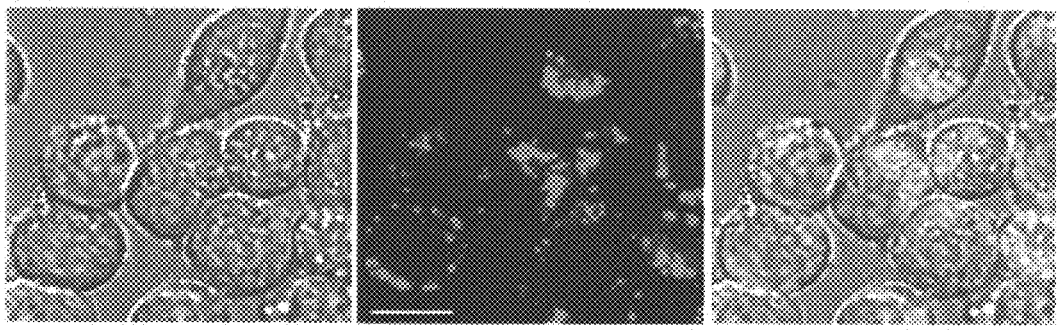
FIG. 17. Confocal laser scanning and differential interference contrast (DIC) microscopy of living J-774 macrophages alone (Panel A) and infected with L. monocytogenes (Panel B). Prior to microscopy, receptor 2 (10 μM) was added to cells for 1 h, cells were washed to remove excess receptor, and fluorescent vancomycin (3, 3 μM) was added for 4 h. Scale bar: 10 μm.
Figure 17:
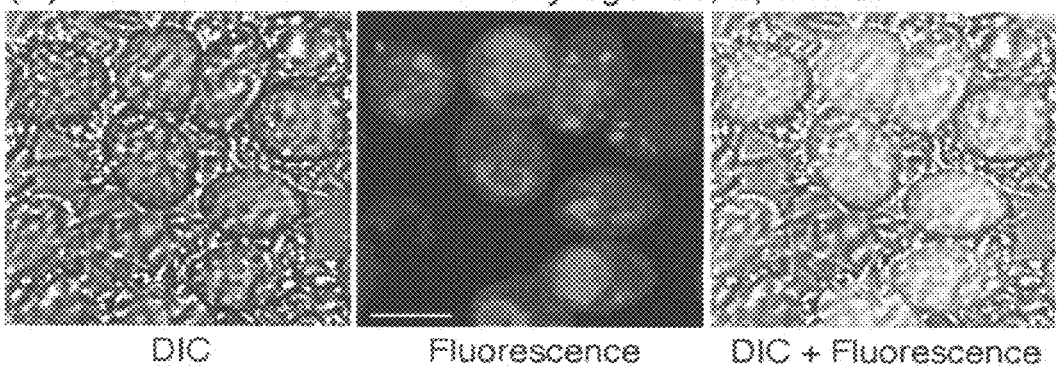

Confocal Laser Scanning and Differential Interference Contrast (DIC) Microscopy of Living J-774 Murine Macrophages Confocal laser scanning microscopy was used to examine the delivery of fluorescent vancomycin derivative 2 into J774 mouse macrophage cells. As shown in FIG. 17, cells treated with both receptor 3 and ligand 2 exhibited substantial uptake of this fluorescent probe. In healthy (non-infected) cells, this intracellular fluorescence was localized to endosomes and lysosomes as evidenced by colocalization with a red fluorescent marker of these compartments (supporting information). However, when these cells were also infected by *L. monocytogenes*, the fluorescent vancomycin (2) was distributed throughout the cytoplasm and nucleus.

Example 17

Figure 18A:
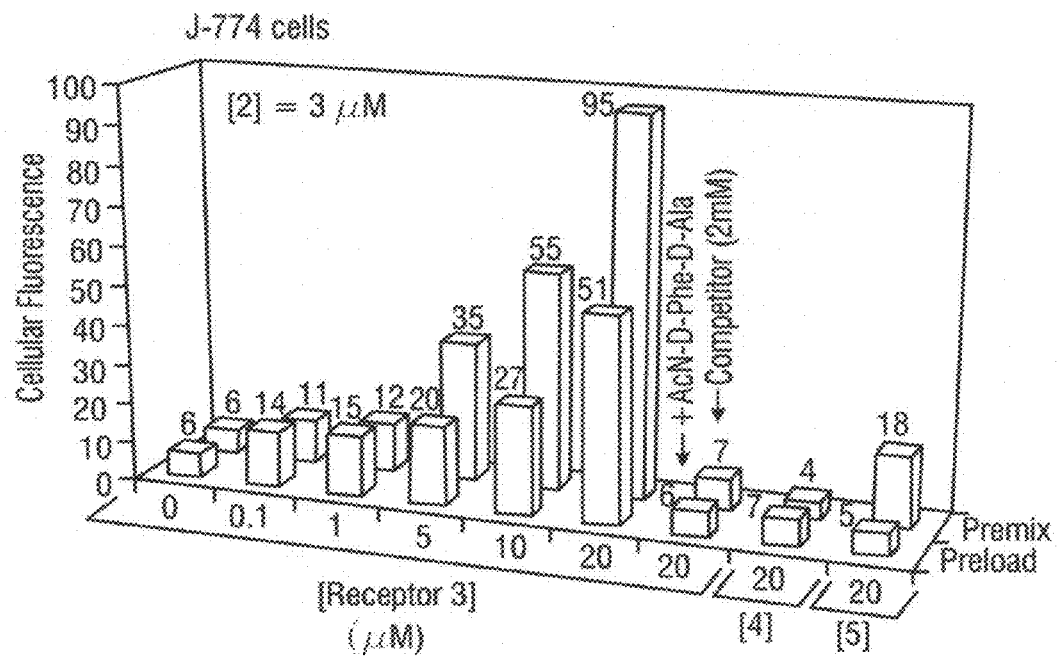
FIG. 18. Flow cytometric analysis of cellular uptake of fluorescent vancomycin 2 promoted by synthetic receptor 3 and control compounds. Preload conditions: Receptor 3 or analogues (4, 5) were added to cells for 1 h to load the plasma membrane, cells were washed, and 2 (3 μM) was added for 4 h. Premix conditions: Receptor 3 or analogues (4, 5) were preequilibrated with 2 (3 μM) at 23° C. for 1 h followed by addition of this mixture to cells for 4 h.
Figure 18B:
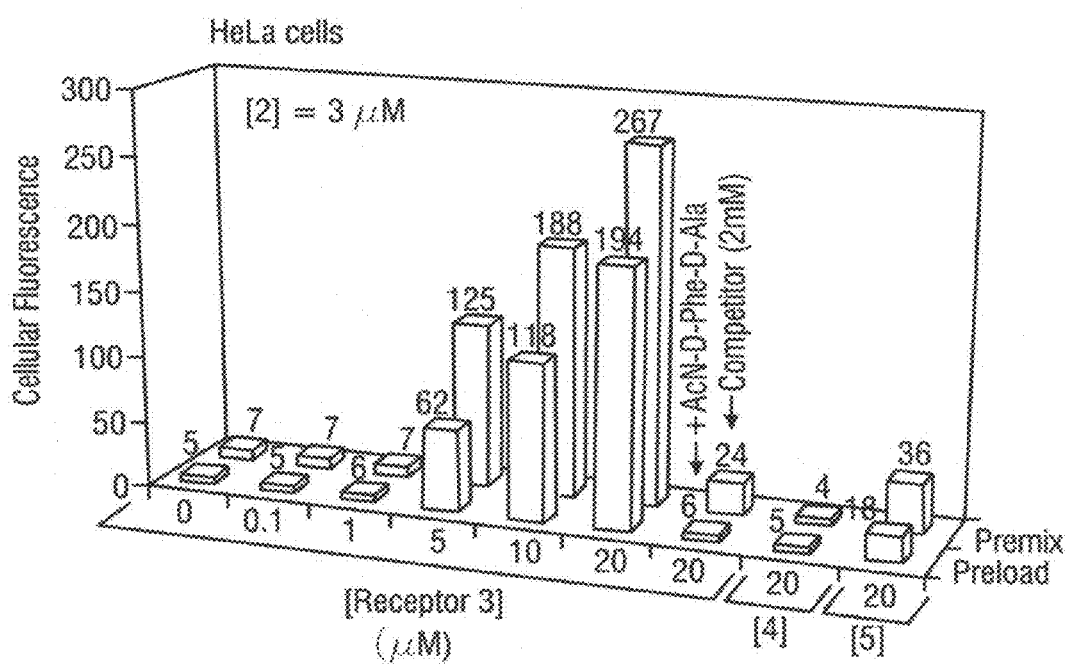

Dose-Dependent Effectiveness of Delivery of Receptor 2 into Mouse J-774 Cells and Human HeLa Cells The dose-dependent effectiveness of delivery of 2 into mouse J-774 cells and human HeLa cells mediated by receptor 2 was examined quantitatively by flow cytometry. As shown in FIG. 18, preequilibration of the receptor (3) with the ligand (2) prior to addition to cells was ca. 2-fold more effective for delivery compared with preloading of cellular plasma membranes with the receptor (3) followed by addition of the ligand (2). However both of these conditions engendered substantial receptor-mediated enhancements of ligand uptake. These effects were blocked by addition of AcNH-D-Phe-D-Ala-$CO_2$H as a soluble competitor, and the L-Phe-L-Ala-analogue 4 was ineffective, demonstrating specificity of recognition. Additionally, consistent with previous studies of derivatives of 3b-cholesterylamine,[7] the amide analogue 5 was much less active.

Example 18

Figure 19A:
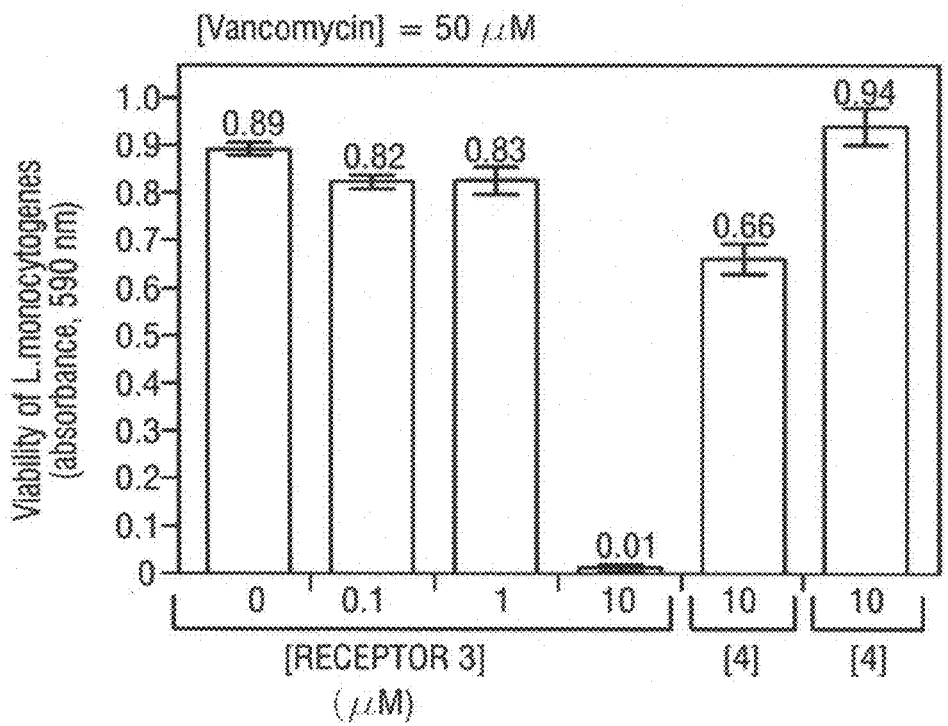
FIG. 19. Effects of premixed receptor 3 and vancomycin (1) on HeLa cells infected with L. monocytogenes. Infected cells were treated with 1 and 3 for 6 h at the concentrations indicated, then washed with media lacking antibiotics. Panel A: Viability of L. monocytogenes cultured from infected HeLa cells. BHI media was added, and bacterial growth was quantified by absorbance measurements after an additional 18 h. Panel B: DMEM media was added and viability of infected HeLa cells after an additional 30 h in culture quantified by flow cytometry.
Figure 19B:
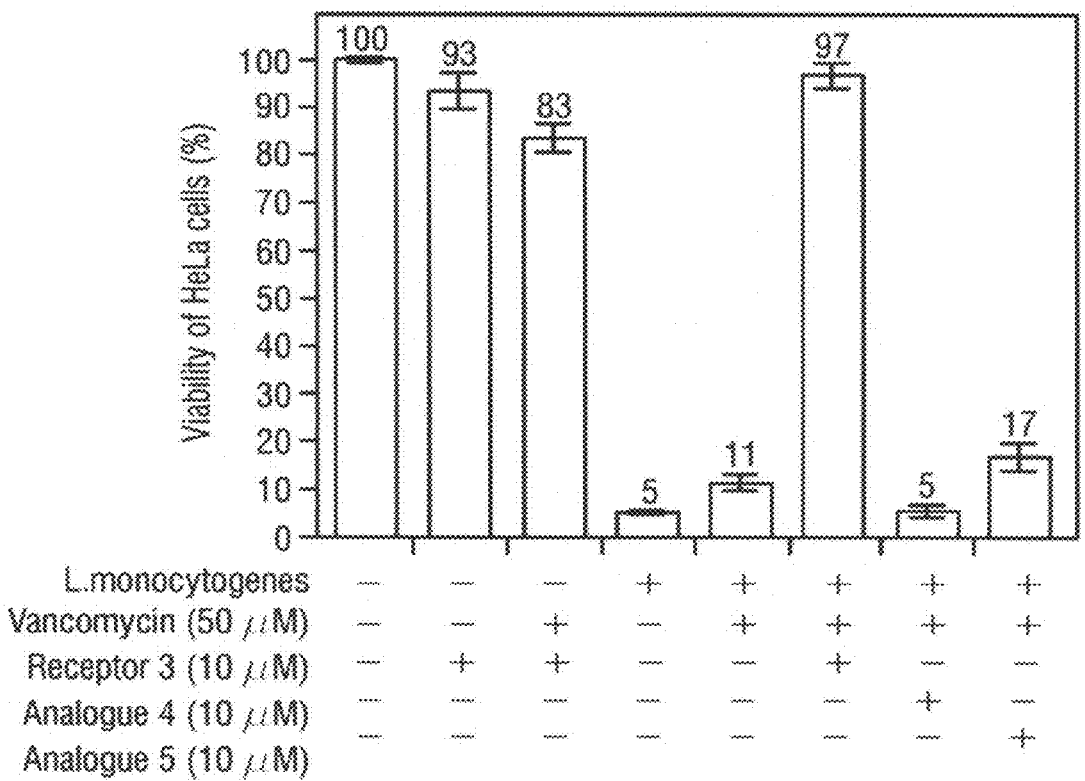

Delivery of Vancomycin Via Synthetic Receptor 3 into HeLa Cells Infected by *L. monocytogenes* to Determine Effects on Antibiotic Activity against this Pathogen The synthetic receptor 3 was employed to deliver vancomycin (1) into HeLa cells infected by *L. monocytogenes* to investigate effects on antibiotic activity against this pathogen. As shown in FIG. 19, treatment of HeLa cells with this receptor (10 µM) enabled vancomycin (50 µM) to eliminate this intracellular parasite and rescue HeLa cells from the lethal effects of this pathogen.

Example 19

Figure 20:
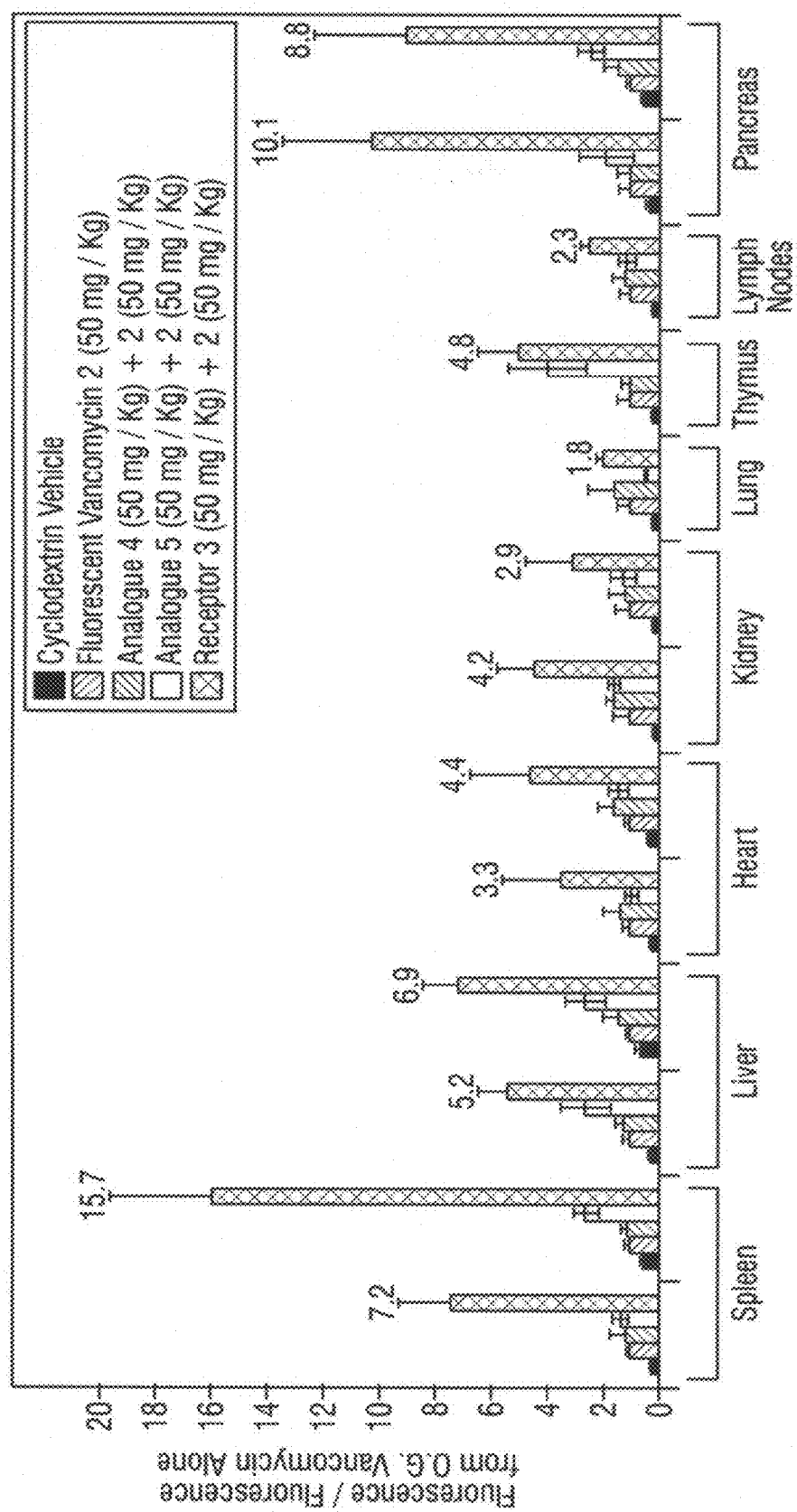
FIG. 20. Synthetic receptor targeting of fluorescent vancomycin 2 to specific tissues in vivo. Mice were injected i.p. with compounds, tissues were isolated after 8 h, and cellular fluorescence was analyzed by flow cytometry. In the spleen, liver, heart, kidney, and pancreas, two different populations of cells were analyzed.

Delivery of Fluorescent Vancomycin Derivative 2 by Synthetic Receptor 3 In Vivo to Mice The delivery of fluorescent Vancomycin derivative 2 by synthetic receptor 3 was investigated in vivo (FIG. 20). These and related compounds were injected into mice and the fluorescence of cells isolated from specific tissues was examined by flow cytometry. As shown in FIG. 20, synthetic receptor-mediated targeting of the fluorescent vancomycin (2) to specific tissues was observed, indicating that N-alkyl-3b-cholesterylamine derivatives such as 3 provide novel tools for drug delivery in vivo. These results demonstrate that a synthetic cell surface receptor can enhance the in vitro effectiveness of a clinically used drug against an intracellular pathogen. This receptor also enables targeting of the drug to specific tissues in vivo. This approach provides a novel tool to combat microorganisms that invade mammalian cells.

Example 20

General Information for Histidine/Metal Chelators

Chemical reagents were obtained from Acros, Aldrich, Alfa Aesar, or TCI America. Solvents were from EM Science. Media and antibiotics were purchased from Mediatech. DiI-loaded human low-density lipoprotein was from Invitrogen. Commercial grade reagents were used without further purification unless otherwise noted. Anhydrous solvents were obtained after passage through a drying column of a solvent purification system from GlassContour (Laguna Beach, Calif.). All reactions were performed under an atmosphere of dry argon or nitrogen. Reactions were monitored by analytical thin-layer chromatography on plates coated with 0.25 mm silica gel 60 $F_{254}$ (EM Science). TLC plates were visualized by UV irradiation (254 nm) or stained with a solution of phosphomolybdic acid and sulfuric acid in ethanol (1:1:20). Flash column chromatography employed ICN SiliTech Silica Gel (32-63 µm). Purification by preparative reverse phase HPLC employed an Agilent 1100 preparative pump/gradient extension instrument equipped with a Hamilton PRP-1 (polystyrene-divinylbenzene) reverse phase column (7 µm particle size, 21.5 mm×25 cm). The HPLC flow rate was increased from 10 mL/min (t=0 min) to 20 mL/min (t=2 min) and maintained at 20 mL/min for the remainder of the run unless otherwise noted. Melting points were measured with a Thomas Hoover capillary melting point apparatus and are uncorrected. Infrared spectra were obtained with a Perkin Elmer 1600 Series FTIR. NMR spectra were obtained with Bruker CDPX-300, DPX-300, AMX-360, or DRX-400 instruments with chemical shifts reported in parts per million (ppm, δ) referenced to either CDCl$_3$ ($^1$H 7.27 ppm; $^{13}$C 77.23 ppm), DMSO-d$_6$ ($^1$H 2.50 ppm; $^{13}$C 39.51 ppm), or (CH$_3$)$_4$Si. High-resolution mass spectra were obtained from the University of Texas at Austin and Penn State University Mass Spectrometry Facilities (ESI and CI). Peaks are reported as m/z.

Example 21

Synthetic Procedures and Compound Characterization Data

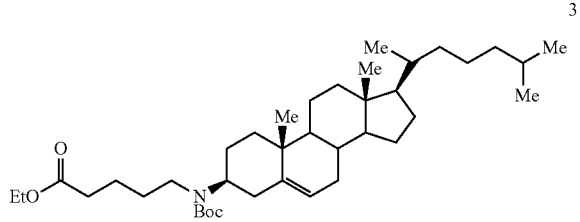

Ethyl 5-{(tert-butoxycarbonyl)[(3β)-cholest-5-en-3-yl]amino}pentanoate (3). To DMF (10 mL) was added 3β-amino-5-cholestene (2, 386 mg, 1.0 mmol),[1] ethyl 5-bromovalerate (174 µL, 1.1 mmol) and K$_2$CO$_3$ (276 mg, 2.0 mmol). The solution was heated to 60° C. and stirred for 24 h. The reaction was cooled to 23° C. and DMF was removed in vacuo. To the resulting solid residue was added CH$_2$Cl$_2$ (10 mL), insoluble salts were removed by filtration, and solids were washed with additional CH$_2$Cl$_2$ (5 mL). To this solution containing the crude secondary amine product was added (Boc)$_2$O (327 mg, 1.5 mmol) and DIEA (0.5 mL, 3.0 mmol). The reaction was stirred for 3 h at 23° C. and concentrated in vacuo. Flash column chromatography (hexanes/ethyl acetate, 10:1) afforded 3 (417 mg, 68%) as a white solid, mp 78-79° C.; $^1$H NMR (400 MHz, CDCl$_3$) δ 5.30 (d, 1H), 4.10 (q, J=7.1 Hz, 2H), 3.73 (br s, 1H), 3.09 (br s, 2H), 2.30 (t, J=7.1 Hz, 2H), 2.01-0.83 (m, 56H), 0.66 (s, 3H); $^{13}$C NMR (100 MHz, CDCl$_3$) δ 173.6, 155.5, 141.3, 121.4, 79.3, 60.4, 56.9, 56.3 (×2), 50.3, 42.6 (×2), 39.9, 39.7, 38.6, 37.1, 36.8, 36.3, 35.9, 34.2, 32.0 (×2), 28.7 (Boc Me$_3$), 28.4, 28.1 (×2), 26.9, 24.4, 24.0, 23.0, 22.7, 22.6, 21.2, 19.6, 18.9, 14.4, 12.0; IR (film) ν max 2935, 2867, 1737, 1692, 1466, 1409, 1365, 1247, 1173 cm$^{-1}$; CI m/z 614.5146 (MH$^+$, C$_{39}$H$_{68}$NO$_4$ requires 614.5148).

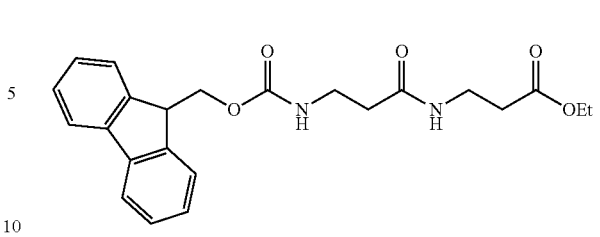

N-Fmoc-β-alanine-β-alanine ethyl ester (5). N-Fmoc-β-alanine (311 mg, 1.0 mmol) in anhydrous CH$_2$Cl$_2$ (20 mL) under N$_2$ was cooled to 0° C. HOBt (168 mg, 1.1 mmol) and EDC (230 mg, 1.2 mmol) were added and the solution was stirred for 30 min at 0° C. β-Alanine ethyl ester hydrochloride (169 mg, 1.1 mmol) in anhydrous CH$_2$Cl$_2$ (10 mL) and DMA (180 µL, 1.1 mmol) were added. The reaction was warmed to 23° C. and stirred for 16 h. The reaction solution was diluted with CH$_2$Cl$_2$ (30 mL) and washed with aqueous HCl (5%, 30 mL), followed by aqueous NaOH (0.1 M, 30 mL), and deionized H$_2$O (30 mL). The organic layer was dried over anhydrous Na$_2$SO$_4$ and concentrated in vacuo. Flash column chromatography (hexanes/ethyl acetate, 1:2) afforded 5 (394 mg, 96%) as a white solid, mp 158.5-159° C.; $^1$H NMR (300 MHz, CDCl$_3$) δ 7.74 (d, J=7.5 Hz, 2H), 7.58 (d, J=7.5 Hz, 2H), 7.38 (m, J=7.5 Hz, 2H), 7.29 (m, J=7.5 Hz, 2H), 6.53 (br m, 1H), 5.77 (br m, 1H), 4.34 (d, J=7.1 Hz, 2H), 4.18 (t, J=7.1 Hz, 1H), 4.11 (q, J=7.1 Hz, 2H), 3.50 (m, 4H), 2.52 (t, J=6.0 Hz, 2H), 2.40 (t, J=5.7 Hz, 2H), 1.23 (t, J=7.1 Hz, 3H); $^{13}$C NMR (75 MHz, CDCl$_3$) δ 172.6, 171.6, 156.7, 144.0, 141.3, 127.8, 127.1, 125.2, 120.1, 66.8, 60.9, 47.3, 37.2, 36.0, 35.0, 34.1, 14.3; IR (film) ν max 3319, 3069, 2978, 2955, 2884, 1732, 1689, 1634, 1538, 1446, 1270, 1190 cm$^{-1}$; CI 411.1922 m/z (MH$^+$, C$_{23}$H$_{27}$N$_2$O$_5$ requires 411.1920).

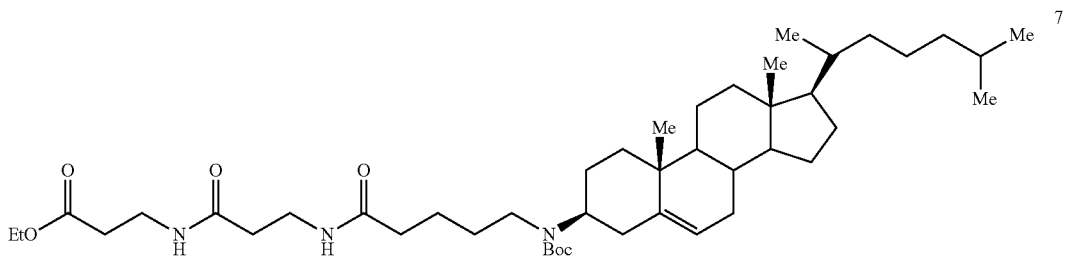

Ethyl 5-[(3β)-cholest-5-en-3-yl]-2,2-dimethyl-4,10,14-trioxo-3-oxa-5,11,15-triazaoctadecan-18-oate (7)

Aqueous LiOH (10 mL, 0.5 M) was added dropwise to a solution of 3 (315 mg, 0.51 mmol) in a mixture of MeOH (15 mL) and THF (10 mL). The solution was stirred for 4 h at 23° C. and the organic solvents were removed in vacuo. The remaining aqueous solution was acidified with aqueous HCl (10%) and the resulting carboxylic acid precipitated as a white solid. This solid was collected by vacuum filtration, washed with cold water, and dried in vacuo. The dried solid was dissolved in anhydrous CH$_2$Cl$_2$ (20 ml) under dry N$_2$ and cooled to 0° C. HOBt (92 mg, 0.6 mmol) and EDC (125 mg, 0.65 mmol) were added and the solution was stirred at 0° C. for 30 min. To this solution was added β-alanine-β-alanine ethyl ester (6, 141 mg, 0.75 mmol, prepared by treatment of 5 (310 mg) in DMF (8 mL) with piperidine (2 mL) for 10 min, followed by removal of solvent under high vacuum) in anhydrous CH$_2$Cl$_2$ (15 mL) over 15 min. The reaction was allowed to warmed to 23° C. and stirred for an additional 16 h. The solution was diluted with $CH_2Cl_2$ (50 mL) and washed with aqueous NaOH (0.1 M, 40 mL) followed by deionized $H_2O$ (40 mL). The organic layer was dried over anhydrous $Na_2SO_4$ and concentrated in vacuo. Flash column chromatography ($CH_2Cl_2$/MeOH, 30:1) afforded 7 (330 mg, 86%) as colorless oil; $^1H$ NMR (300 MHz, $CDCl_3$) δ 6.62 (br m, 2H), 5.29 (d, J=4.9 Hz 1H), 4.11 (q, J=7.1 Hz, 2H), 3.48 (m, 4H), 3.33 (br, 1H), 3.07 (br s, 2H), 2.49 (t, J=6.0 Hz, 2H), 2.35 (t, J=5.4 Hz, 2H), 2.16 (br, 2H), 1.99-0.75 (m, 56H), 0.64 (s, 3H); $^{13}C$ NMR (75 MHz, $CDCl_3$) δ 173.1, 172.6, 171.8, 155.6, 141.5, 121.4, 79.4, 60.9, 56.8, 56.3 (×2), 50.2, 42.4 (×2), 39.9, 39.6 (×2), 38.5 (×2), 37.2, 36.8, 36.3, 35.9, 35.6, 35.2, 34.2, 32.0 (×2), 28.7 (Boc $Me_3$), 28.4, 28.1 (×2), 26.9, 24.4, 23.9, 23.2, 22.9, 22.7, 21.2, 19.6, 18.8, 14.3, 12.0; IR (film) ν max 3293, 3082, 2868, 1737, 1693, 1644, 1549, 1466, 1412, 1366, 1251, 1175, 1156 $cm^{-1}$; CI m/z 756.5891 ($MH^+$, $C_{45}H_{78}N_3O_6$ requires 756.5891).

thyl]-N-ε-benzyloxycarbonyl-L-lysine tert-butyl ester (the Cbz precursor) as previously reported,[2] but the Cbz precursor (3.4 g) in EtOH (50 mL) was deprotected by catalytic hydrogenation (Pd(C), 10%) using 300 psi $H_2$ for 12 h to afford 2.51 g of amine (97%). The reaction was warmed to 23° C. and stirred for 16 h. The solution was diluted with $CH_2Cl_2$ (20 mL) and washed with aqueous NaOH (0.1 M, 15 mL) followed by deionized $H_2O$ (15 mL). The organic layer was dried over anhydrous $Na_2SO_4$ and concentrated in vacuo. Flash column chromatography ($CH_2Cl_2$/MeOH, 30:1) afforded 8 (102 mg, 85%) as colorless oil; $^1H$ NMR (400 MHz, $CDCl_3$) δ 6.86 (br s, 1H), 6.65 (br m, 2H), 5.31 (d, J=4.9 Hz 1H), 3.50 (m, 4H), 3.42 (s, 2H), 3.43 (s, 2H), 3.32 (m, 2H), 3.28-3.16 (m, 2H), 3.08 (br s, 2H), 2.42 (m, 2H), 2.35 (t, J=5.9 Hz, 2H), 2.17 (br, 2H), 2.01-0.84 (m, 86H), 0.66 (s, 3H); $^{13}C$ NMR (100 MHz, $CDCl_3$) δ 172.4, 172.2, 171.9, 170.7 (×3),

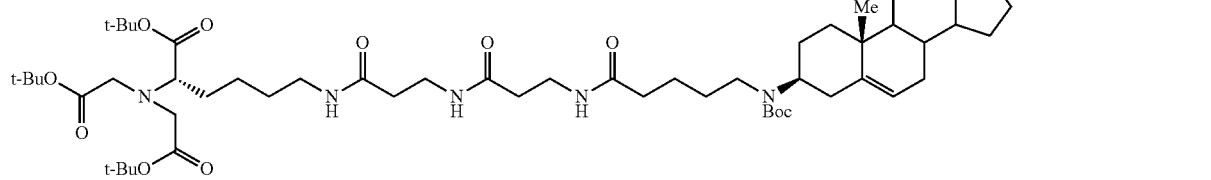

Di-tert-butyl 2-(2-tert-butoxy-2-oxoethyl)-22-[(3β)-cholest-5-en-3-yl]-25,25-dimethyl-9,13,17,23-tetraoxo-24-oxa-2,8,12,16,22-pentaazahexacosane-1,3-dicarboxylate (8). To a solution of 7 (83 mg, 0.11 mmol) in a mixture of MeOH (6 mL) and THF (4 mL) was slowly added aqueous LiOH (2 mL, 0.5 M). The solution was stirred for 4 h at 23° C. Solvents were removed in vacuo, the solid residue was resuspended in aqueous HCl (10%, 10 mL), and the resulting carboxylic acid was extracted with ethyl acetate (2×20 mL). The organic layer was dried over anhydrous $Na_2SO_4$ and solvents were removed in vacuo. The solid residue was dissolved in of anhydrous $CH_2Cl_2$ (10 mL) under dry $N_2$ and cooled to 0° C. HOBt (22 mg, 0.14 mmol) and EDC (29 mg, 0.15 mmol) were added, the solution was stirred for 30 min at 0° C., and $N^α,N^α$-bis[(tert-butoxycarbonyl)methyl]-L-lysine tert-butyl ester (75 mg, 0.17 mmol) was added. This amine was prepared from $N^α,N^α$-Bis[(tert-butoxycarbonyl)me- 155.7, 141.8, 121.4, 81.7, 81.3 (×2), 79.4, 64.9, 56.9, 56.3 (×2), 54.2 (×2), 50.3, 42.5 (×2), 39.9, 39.7 (×2), 39.2, 38.6 (×2), 37.3, 36.8, 36.3, 36.0, 35.9, 35.6, 35.1, 32.0 (×2), 29.4, 28.7 (Boc $Me_3$), 28.5, 28.4 (t-Bu $Me_3$), 28.3 (t-Bu $Me_3$×2), 28.2 (×2), 27.8, 26.9, 24.4, 24.0, 23.4, 23.0, 22.7, 22.6, 21.2, 19.7, 18.9, 12.0; IR (film) ν max 3288, 3082, 2934, 2868, 1744, 1687, 1642, 1550, 1458, 1367, 1250, 1222, 1148 $cm^{-1}$; CI m/z 1140.8524 ($MH^+$, $C_{65}H_{114}N_5O_{11}$ requires 1140.8515).

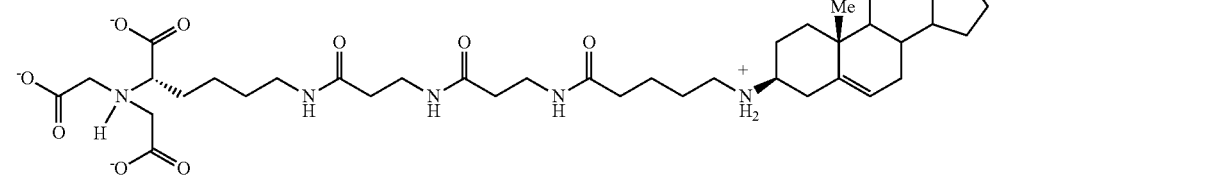

4-Carboxy-3-(carboxymethyl)-22-[(3β)-cholest-5-en-3-ylamino]-10,14,18-trioxo-3,9,13,17-tetraazadocosan-1-oic acid (1). TFA (1.5 mL) was added dropwise to a solution of 5 (22 mg, 0.019 mmol) in $CH_2Cl_2$ (5 mL). The solution was stirred for 16 h and the solvent was removed in vacuo. Purification by preparative reverse-phase HPLC (gradient: 49.9% MeCN, 50% H$_2$O, and 0.1% TFA to 99.9% MeCN, 0% H$_2$O, and 0.1% TFA over 30 min; retention time=16.3 min (215 nm)) afforded 1 (15.6 mg, 94%) as a white solid, mp 101-103° C.; $^1$H NMR (300 MHz, CDCl$_3$) δ 5.34 (br s, 1H), 3.48 (m, 4H), 3.35 (br m, 5H), 3.10 (br s, 2H), 2.85 (br s, 3H), 2.31 (br m, 7H), 2.16 (br m, 2H), 1.94-0.75 (m, 50H), 0.65 (s, 3H); $^{13}$C NMR (75 MHz, CDCl$_3$) δ 174.7 (×3), 172.2, 172.0 (×2), 137.6, 123.8, 57.9, 56.4, 55.9, 55.0, 54.9 (×2), 49.7, 44.1, 42.0, 40.0 (×2), 39.4, 39.3 (×2), 38.6, 36.8, 36.5, 36.0, 35.8, 35.6, 35.4, 34.9, 34.7, 31.6, 31.5, 29.2, 28.2, 28.0, 27.8 (×2), 24.9, 24.0, 23.6, 23.1, 22.5, 22.3, 20.7, 18.8, 18.4, 11.6; IR (film) ν max 3700-2500 (br), 3295, 3084, 2938, 2868, 1732, 1686, 1634, 1556, 1468, 1441, 1382, 1202, 1143 cm$^{-1}$; ESI+ m/z 872.6093 (MH$^+$, C$_{48}$H$_{82}$N$_5$O$_9$ requires 872.6107).

Example 22

Biological Assays and Protocols

The numbered receptors in examples 22-24 refer to those shown in FIGS. 20-25 and in Examples 22-24.

General. Standard protocols were employed for microbiological techniques and plasmid construction. Oligonucleotide synthesis and sequencing of all new plasmid constructs was by the Pennsylvania State University Huck Institute Nucleic Acid Facility. Genes were constructed using the Polymerase Chain Reaction (PCR) with either Pfu polymerase (Stratagene) or Platinum Taq polymerase (Gene Choice). *E. coli* strain DH5-α (Clontech/BD biosciences) was used for subcloning, and proteins were expressed in *E. coli* strain BL21 (DE3)pLysS (Novagen).

Cell culture. Jurkat lymphocytes (human acute T-cell leukemia, ATCC #TIB-152) were maintained in Roswell Park Memorial Institute (RPMI) 1640 media supplemented with Fetal Bovine Serum (FBS, 10%), penicillin (100 units/mL), and streptomycin (100 μg/mL). RPMI media used for cell culture and wash steps contained antibiotics and FBS unless otherwise noted.

Microscopy. A Zeiss LSM 5 Pascal confocal laser-scanning microscope fitted with a Plan Apochromat objective (63×) was employed. Alexa Fluor 488 was excited with a 488 nm Argon ion laser and emitted photons were collected through 505 nm LP filter. Excitation of DiI-loaded LDL employed a 543 nm HeNe laser and a 560 nm LP filter.

Flow cytometry. Analyses were performed with a Beckman-Coulter XL-MCL bench-top flow cytometer. Forward-scatter (FS) and side-scatter (SSC) dot plots afforded cellular physical properties of size and granularity that allowed gating of live cells. After gating, 10,000 cells were counted. For studies of uptake of AcGFP His tag fusion proteins, AcGFP was excited at 488 nm with a 15 mW air-cooled argon-ion laser, the emission was split with a 550 nm dichroic and filtered through a 510 nm long pass filter and 530/30-nm band pass filter. The PMT voltage for this instrument was set to 724 for detection of AcGFP. Calibration with Sphero Rainbow Calibration particles (Spherotech) bearing 330,000 molecules of fluorescein/particle provided a fluorescence of 16.7 at this voltage.

Figure 25:
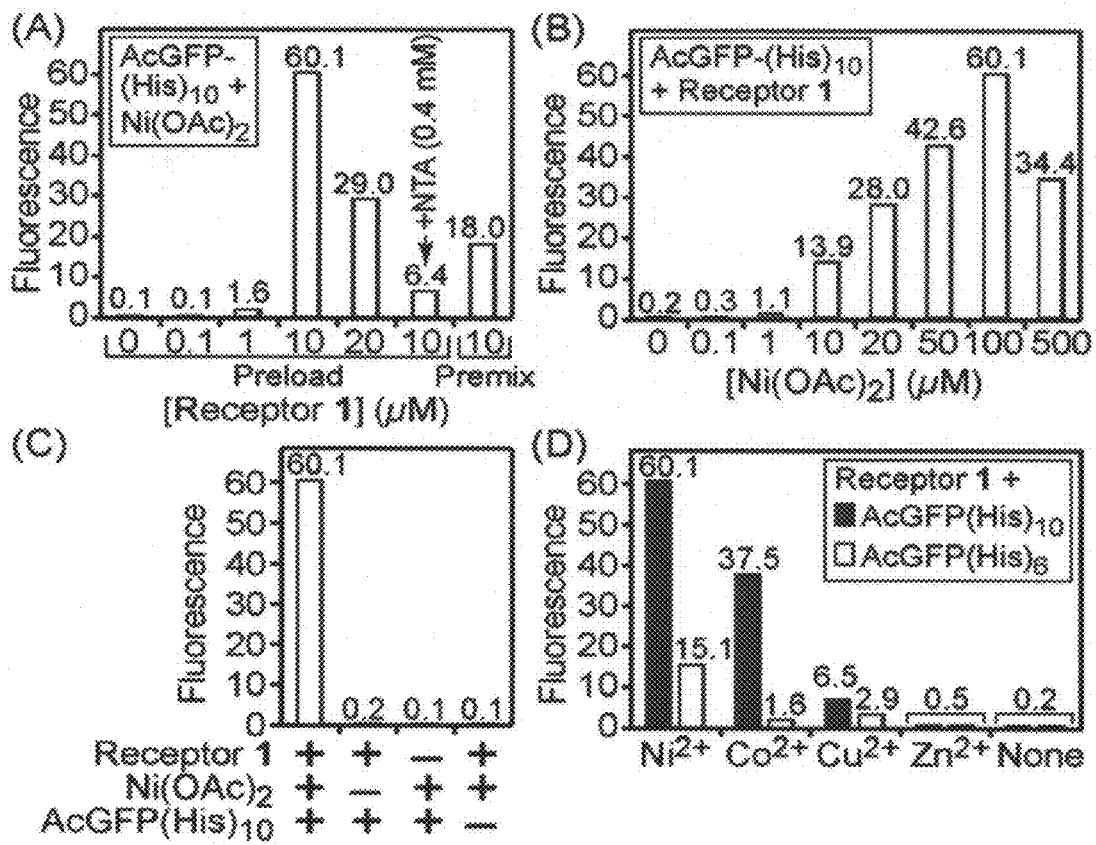
FIG. 25. Analysis of cellular uptake of His-tagged AcGFP proteins by flow cytometry. Each bar represents the average fluorescence of 10,000 cells. Unless otherwise noted, cellular plasma membranes of Jurkat lymphocytes were preloaded with receptor 1 (10 μM) for 1 h at 37° C., cells were washed with fresh media, and His-tagged AcGFP (3.2 μM)/metal diacetate solution (100 μM) was added for 4 h at 37° C. Prior to analysis, cells were washed with NTA (400 μM, 30 min) in PBS (pH 7.4) to remove bound surface protein. Panel A: Dose dependence of receptor-mediated uptake. Premix conditions: a solution containing receptor 1, Ni(OAc)$_2$, and AcGFP (His)$_{10}$ was added to cells for 4 h. Panel B: Dependence on [Ni(OAc)$_2$]. Panel C: Omission control experiments. Panel D; Uptake of (His)$_6$ and (His)$_{10}$ fusion proteins promoted by different metal diacetates.
Figure 26:
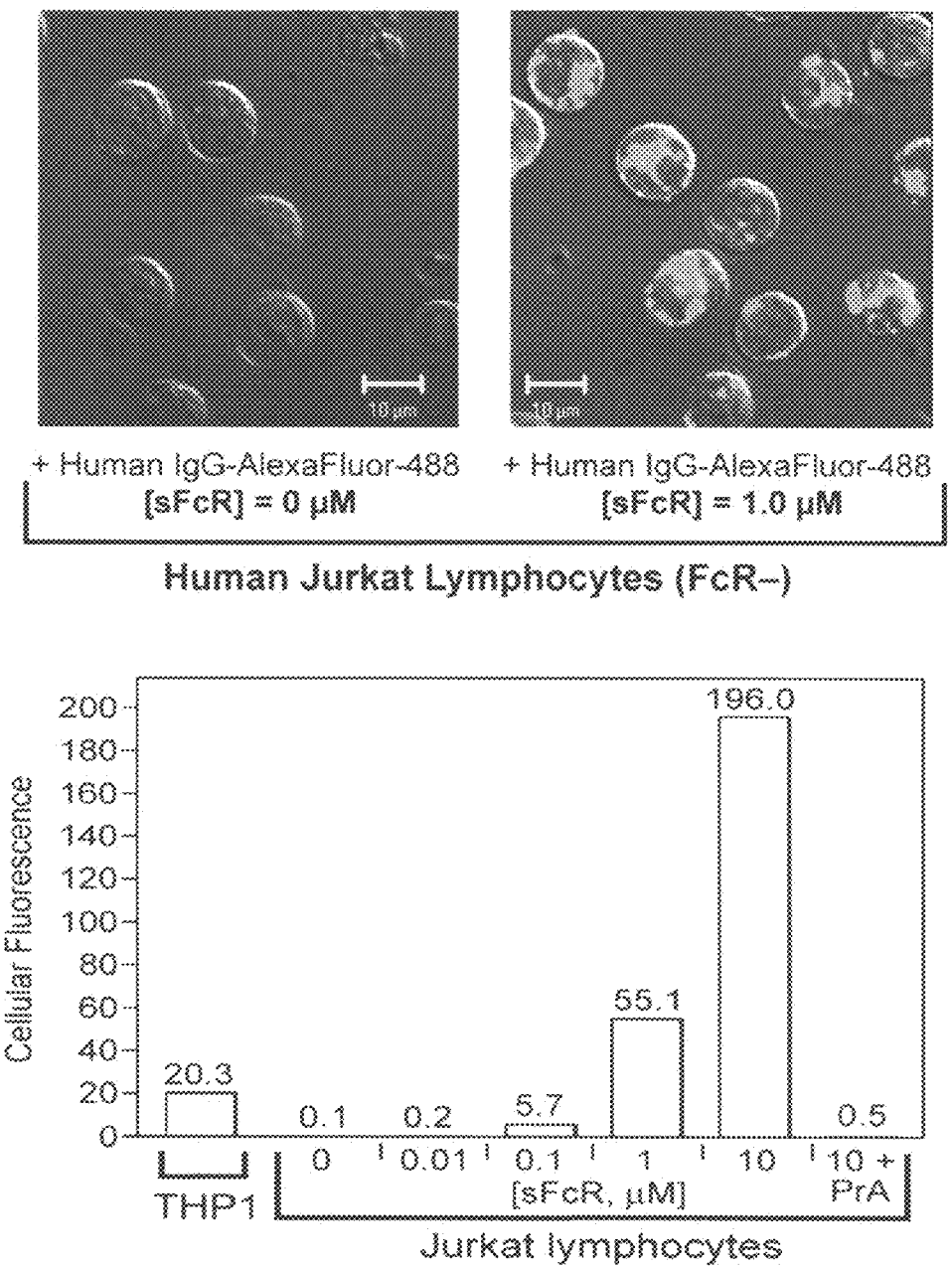
FIG. 26. Uptake of fluorescent human IgG by FcR$^+$ and FcR$^-$ human cells. Micrographs shown on the top. Confocal laser scanning and DIC images of human THP-1 monocytes (left image) and human Jurkat lymphocytes (middle and right images) treated with green fluorescent human IgG. The Jurkat lymphocytes on the right were additionally treated with the synthetic Fc receptor (1 micromolar). sFcR: synthetic Fc receptor. Histogram shown on the bottom: Flow cytometric quantitation of cellular uptake of fluorescent human IgG by THP-1 monocytes and Jurkat lymphocytes. sFcR: synthetic Fc receptor. PrA: Protein A, a competitor that binds to the Fc region of the IgG.
Figure 27:
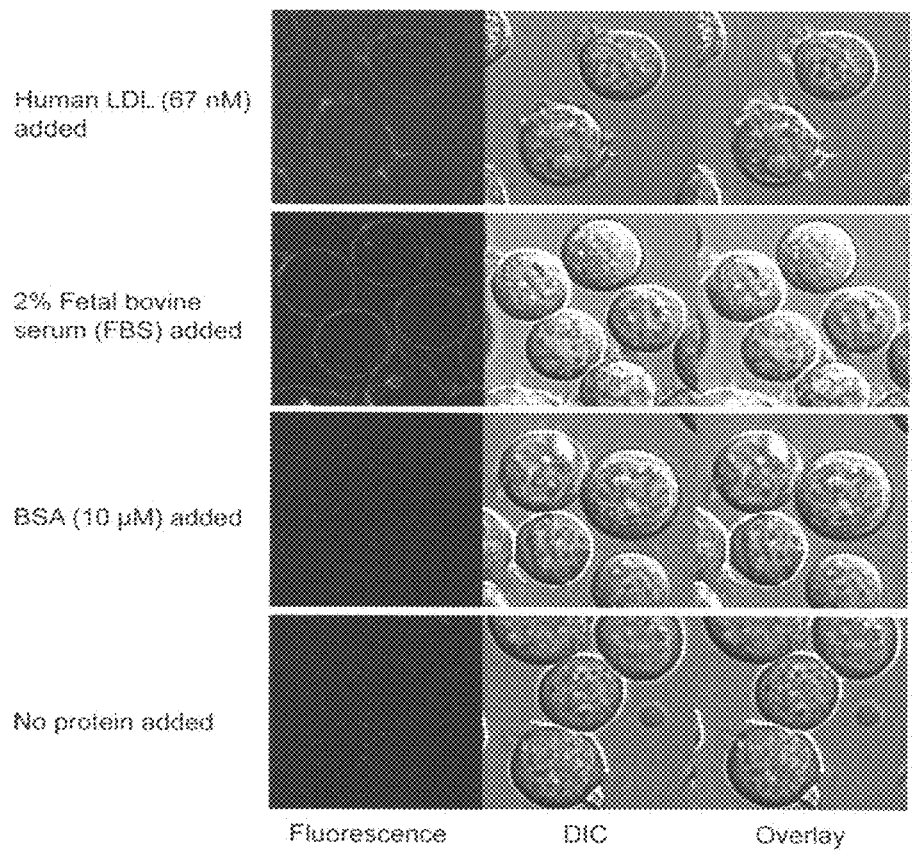
FIG. 27. Uptake of synthetic receptors by certain mammalian cells requires low-density lipoprotein (LDL). Jurkat lymphocytes in RPMI media (no serum) were treated for 5 min with the fluorescent synthetic receptor shown (10 µM) under conditions listed to the left of the images and imaged by confocal laser scanning (left) and DIC (middle) microscopy. Significant cellular fluorescence resulting from uptake of the synthetic receptor was only observed in the presence of LDL or FBS (containing LDL). These results illustrate the use of LDL as a delivery system for synthetic receptors.
Figure 27:
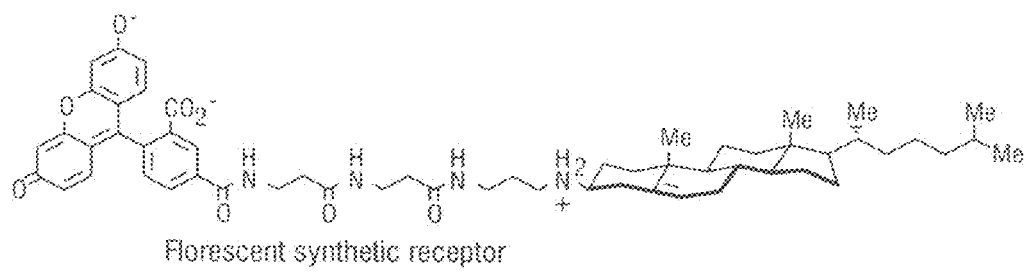

Assays of uptake of AcGFP—oligohistidine fusion proteins. Preload conditions: To Jurkat lymphocytes (7×10$^5$) in RPMI media (0.5 mL) was added synthetic receptor 1 (typical final [Receptor 1]=10 μM) in DMSO (final [DMSO]=1%). These cells were incubated at 37° C. for 1 h to load the receptor into cellular plasma membranes. The cells were washed with RPMI media (0.5 mL) to remove unincorporated receptor/DMSO and resuspended in fresh media (87.6 μL). To these cells was added a solution containing aqueous Ni(OAc)$_2$ (4 μL, 2.5 mM, typical final [Ni(OAc)$_2$]=100 μM) and oligohistidine tagged AcGFP (8.4 μL of 1.19 mg/mL, typical final [AcGFP]=3.2 μM). Cells were maintained at 37° C. for 4 h to promote synthetic receptor-mediated endocytosis. Prior to analysis, treated cells were washed with disodium NTA in media (400 μM, 0.5 mL) and further incubated in media containing disodium NTA (400 μM, 0.5 mL) for 30 min to compete away any non-internalized protein. Cells were centrifuged, the supernatant was discarded, and the cells were resuspended in media (0.5 mL) for analysis by confocal microscopy and flow cytometry. For the competitive inhibition of uptake experiment shown in FIG. 25, Panel A (labeled: +NTA (0.4 mM)), disodium NTA (400 μM) was included in the media during the 4 h incubation with AcGFP and Ni(OAc)$_2$. In FIG. 25, Panels A-D, the concentration of oligohistidine-tagged AcGFP protein was 3.2 μM. In Panels A, C, and D, the metal acetate concentration was 100 μM. In Panels B-D, the concentration of synthetic receptor 1 was 10 μM.

Premix conditions (FIG. 25, Panel A, last bar on the right): Jurkat lymphocytes (7×10$^5$) in RPMI media (100 μL total volume) were incubated 37° C. with a preequilibrated solution of synthetic receptor 1 (10 μM), Ni(OAc)$_2$ (100 μM), AcGFP(His)$_{10}$ (3.2 μM), and DMSO (1%) for 4 h. Prior to analysis, treated cells were washed with disodium NTA in media (400 μM, 0.5 mL) followed by an additional 30 min incubation with media containing disodium NTA (400 μM, 0.5 mL) to compete away any non-internalized protein. Cells were centrifuged, the supernatant was discarded, and the cells were resuspended in media (0.5 mL) for analysis by flow cytometry.

Analysis of cytotoxicity of protein delivery. Jurkat lymphocytes were treated under the preload protein uptake assay conditions ([Receptor 1]=10 μM (preloaded for 1 h); [AcGFP]=3.2 μM; [Ni(OAc)$_2$]=100 μM (protein and metal acetate added for an additional 4 h). These cells were washed with disodium NTA, washed with fresh media, and incubated for an additional 48 h at 37° C. The dead-cell stain propidium iodide (10 μg/mL) was added to cells prior to analysis, and viability was quantified by flow cytometry forward and side-scatter dot plots. No significant effects on viability or cellular morphology were observed under these conditions.

Figure 22:
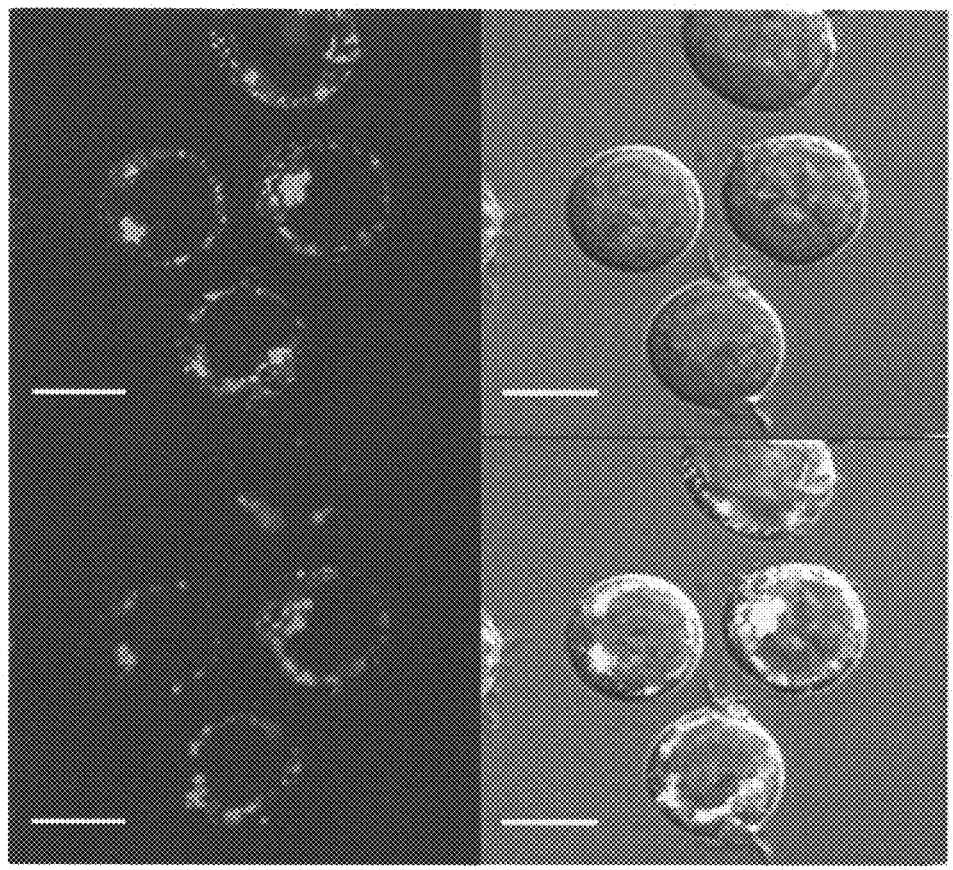
FIG. 22. Delivery of oligohistidine-tagged AcGFP to endosomes and lysosomes. Jurkat lymphocytes were treated with synthetic receptor 1 (10 μM) at 37° C. for 1 h, the cells were washed with media, and Ni(OAc)$_2$ (100 μM), green fluorescent AcGFP(His)$_{10}$ (3.2 μM), and red fluorescent DiI-loaded LDL (50 μg/mL (~0.1 μM)) were added at 37° C. for an additional 4 h. Cells were imaged by confocal laser scanning (left) and DIC microscopy (right). Green fluorescence is shown in the upper left panel. Red fluorescence is shown in the lower left panel. Colocalization of green and red fluorescence is shown in yellow overlaid on the DIC image in the lower right panel. Scale bar=10 μm.
Figure 23:
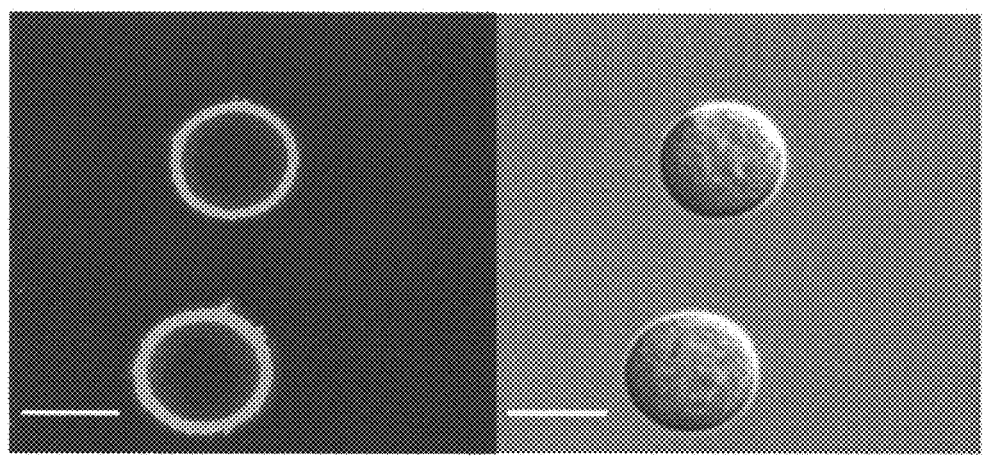
FIG. 23. Inhibition of protein uptake at 4° C. Jurkat lymphocytes were treated with synthetic receptor 1 (10 μM) at 37° C. for 1 h, washed to remove unincorporated receptors, the cells were cooled to 4° C., and AcGFP(His)$_{10}$ (3.2 μM) and Ni(OAc)$_2$ (100 μM) were added at 4° C. for 4 h. Cells were imaged by confocal laser scanning (left) and DIC microscopy (right). Scale bar=10 μm.

Quantification of the number of receptors on the surface of Jurkat lymphocytes. Jurkat lymphocytes (7×10$^5$) in RPMI media (0.5 mL) were treated with synthetic receptor 1 (10 μM final conc.) in DMSO (1% final DMSO conc.). These receptor-treated cells were incubated at 37° C. for 1 h, washed with ice-cold RPMI media (0.5 mL) to remove unincorporated receptor/DMSO, and resuspended in ice-cold media (100 μL) containing Ni(OAc)$_2$ (100 μM) and excess AcGFP(His)$_{10}$ (final concentration=19.2 μM). Cells were maintained at 4° C. for 1 h to saturate the NTA sites on the cell surface. Prior to analysis by confocal microscopy and flow cytometry, treated cells were washed ice-cold media (0.5 mL). As shown in FIG. 22, confocal microscopy revealed that AcGFP(His)$_{10}$ was exclusively localized on the cell surface, and analysis by flow cytometry revealed a cellular fluorescence of 377.1. Construction of a fluorescence calibration curve with Sphero Rainbow Calibration particles (Spherotech) enabled calculation of 39,300,000 molecules of equivalent fluorescein (MEFL) per cell (based on analysis of 680,000 cells). From the fluorescence quantum yield of fluorescein of 0.93 and the fluorescence quantum yield of 0.82 for AcGFP, the average number of receptors per cell was calculated to be ~45,000,000.

Plasmid construction.

The gene encoding AcGFP was amplified by PCR using primers 5'-EcoRI-XhoI-AcGFP (5'-AGTCGAATTCG-GTCTCGAGATGGTGAGCAAGGGC-3'), 3'-SalINoStop-AcGFP (5'-GACTGTCGACCTTGTACAGCTCATC-3'), and pAcGFP1(BD biosciences) as the template to append flanking EcoRI and SalI restriction sites. This PCR product was digested with EcoRI and SalI and inserted into EcoRI/XhoI-digested vectors pSA4 and pSLH2, derivatives of vector pLM$^3$ that add decahistidine (pSA4) or hexahistidine (pSLH2) peptides, followed by a stop codon, to the C-terminus of the gene. The resulting AcGFP(His)$_{10}$ and AcGFP(His)$_6$ genes were digested with EcoRI/SalI and ligated to the EcoRI/SalI-digested vector pSM1, a derivative of pLM$^3$ modified by S. Martin to add a hemagglutinin (HA) epitope tag (flanked by in-frame restriction sites: MfeI-MASYPYD-VPDYASP-EcoRI) to the N-terminus of these proteins.

Protein Overexpression.

Figure 21:
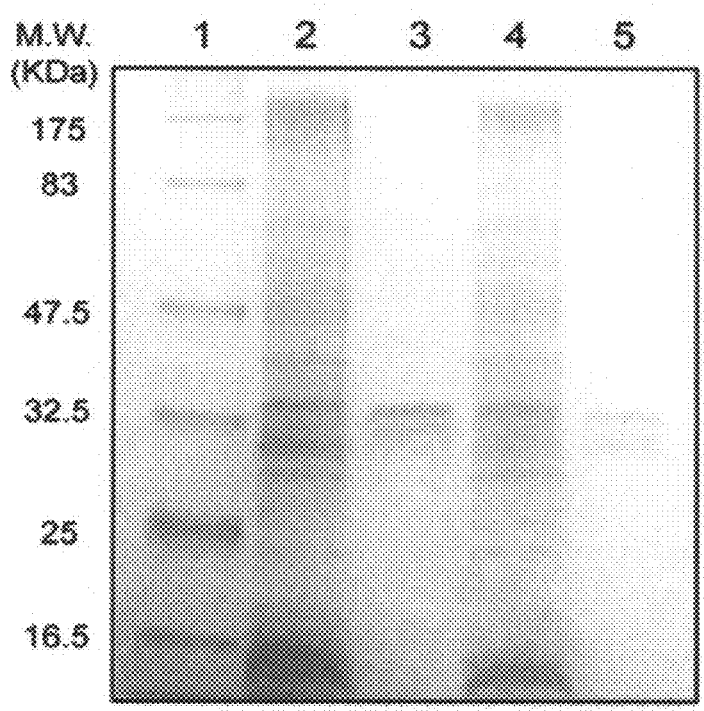
FIG. 21. SDS PAGE analysis of oligohistidine-tagged AcGFP proteins. Lane 1: Protein molecular weight marker. Lane 2: Crude lysate from cells expressing AcGFP(His)$_{10}$. Lane 3: Purified AcGFP(His)$_{10}$. Lane 4: Crude lysate from cells expressing AcGFP(His)$_6$. Lane 5: Purified AcGFP (His)$_6$.

E. coli strain BL21(DE3)pLysS was transformed with plasmids encoding AcGFP(His)$_6$ or AcGFP(His)$_{10}$. These transformed cells were grown to saturation in Luria Broth medium (LB, Difco/BD biosciences) containing ampicillin and chloramphenicol. Saturated cultures (8 mL) were inoculated into LB (100 mL) containing ampicillin (100 μg/mL) and chloramphenicol (20 μg/mL) and incubated with shaking at 37° C. to an optical density of 0.6 (600 nm). Protein expression was induced by addition of IPTG (Invitrogen, final concentration=1 mM). The cultures were shaken at 30° C. for 5 h and cells harvested by centrifugation (4400 rpm, 10 min). The cell pellets were resuspended in Bacterial Protein Extraction Reagent (BPER, Pierce, 3 mL). The cells were shaken at 30° C. for 30 min, centrifuged (10,000 rpm, 5 min) and the supernatant was applied to packed Talon resin (7.5 mL, Clontech/BD biosciences) prewashed with phosphate buffered saline (DPBS, pH 8). The resin was washed with cold DPBS (5×5 mL), and the protein was eluted from the resin by washing with DPBS containing imidazole (300 mM, 2×2 mL). The eluate was concentrated by centrifugation against a protein-impermeable membrane (Millipore centricon concentrator, 10K) and washed at 4° C. with cold DPBS (5×1.5 mL) to remove the imidazole. As shown in FIG. 21, proteins were analyzed by SDS PAGE on a 15% polyacrylamide gel (Cambrex) and detected by staining with coomassie dye. The concentration of the protein was quantified using the Coomassie Plus protein assay reagent (Pierce). The purified proteins were stored at final concentrations of: 1.19 mg/mL (AcGFP(His)$_{10}$, 1000 μL) and 1.09 mg/mL, (AcGFP(His)$_6$, 750 μL).

Amino acid sequences of AcGFP proteins expressed in E. coli. In addition to the C-terminal oligohistidine sequence, these proteins also include an N-terminal hemagglutinin (HA) epitope tag (sequence: YPYDVPDYA).

AcGFP(His)$_6$
MRGSGTELQLMASYPYDVPDYASPEFGLEMVSKGAELFTGIVPILIEL

NGDVNGHKFSVSGEGEGDATYGKLTLKFICTTGKLPVPWPTLVTTLSY

GVQCFSRYPDHMKQHDFFKSAMPEGYIQERTIFFEDDGNYKSRAEVKF

EGDTLVNRIELTGTDFKEDGNILGNKMEYNYNAHNVYIMTDKAKNGIK

VNFKIRHNIEDGSVQLADHYQQNTPIGDGPVLLPDNHYLSTQSALSKD

PNEKRDHMIYFGFVTAAAITHGMDELYKVEGTHHHHHH

AcGFP(His)$_{10}$
MRGSGTELQLMASYPYDVPDYASPEFGLEMVSKGAELFTGIVPILIEL

NGDVNGHKFSVSGEGEGDATYGKLTLKFICTTGKLPVPWPTLVTTLSY

GVQCFSRYPDHMKQHDFFKSAMPEGYIQERTIFFEDDGNYKSRAEVKF

EGDTLVNRIELTGTDFKEDGNILGNKMEYNYNAHNVYIMTDKAKNGIK

VNFKIRHNIEDGSVQLADHYQQNTPIGDGPVLLPDNHYLSTQSALSKD

PNEKRDHMIYFGFVTAAAITHGMDELYKVEGTHHHHHHHHHH

Example 23

Oligohistidine peptides are often fused to proteins to provide affinity tags that facilitate protein purification. To enable these peptides to function as CPPs, we synthesized an artificial cell surface receptor (1) comprising the plasma membrane anchor N-alkyl-3β-cholesterylamine linked to the metal chelator nitrilotriacetic acid (NTA). N-Alkyl-3β-cholesterylamine derivatives can function as prosthetic molecules active on the surface of living mammalian cells because this steroid can insert into cellular plasma membranes, project linked headgroups from the cell surface, and rapidly cycle between the plasma membrane and intracellular endosomes, similar to many naturally-occuring cell surface receptors.[8] The NTA motif binds tightly to nickel, cobalt, copper, and zinc dications, and immobilized metal chelate chromatography (IMAC) with NTA-linked supports is widely used to purify proteins fused to His-tags. Other lipids linked to NTA headgroups have also been reported.[9,10]

Receptor 1 was synthesized from 3β-cholesterylamine (2)[8] as shown in Scheme 1. Alkylation of 2 with ethyl 5-bromovalerate, followed by Boc protection of the secondary amine to afford 3, was found to provide an improved route to protected N-alkyl derivatives of the membrane anchor. Addition of a linker shown to increase the population of these compounds on the cell surface,[8] acylation with a protected NTA derivative, and final deprotection afforded 1 in 47% overall yield.

As representative His-tagged proteins, we overexpressed the monomeric green fluorescent protein AcGFP fused to C-terminal (His)$_6$ and (His)$_{10}$ peptides and purified these proteins by IMAC. The (His)$_{10}$ peptide binds Ni-NTA complexes ~6-fold more tightly than (His)$_6$. For example, (His)$_6$ and (His)$_{10}$ peptides fused to 5HT$_3$R serotonin receptors exhibit affinities for Ni-NTA derivatives of $K_d$=1.05 μM and $K_d$=166 nM, respectively.[11]

Figure 24:
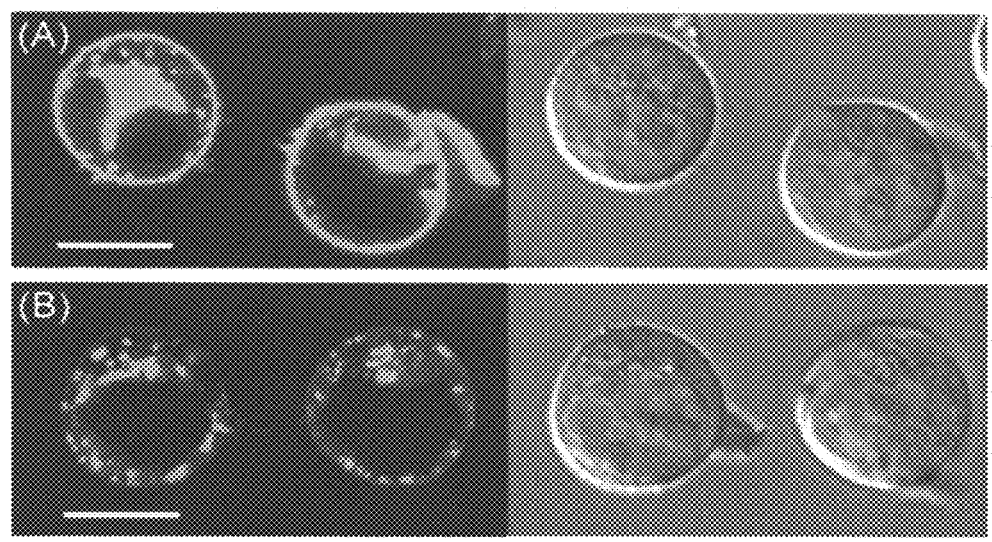
FIG. 24. Confocal laser scanning (left) and differential interference contrast (right) micrographs of living Jurkat lymphocytes. Cellular plasma membranes were preloaded with receptor 1 (10 μM) for 1 h at 37° C., cells were washed with fresh media, and media containing AcGFP-His$_{10}$ (3.2 μM) and Ni(OAc)$_2$ (100 μM) was added for an additional 4 h at 37° C. Cells shown in Panel A were imaged immediately after this treatment. Cells shown in Panel B were washed with NTA (400 μM) prior to microscopy to remove non-internalized protein from the cell surface. Scale bar=10 μm.

To qualitatively examine the ability of receptor 1 to mediate the cellular uptake of His-tagged proteins, human Jurkat T-lymphocytes were treated with 1 (10 μM) for one hour to load this compound into the outer leaflet of the cellular plasma membrane. These cells were washed and subsequently treated with a solution of AcGFP(His)$_{10}$ (3.2 μM) and Ni(OAc)$_2$ (100 μM) for an additional four hours. As shown in FIG. 24 (panel A), examination of these cells by confocal laser scanning microscopy revealed fluorescent protein both on cell surface and in defined intracellular compartments. Washing the cells with disodium NTA (400 μM) as a chelator removed the bound protein from the cell surface, enabling closer examination of the intracellular distribution (FIG. 24, panel B). Delivery of AcGFP(His)$_6$ under these conditions provided similar results, but the cells were 4-fold less fluorescent (FIG. 25, Panel D). The fate of internalized AcGFP(His)$_{10}$ was examined by coadministration with DiI-loaded low density lipoprotein (LDL), a protein internalized by receptor-mediated endocytosis, as a red fluorescent marker of endosomes and lysosomes.[12] Substantial colocalization of red and green. fluorophores was observed under these conditions (supporting information). This delivery to endosomes and lysosomes represents a common destination of proteins fused to CPPs.[13]

Quantitative analysis by flow cytometry of synthetic receptor-mediated uptake is shown in FIG. 25. Intracellular delivery of AcGFP(His)$_{10}$>600-fold above basal levels of endocytosis was achieved by preloading the cellular plasma membrane with receptor 1 (10 μM) for 1 h followed by addition of the protein (3.2 μM) and Ni(OAc)$_2$ (100 μM). Higher receptor concentrations, addition of disodium NTA as a competitor, or premixing the receptor with the protein and metal resulted in lower levels of uptake (panel A). Significantly higher or lower concentrations of Ni(OAc)$_2$ were less effective mediators of uptake (panel B), and omission control experiments confirmed the importance of all three components (panel C). Comparison of diacetates of Ni, Co, Cu, and Zn revealed that Ni(OAc)$_2$ was the most effective metal for delivery of both (His)$_6$ and (His)$_{10}$ fusion proteins.

Consistent with the mechanism of synthetic receptor-mediated endocytosis,[8] uptake of His-tagged AcGFP proteins was blocked by cooling cells to 4° C. (data provided in the supporting information). These conditions enabled quantification of the number of synthetic receptors on the cell surface. Jurkat lymphocytes were treated with 1 (10 μM) for 1 h at 37° C., the cells were washed, chilled to 4° C., and excess AcGFP (His)$_{10}$ (19 μM) and Ni(OAc)$_2$ (100 μM) was added to saturate the surface-bound NTA groups. Comparison of these cells with fluorescent bead standards by flow cytometry revealed an average of 45,000,000 synthetic receptors per cell surface. Previous studies of related compounds suggest that a similar population of synthetic receptors resides in intracellular endosomes.[8]

Heavy metals such as Ni$^{2+}$ exhibit dose-dependent toxicity to biological systems. To examine the toxicity of this metal acetate and protein delivery, cellular viability was examined by flow cytometry. In these experiments, Jurkat lymphocytes were treated with receptor 1 (10 μM, 1 h), followed by AcGFP (His)$_{10}$ (3.2 μM), and Ni(OAc)$_2$ (100 μM, 4 h) to enhance protein uptake by 600-fold. Cells were washed with disodium NTA to remove cell surface protein and were cultured for an additional 48 h. Cellular viability was determined by light scattering and staining the nuclei of membrane-compromised dead cells with the fluorophore propidium iodide. Under these conditions, 97% of the cells were viable, compared with 98.6% of untreated controls, and no effects on cellular morphology were observed. Other studies have similarly reported low toxicity of nickel salts at ≦160 μM in cell culture.[14] By enabling common oligohistidine affinity tags to function as cell penetrating peptides, synthetic receptor 1 provides a potentially versatile new probe of cellular biology.

Example 24

References for Examples 16-23

(1) Boonyarattanakalin, S.; Martin, S. E.; Dykstra, S. A.; Peterson, B. R. *J. Am. Chem. Soc.* 2004, 126, 16379-16386.
(2) Dorn, I. T.; Neumaier, K. R.; Tampe, R. *J. Am. Chem. Soc.* 1998, 120, 2753-2763.
(3) Sodeoka, M.; Larson, C. J.; Chen, L.; Leclair, K. P.; Verdine, G. L. *Bioorg. Med. Chem. Lett.* 1993, 3, 1089-1094.

Example 25

A Synthetic Scheme Describing the Synthesis of the Lipid-Mimicking Synthetic Receptors, e.g. CRP Receptors (Lipid Mimics that Promote Cellular Apoptosis in the Presence of C-Reactive Protein)

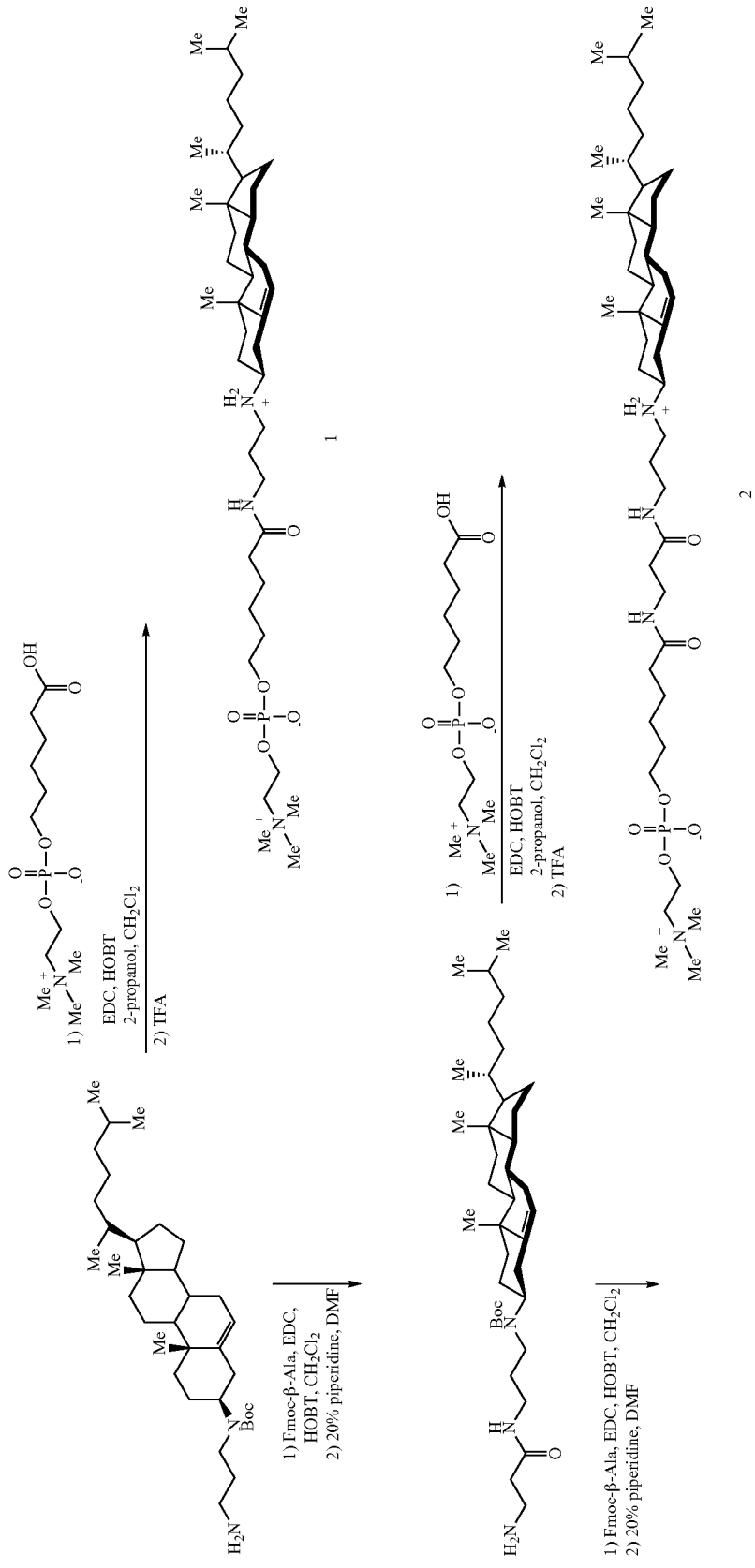

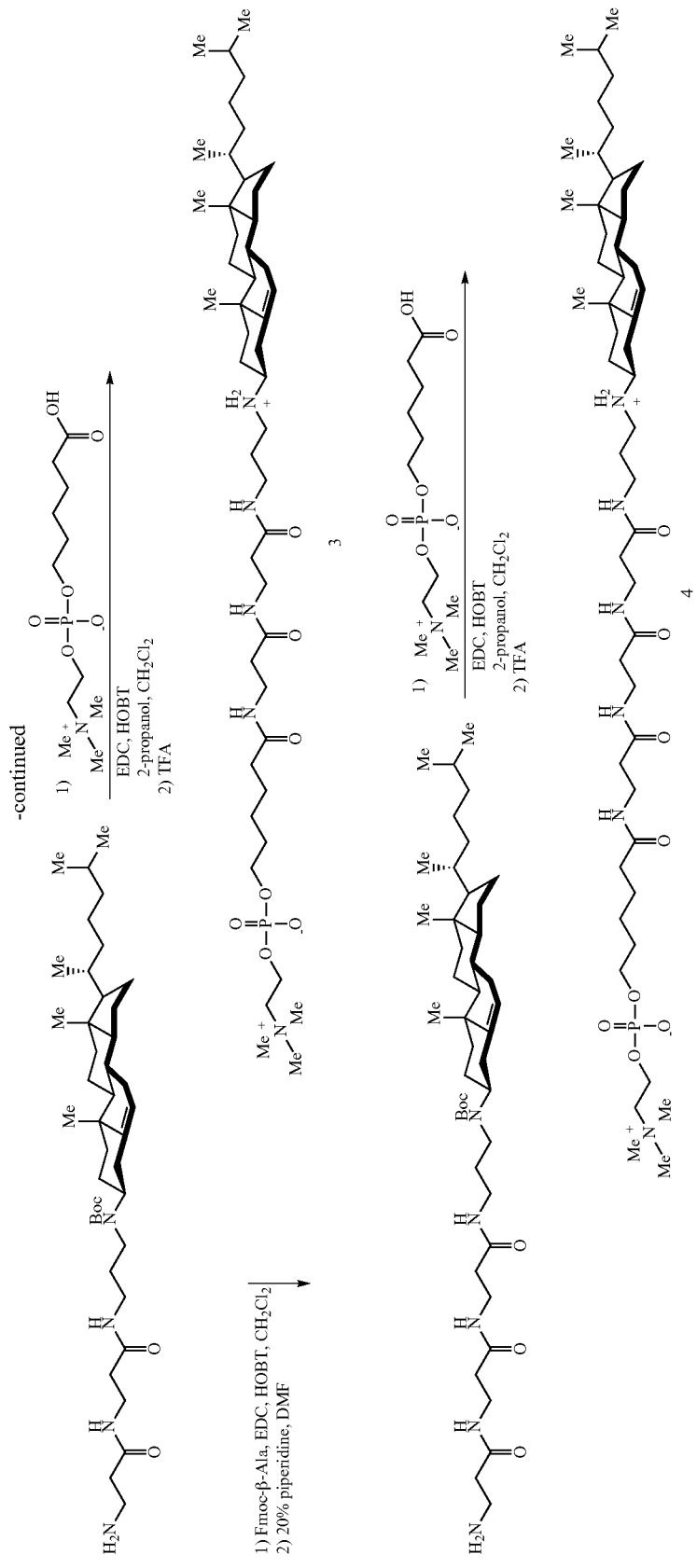

Example 26

Lipid-Mimicking Receptors

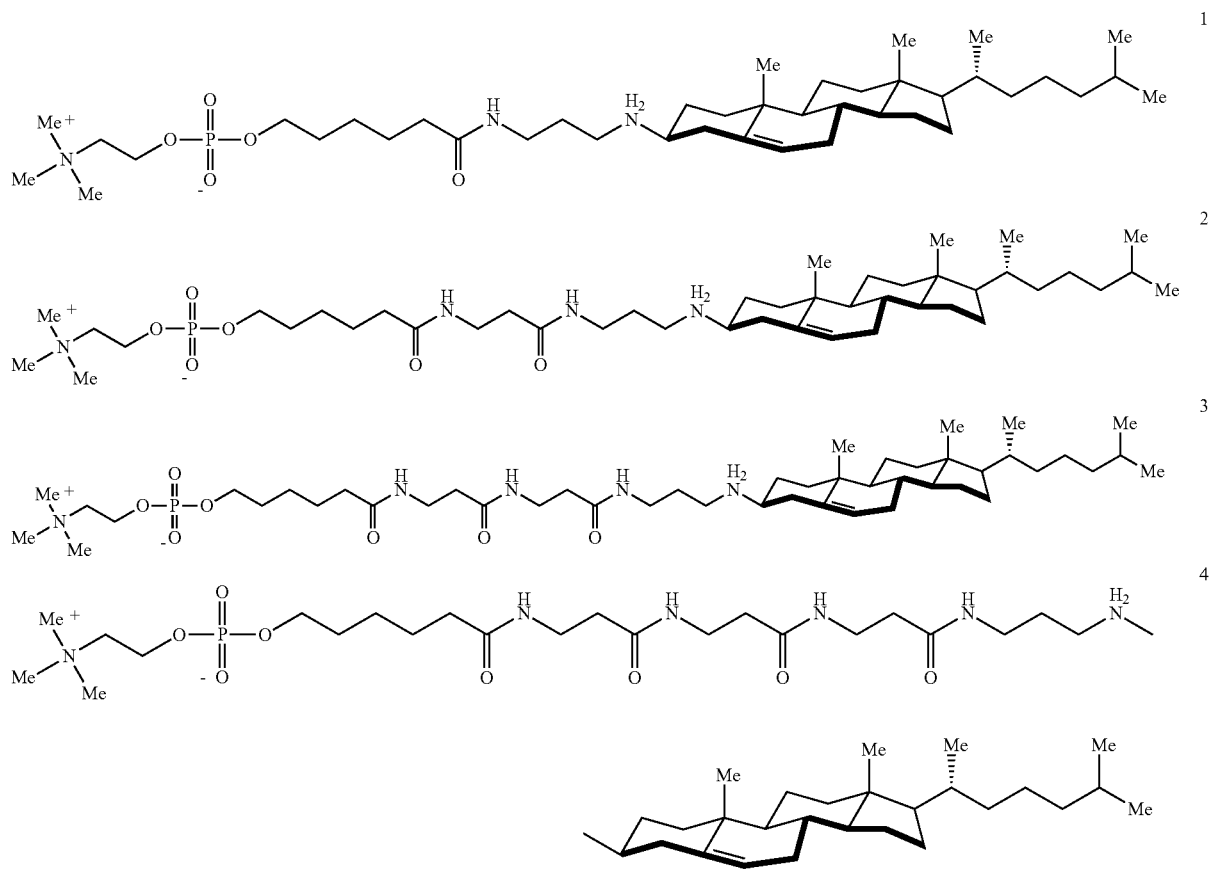

Example 27

References (1) Brooks, H.; Lebleu, B.; Vives, E. Adv. Drug Deliv. Rev. 2005, 57, 559-577.
(2) Wender, P. A.; Mitchell, D. J.; Pattabiraman, K.; Pelkey, E. T.; Steinman, L.; Rothbard, J. B. Proc. Natl. Acad. Sci. U.S.A. 2000, 97, 13003-13008.
(3) Umezawa, N.; Gelman, M. A.; Haigis, M. C.; Raines, R. T.; Gellman, S. H. J. Am. Chem. Soc. 2002, 124, 368-369.
(4) Jiang, H.; O'Neil E, J.; Divittorio, K. M.; Smith, B. D. Org. Lett. 2005, 7, 3013-3016.
(5) Fuchs, S. M.; Raines, R. T. Biochemistry 2004, 43, 2438-2444.
(6) Maiolo, J. R.; Ferrer, M.; Ottinger, E. A. Biochim. Biophys. Acta 2005, 1712, 161-172.
(7) Rothbard, J. B.; Jessop, T. C.; Wender, P. A. Adv. Drug Deliv. Rev. 2005, 57, 495-504.
(8) Boonyarattanakalin, S.; Martin, S. E.; Dykstra, S. A.; Peterson, B. R. J. Am. Chem. Soc. 2004, 126, 16379-16386.
(9) Hodges, H. B.; Thou, M.; Haldar, S.; Anderson, J. L.; Thompson, D. H.; Hrycyna, C. A. Bioconjug. Chem. 2005, 16, 490-493.
(10) van Broekhoven, C. L.; Parish, C. R.; Vassiliou, G.; Altin, J. G. J. Immunol. 2000, 164, 2433-2443.
(11) Guignet, E. G.; Hovius, R.; Vogel, H. Nat. Biotechnol. 2004, 22, 440-444.
(12) Ghosh, R. N.; Gelman, D. L.; Maxfield, F. R. J. Cell Sci. 1994, 107, 2177-2189.
(13) Young, J. C.; Moarefi, I.; Hartl, F. U. J. Cell Biol. 2001, 154, 267-273.
(14) Shiao, Y. H.; Lee, S. H.; Kasprzak, K. S. Carcinogenesis 1998, 19, 1203-1207.
(15) Williams, D. H.; Bardsley, B. Angew. Chem. Int. Ed. 1999, 38, (9), 1173-1193.
(16) Krut, O.; Sommer, H.; Kronke, M. J. Antimicrob. Chemo. 2004, 53, (2), 167-173.
(17) Kintarak, S.; Whawell, S. A.; Speight, P. M.; Packer, S.; Nair, S. P. Infect. Immun. 2004, 72, (10), 5668-5675.
(18) Conner, S. D.; Schmid, S. L. Nature 2003, 422, (6927), 37-44.
(19) Young, J. C.; Moarefi, I.; Hartl, F. U. J. Cell Biol. 2001, 154, (2), 267-273.
(20) Chu, Y. H.; Dunayevskiy, Y. M.; Kirby, D. P.; Vouros, P.; Karger, B. L. J. Am. Chem. Soc. 1996, 118, (33), 7827-7835.
(21) Boonyarattanakalin, S.; Martin, S. E.; Dykstra, S. A.; Peterson, B. R. J. Am. Chem. Soc. 2004, 126, (50), 16379-16386.
(22) Conner, S. D.; Schmid, S. L. Nature 2003, 422, 37-44.
(23) Smith, D. C.; Lord, J. M.; Roberts, L. M.; Johannes, L. Semin. Cell. Dev. Biol. 2004, 15, 397-408.
(24) Sandvig, K.; van Deurs, B. FEBS Lett 2002, 529, 49-53.
(25) Maxfield, F. R.; McGraw, T. E. Nat. Rev. Mol. Cell. Biol. 2004, 5, 121-132.

(26) Vyas, S. P.; Singh, A.; Sihorkar, V. Crit. Rev. Ther. Drug Carrier. Syst. 2001, 18, 1-76.
(27) Lu, Y.; Sega, E.; Leamon, C. P.; Low, P. S. Adv. Drug Deliv. Rev. 2004, 56, 1161-1176.
(28) Rui, Y. J.; Wang, S.; Low, P. S.; Thompson, D. H. J. Am. Chem. Soc. 1998, 120, 11213-11218.
(29) Lee, R. J.; Low, P. S. J. Biol. Chem. 1994, 269, 3198-3204.
(30) Qian, Z. M.; Li, H.; Sun, H.; Ho, K. Pharmacol. Rev. 2002, 54, 561-587.
(31) Chung, N. S.; Wasan, K. M. Adv. Drug Deliv. Rev. 2004, 56, 1315-1334.
(32) Hussey, S. L.; He, E.; Peterson, B. R. J. Am. Chem. Soc. 2001, 123, 12712-12713.
(33) Martin, S. E.; Peterson, B. R. Bioconjugate Chem. 2003, 14, 67-74.
(34) Hussey, S. L.; Peterson, B. R. J. Am. Chem. Soc. 2002, 124, 6265-6273.
(35) de Kruif, J.; Tijmensen, M.; Goldsein, J.; Logtenberg, T. Nat. Med. 2000, 6, 223-227.
(36) Saxon, E.; Bertozzi, C. R. Science 2000, 287, 2007-2010.
(37) Mahal, L. K.; Yarema, K. J.; Bertozzi, C. R. Science 1997, 276, 1125-1128.
(38) Prescher, J. A.; Dube, D. H.; Bertozzi, C. R. Nature 2004, 430, 873-877.
(39) George, N.; Pick, H.; Vogel, H.; Johnsson, N.; Johnsson, K. J. Am. Chem. Soc. 2004, 126, 8896-8897.
(40) Kellam, B.; De Bank, P. A.; Shakesheff, K. M. Chem. Soc. Rev. 2003, 32, 327-337.
(41) Kato, M.; Mrksich, M. J. Am. Chem. Soc. 2004, 126, 6504-6505.
(42) Manes, S.; del Real, G.; Martinez, A. C. Nat. Rev. Immunol. 2003, 3, 557-568.
(43) Brown, D. A.; London, E. Annu. Rev. Cell Dev. Biol. 1998, 14, 111-136.
(44) Simons, K.; Ikonen, E. Science 2000, 290, 1721-1726.
(45) Kirchhausen, T. Annu. Rev. Biochem. 2000, 69, 699-727.
(46) Schmid, S. L. Annu. Rev. Biochem. 1997, 66, 511-548.
(47) Brown, D. A.; London, E. J. Biol. Chem. 2000, 275, 17221-17224.
(48) Maxfield, F. R. Curr. Opin. Cell Biol. 2002, 14, 483-487.
(49) Gaus, K.; Gratton, E.; Kable, E. P.; Jones, A. S.; Gelissen, I.; Kritharides, L.; Jessup, W. Proc. Natl. Acad. Sci. U.S.A. 2003, 100, 15554-15559.
(50) Edidin, M. Annu. Rev. Biophys. Biomol. Struct. 2003, 32, 257-283.
(51) Zacharias, D. A.; Violin, J. D.; Newton, A. C.; Tsien, R. Y. Science 2002, 296, 913-916.
(52) Simons, K.; Toomre, D. Nat. Rev. Mol. Cell. Biol. 2000, 1, 31-39.
(53) Ikonen, E. Curr. Opin. Cell Biol. 2001, 13, 470-477.
(54) Singh, R. D.; Puri, V.; Valiyaveettil, J. T.; Marks, D. L.; Bittman, R.; Pagano, R. E. Mol. Biol. Cell 2003, 14, 3254-3265.
(55) Nichols, B. J. Curr. Biol. 2003, 13, 686-690.
(56) Lancet, D.; Pecht, I. Biochemistry 1977, 16, 5150-5157.
(57) Yang, T.; Baryshnikova, O. K.; Mao, H.; Holden, M. A.; Cremer, P. S. J. Am. Chem. Soc. 2003, 125, 4779-4784.
(58) Kan, C. C.; Yan, J.; Bittman, R. Biochemistry 1992, 31, 1866-1874.
(59) Mancuso, A. J.; Swern, D. Synthesis 1981, 3, 165-185.
(60) Fukuyama, T.; Jow, C. K.; Cheung, M. Tetrahedron Lett. 1995, 36, 6373-6374.
(61) Cedergren, L.; Andersson, R.; Jansson, B.; Uhlen, M.; Nilsson, B. Protein Eng. 1993, 6, 441-448.
(62) Tashiro, M.; Montelione, G. T. Curr. Opin. Struct. Biol. 1995, 5, 471-481.
(63) Patterson, G. H.; Lippincott-Schwartz, J. Science 2002, 297, 1873-1877.
(64) Lentz, B. R.; Talbot, W.; Lee, J.; Zheng, L. X. Biochemistry 1997, 36, 2076-2083.
(65) Alakoskela, J. I.; Kinnunen, P. K. Biophys. J. 2001, 80, 294-304.
(66) Chung, K. N.; Roberts, S.; Kim, C. H.; Kirassova, M.; Trepel, J.; Elwood, P. C. Arch. Biochem. Biophys. 1995, 322, 228-234.
(67) Rodal, S. K.; Skretting, G.; Garred, O.; Vilhardt, F.; van Deurs, B.; Sandvig, K. Mol. Biol. Cell. 1999, 10, 961-974.
(68) Sun, W. C.; Gee, K. R.; Klaubert, D. H.; Haugland, R. P. J. Org. Chem. 1997, 62, 6469-6475.
(69) Hao, M.; Maxfield, F. R. J. Biol. Chem. 2000, 275, 15279-15286.
(70) Munro, S. Cell 2003, 115, 377-388.
(71) Harder, T.; Scheiffele, P.; Verkade, P.; Simons, K. J. Cell Biol. 1998, 141, 929-942.
(72) Dietrich, C.; Volovyk, Z. N.; Levi, M.; Thompson, N. L.; Jacobson, K. Proc. Natl. Acad. Sci. U.S.A. 2001, 98, 10642-10647.
(73) Anderson, R. G.; Jacobson, K. Science 2002, 296, 1821-1825.
(74) Hao, M.; Lin, S. X.; Karylowski, O. J.; Wustner, D.; McGraw, T. E.; Maxfield, F. R. J. Biol. Chem. 2002, 277, 609-617.
(75) Puri, V.; Watanabe, R.; Dominguez, M.; Sun, X.; Wheatley, C. L.; Marks, D. L.; Pagano, R. E. Nat. Cell Biol. 1999, 1, 386-388.
(76) Reaven, E.; Tsai, L.; Azhar, S. J. Biol. Chem. 1996, 271, 16208-16217.
(77) Brown, M. S.; Goldstein, J. L. Angew. Chem. Int. Ed. Engl. 1986, 25, 583-602.
(78) Sato, S. B.; Ishii, K.; Makino, A.; Iwabuchi, K.; Yamaji-Hasegawa, A.; Senoh, Y.; Nagaoka, I.; Sakuraba, H.; Kobayashi, T. J. Biol. Chem. 2004, 279, 23790-23796.
(79) Lenz, M.; Miehe, W. P.; Vahrenwald, F.; Bruchelt, G.; Schweizer, P.; Girgert, R. Anticancer Res. 1997, 17, 1143-1146.
(80) Boonyarattanakalin S, Martin S E, Dykstra S A, Peterson B R. Synthetic mimics of small Mammalian cell surface receptors. J Am Chem Soc. 2004, 126(50):16379-86.

What is claimed is:

1. A method of producing a therapeutic effect by delivering a synthetic cell receptor into a cell comprising:
   contacting said cell with a synthetic cell receptor that inserts into a cell plasma membrane on a cell surface wherein said receptor comprises:
   a target-binding motif, wherein said target-binding motif binds or is covalently linked to a target;
   a linker region linking a membrane-binding element with the target-binding motif, wherein said membrane-binding element anchors said receptor into a cell plasma membrane and is a derivative of 3β-cholesterylamine or 3β-dihydrocholesterylamine;
   triggering receptor-mediated endocytosis of said receptor;
   delivery of said receptor to said cell by an endosome; and
   disrupting said endosome by an endosome disrupter to release said target and produce said therapeutic effect.

2. The method of claim 1 further comprising the recycling of said receptor to said cell surface.

3. The method of claim 1 wherein said cells are infected with a pathogen that secretes membrane-disruptive proteins.

4. The method of claim 3 wherein said pathogen is bacterial, viral or a microorganism.

5. The method of claim 1 wherein said target is a member selected from the group consisting of a protein, polypeptide, peptide, antibody, ligand, cytokine, growth factor, immunoglobulin, nucleic acid, lipid, carbohydrate, membrane, pro-drug, drug, small molecule or a fragment thereof and combinations of the same.

6. The method of claim 1 wherein said endosome disruptor is a member selected from the group consisting of a peptide, protein, nucleic acid, lipid, polymer, or small molecule, an immunoglobulin or a fragment thereof, hemagglutinin or a fragment or variant thereof, listeriolysin O, GALA, endoporter, poly(alkylacrylic acid) and combinations of the same.

7. The method of claim 1 wherein said endosome disruptor is a small molecule or macromolecule that preferentially disrupts membranes at acidic (endosomal) pH (pH≦7).

8. The method of claim 1 wherein said therapeutic effect is bacteriocidal, bacteriostatic, anticancer, antiviral, or any other biological response.

* * * * *

SEQUENCE LISTING

```
<160> NUMBER OF SEQ ID NOS: 7

<210> SEQ ID NO 1
<211> LENGTH: 13
<212> TYPE: PRT
<213> ORGANISM: Artificial
<220> FEATURE:
```

-continued

<223> OTHER INFORMATION: Artificial sequence may be synthesized.

<400> SEQUENCE: 1

Asp Cys Ala Trp His Leu Gly Glu Leu Val Trp Cys Thr
1               5                   10

<210> SEQ ID NO 2
<211> LENGTH: 34
<212> TYPE: DNA
<213> ORGANISM: Artificial
<220> FEATURE:
<223> OTHER INFORMATION: Artificial sequence may be synthesized.

<400> SEQUENCE: 2
agtcgaattc ggtctcgaga tggtgagcaa gggc                                34

<210> SEQ ID NO 3
<211> LENGTH: 25
<212> TYPE: DNA
<213> ORGANISM: Artificial
<220> FEATURE:
<223> OTHER INFORMATION: Artificial sequence may be synthesized.

<400> SEQUENCE: 3
gactgtcgac cttgtacagc tcatc                                          25

<210> SEQ ID NO 4
<211> LENGTH: 14
<212> TYPE: PRT
<213> ORGANISM: Artificial
<220> FEATURE:
<223> OTHER INFORMATION: Artificial sequence may be synthesized.

<400> SEQUENCE: 4

Met Ala Ser Tyr Pro Tyr Asp Val Pro Asp Tyr Ala Ser Pro
1               5                   10

<210> SEQ ID NO 5
<211> LENGTH: 9
<212> TYPE: PRT
<213> ORGANISM: Artificial
<220> FEATURE:
<223> OTHER INFORMATION: Artificial sequence may be synthesized.

<400> SEQUENCE: 5

Tyr Pro Tyr Asp Val Pro Asp Tyr Ala
1               5

<210> SEQ ID NO 6
<211> LENGTH: 278
<212> TYPE: PRT
<213> ORGANISM: Artificial
<220> FEATURE:
<223> OTHER INFORMATION: Artificial sequence may be synthesized.

<400> SEQUENCE: 6

Met Arg Gly Ser Gly Thr Glu Leu Gln Leu Met Ala Ser Tyr Pro Tyr
1               5                   10                  15

Asp Val Pro Asp Tyr Ala Ser Pro Glu Phe Gly Leu Glu Met Val Ser
            20                  25                  30

Lys Gly Ala Glu Leu Phe Thr Gly Ile Val Pro Ile Leu Ile Glu Leu
        35                  40                  45

Asn Gly Asp Val Asn Gly His Lys Phe Ser Val Ser Gly Glu Gly Glu
    50                  55                  60

Gly Asp Ala Thr Tyr Gly Lys Leu Thr Leu Lys Phe Ile Cys Thr Thr

Gly Lys Leu Pro Val Pro Trp Pro Thr Leu Val Thr Thr Leu Ser Tyr
65                  70                  75                  80

Gly Val Gln Cys Phe Ser Arg Tyr Pro Asp His Met Lys Gln His Asp
                85                  90                  95

Phe Phe Lys Ser Ala Met Pro Glu Gly Tyr Ile Gln Glu Arg Thr Ile
            100                 105                 110

Phe Phe Glu Asp Asp Gly Asn Tyr Lys Ser Arg Ala Glu Val Lys Phe
        115                 120                 125

Glu Gly Asp Thr Leu Val Asn Arg Ile Glu Leu Thr Gly Thr Asp Phe
145                 150                 155                 160

Lys Glu Asp Gly Asn Ile Leu Gly Asn Lys Met Glu Tyr Asn Tyr Asn
                165                 170                 175

Ala His Asn Val Tyr Ile Met Thr Asp Lys Ala Lys Asn Gly Ile Lys
            180                 185                 190

Val Asn Phe Lys Ile Arg His Asn Ile Glu Asp Gly Ser Val Gln Leu
        195                 200                 205

Ala Asp His Tyr Gln Gln Asn Thr Pro Ile Gly Asp Gly Pro Val Leu
210                 215                 220

Leu Pro Asp Asn His Tyr Leu Ser Thr Gln Ser Ala Leu Ser Lys Asp
225                 230                 235                 240

Pro Asn Glu Lys Arg Asp His Met Ile Tyr Phe Gly Phe Val Thr Ala
                245                 250                 255

Ala Ala Ile Thr His Gly Met Asp Glu Leu Tyr Lys Val Glu Gly Thr
            260                 265                 270

His His His His His His
        275

<210> SEQ ID NO 7
<211> LENGTH: 282
<212> TYPE: PRT
<213> ORGANISM: Artificial
<220> FEATURE:
<223> OTHER INFORMATION: Artificial sequence may be synthesized.

<400> SEQUENCE: 7

Met Arg Gly Ser Gly Thr Glu Leu Gln Leu Met Ala Ser Tyr Pro Tyr
1               5                   10                  15

Asp Val Pro Asp Tyr Ala Ser Pro Glu Phe Gly Leu Glu Met Val Ser
            20                  25                  30

Lys Gly Ala Glu Leu Phe Thr Gly Ile Val Pro Ile Leu Ile Glu Leu
        35                  40                  45

Asn Gly Asp Val Asn Gly His Lys Phe Ser Val Ser Gly Glu Gly Glu
    50                  55                  60

Gly Asp Ala Thr Tyr Gly Lys Leu Thr Leu Lys Phe Ile Cys Thr Thr
65                  70                  75                  80

Gly Lys Leu Pro Val Pro Trp Pro Thr Leu Val Thr Thr Leu Ser Tyr
                85                  90                  95

Gly Val Gln Cys Phe Ser Arg Tyr Pro Asp His Met Lys Gln His Asp
            100                 105                 110

Phe Phe Lys Ser Ala Met Pro Glu Gly Tyr Ile Gln Glu Arg Thr Ile
        115                 120                 125

Phe Phe Glu Asp Asp Gly Asn Tyr Lys Ser Arg Ala Glu Val Lys Phe
    130                 135                 140

Glu Gly Asp Thr Leu Val Asn Arg Ile Glu Leu Thr Gly Thr Asp Phe
145                 150                 155                 160

-continued

```
Lys Glu Asp Gly Asn Ile Leu Gly Asn Lys Met Glu Tyr Asn Tyr Asn
            165                 170                 175

Ala His Asn Val Tyr Ile Met Thr Asp Lys Ala Lys Asn Gly Ile Lys
            180                 185                 190

Val Asn Phe Lys Ile Arg His Asn Ile Glu Asp Gly Ser Val Gln Leu
        195                 200                 205

Ala Asp His Tyr Gln Gln Asn Thr Pro Ile Gly Asp Gly Pro Val Leu
        210                 215                 220

Leu Pro Asp Asn His Tyr Leu Ser Thr Gln Ser Ala Leu Ser Lys Asp
225                 230                 235                 240

Pro Asn Glu Lys Arg Asp His Met Ile Tyr Phe Gly Phe Val Thr Ala
                245                 250                 255

Ala Ala Ile Thr His Gly Met Asp Glu Leu Tyr Lys Val Glu Gly Thr
            260                 265                 270

His His His His His His His His His
            275                 280
```